US006482811B1

(12) United States Patent
Bacaner et al.

(10) Patent No.: US 6,482,811 B1
(45) Date of Patent: Nov. 19, 2002

(54) BRETYLIUM COMPOSITIONS AND KITS, AND THEIR USE IN PREVENTING AND TREATING CARDIO-VASCULAR CONDITIONS

(76) Inventors: Marvin B. Bacaner, 2900 Thomas Ave. South, Unit 2216, Minneapolis, MN (US) 55416-4153; Maurice M. Kreevoy, 15 S. First St., No. 1619-A, Minneapolis, MN (US) 55401

( * ) Notice: Subject to any disclaimer, the term of this patent is extended or adjusted under 35 U.S.C. 154(b) by 0 days.

(21) Appl. No.: 09/869,940

(22) PCT Filed: Jan. 6, 2000

(86) PCT No.: PCT/US00/00350

§ 371 (c)(1),
(2), (4) Date: Nov. 27, 2001

(87) PCT Pub. No.: WO00/40232

PCT Pub. Date: Jul. 13, 2000

Related U.S. Application Data

(60) Provisional application No. 60/115,143, filed on Jan. 8, 1999, and provisional application No. 60/116,567, filed on Jan. 21, 1999.

(51) Int. Cl.[7] .............................................. A61K 31/615
(52) U.S. Cl. ...................................................... 514/162
(58) Field of Search ........................................ 514/162

(56) References Cited

U.S. PATENT DOCUMENTS

| | | |
|---|---|---|
| 3,038,004 A | 6/1962 | Copp et al. |
| 3,911,125 A | 10/1975 | Bacaner |
| RE29,618 E | 4/1978 | Bacaner |
| 4,147,768 A | 4/1979 | Shaffer et al. |
| 4,849,227 A | 7/1989 | Cho |
| 5,036,106 A | 7/1991 | Bacaner |
| 5,288,497 A | 2/1994 | Stanley et al. |
| 5,288,498 A | 2/1994 | Stanley et al. |
| 5,733,575 A | 3/1998 | Mehra et al. |
| 5,750,148 A | 5/1998 | Maruyama et al. |
| 5,776,501 A | 7/1998 | Kokubo et al. |
| 5,814,336 A | 9/1998 | Kelm et al. |
| 5,914,132 A | 6/1999 | Kelm et al. |
| 5,980,951 A | 11/1999 | Gardner et al. |

FOREIGN PATENT DOCUMENTS

WO WO/87/05505 9/1987

OTHER PUBLICATIONS

R. Neubert, R. Amlacher and A. Hartl, Ion Pair Approach of Bretylium, *Drugs Made in Germany*, 1992, pp. 125–127, vol. 35, No. 4.

Reinhard, Heubert, Silke, Fischer, Influence of lipophilic counter ions on the transport of ionizable hydrophilic drugs, *Journal of Pharmacy & Pharmacology*, Mar. 1991, pp. 204–206, vol. 43, No. 3.

A. Hartl, R. Amlacher, R. Neubert and Carmen Hause, Influence of the ion–pair–formation of bretylium and hexylsalicylic acid on their blood plasma levels in dogs, *Pharmazie 45*, 1990, p. 295.

R. Neubert, et al., Influence of ion–pair–formation on the pharmacokinetic properties of drugs, *Die Pharmazie 43*, 1988.

Reinhard Amlacher, et al., Influence of Ion–pair Formation on the Pharmacokinetic Properties of Drugs, Pharmacokinetic Interactions of Bretylium and Hexylsalicylic Acid in Rabbits, *Journal of Pharmacy & Pharmacology*, Nov. 1991, pp. 794–797, vol. 43, No. 11.

R. Neubert, Carmen Hause, A. Hartl and R. Amlacher, Influence of the ion–pair formation on the pharmacokinetic properties of drugs, *Die Pharmazie 9*, Part 5.

C. J. Coetzee and Henry Freiser, Liquid–Liquid Membrane Electrodes Based on Ion Association Extraction Systems, *Analytical Chemistry*, 1968, pp. 1128–1130.

Marvin Bacaner and Michael Hoey, Synergistic Action of Bretylium with Low Doses of Propranolol Renders the Canine Heart Virtually Invulnerable to Sustained Ventricular Fibrillation, *Circulation Supplement*, Oct. 1987, p. IV–111, vol. 76, No. 4.

R. Neubert, W. Furst, and Beate Wurschi, Arzneimittelpermeation durch kunstliche Lipoidmembranen, *Pharmazie 42*, 1987.

*Primary Examiner*—Raymond Henley, III
(74) *Attorney, Agent, or Firm*—Senniger, Powers, Leavitt & Roedel

(57) ABSTRACT

This invention is directed to novel pharmaceutical compositions and kits comprising bretylium as the active ingredient, as well as methods which use such compositions and kits for preventing and/or treating conditions related to the cardiovascular system.

261 Claims, 1 Drawing Sheet

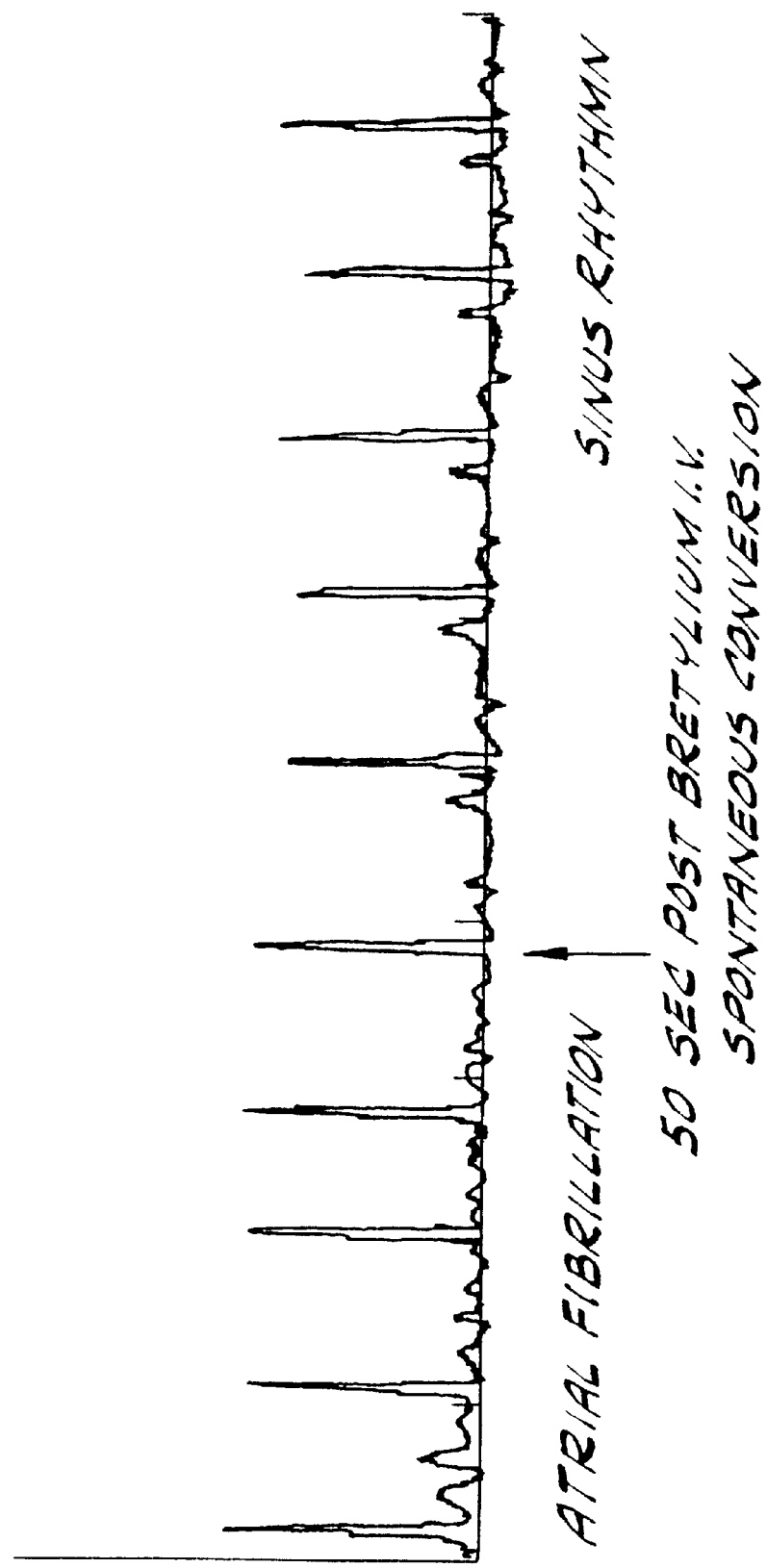

BRETYLIUM COMPOSITIONS AND KITS, AND THEIR USE IN PREVENTING AND TREATING CARDIO-VASCULAR CONDITIONS

CROSS-REFERENCES TO RELATED APPLICATIONS

This Application is a 35 of U.S.C. 0371 national stage application based on PCT application Ser. No. PCT/US00/00350 filed Jan. 6, 2000, which claims priority from U.S. Provisional Application Serial No. 60/115,143 filed on Jan. 8, 1999 and from U.S. Provisional Application Ser. No. 60/116,567 filed on Jan. 21, 1999. The entire text of PCT Application Ser. No. PCT/US00/00350U.S. Provisional Application Ser. No. 60/115,143 and U.S. Provisional Application Ser. No. 60/116,567 is hereby incorporated herein by reference.

FIELD OF THE INVENTION

This invention relates to novel compositions and kits comprising (a) a bretylium cation, and (b) a facilitating anion and/or a β-receptor blocker. This invention also relates to the use of such compositions and kits to prevent and/or treat cardiovascular conditions.

BACKGROUND OF THE INVENTION

Bretylium tosylate 1 (also known as o-bromobenzylethyldimethylammonium p-toluenesulfonate) has the structure:

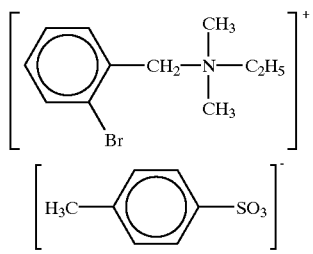

It is a known Class III antiarrhythmic agent and an adrenergic blocking agent. The bretylium cation of this compound is reported to directly modify the electrical properties of the myocardium. It also is reported to depress adrenergic neural transmission by blocking neuronal norepinephrine release and re-uptake. Bretylium tosylate consequently has been used worldwide to suppress life-threatening ventricular tachyarrhythmias, such as ventricular tachycardia and fibrillation. Bacaner (in U.S. Reissue Pat. No. 29,618) discloses suppressing cardiac ventricular fibrillation and cardiac arrhythmias generally by administering bretylium tosylate. Similarly, Bacaner (in U.S. Pat. No. 3,911,125) discloses treating angina pectoris, treating coronary insufficiency, and preventing myocardial infarction by administering bretylium tosylate.

Unformulated bretylium tosylate exhibits poor and unpredictable absorption when orally ingested. Thus, oral administration of bretylium tosylate alone is generally unsuitable for treating heart conditions and has not been approved by the FDA. Accordingly, bretylium tosylate is instead usually administered parenterally in the form of an injectable solution. This mode of administration, however, is both inconvenient and painful, particularly for chronic administration.

Administration of bretylium tosylate also can result in severely reduced ambulation in a recipient due to a sharp drop in blood pressure on assuming the upright position, resulting in dizziness and loss of consciousness. The severity of this side-effect, however, can be reduced (and the therapeutic effects of the bretylium cation can be enhanced) by administering a tricyclic anti-depressant agent (e.g., protriptyline, mazindol, amitriptyline, nortriptyline, or desipramine) with the bretylium tosylate, as disclosed by Bacaner in U.S. Pat. No. 5,036,106.

A number of studies on the bioavailability of bretylium tosylate have been described in the literature. Most these studies, however, have primarily focused on parenteral, rectal, and other non-ingested compositions comprising bretylium tosylate. Most also involve the administration of bretylium tosylate compositions under alkaline conditions.

Neubert et al. (in Ion Pair Approach of Bretylium, *Pharm. Ind.* 54, Nr. 4 (1992)) disclose a series of experiments in which bretylium tosylate was studied in the presence of saccharin, dodecylsulfate, or hexylsalicylate anions. The partition coefficients for the bretylium ion were measured in the presence of these anions using an alkaline (pH=7.2) n-octanol/buffer system and using an alkaline (pH=7.2) absorption model system employing an artificial lipid membrane. Bretylium absorption in vivo was also measured in rabbits receiving the bretylium tosylate in combination with these anions by i.v. injection (an i.v. injection of bretylium tosylate in Sorensen phosphate buffer (pH=7.2), together with an i.v. injection of hexylsalicylic acid in ethanol/Sorensen phosphate buffer (pH=7.2)) or rectal administration.

Neubert et al. (in Influence of Lipophilic Counter Ions on the Transport of Ionizable Hydrophilic Drugs, *J. Pharm. Pharmacol.* 1991, 43: 204–206) disclose a series of experiments on the influence of the counterions hydroxynaphthoate, naphthylsulphonate, adamantoate, desoxycholate, dehydrocholate, octanoate, decanoate, dodecanoate, hexadecanoate, and hexylsalicylate on the transport of bretylium using an alkaline (pH=7.2) absorption model system. It was reported that the use of hydroxynaphthoate, adamantoate, desoxycholate, or dehydrocholate counterions resulted in minimal or no increase in bretylium transport across the membrane. No therapeutic or electrophysiologic action is disclosed.

Neubert et al. (in Drug Permeation Through Artificial Lipoid Membranes, *Pharmazie* 42 (1987), H. 5) evaluated the effect of alkylated derivatives of salicylic acid, particularly hexylsalicylic acid, on the partition and transport of ionized basic drugs including bretylium tosylate using lipophilic membranes in alkaline (pH=7.2) lipoid membrane models.

Hartl et al. (in Influence of the Ion-Pair-Formation of Bretylium and Hexylsalicylic Acid on Their Influence on Blood Plasma Levels in Dogs, *Pharmazie* 45 (1990), H. 4) report an improvement in biological bretylium levels in dog plasma when a bretylium-tosylate/hexylsalicylic-acid combination was administered to dogs by i.v. injection (an i.v. injection of bretylium tosylate in Sorensen phosphate buffer (pH=7.2), together with an i.v. injection of hexylsalicylic acid in ethanol/Sorensen phosphate buffer (pH=7.2)). Hartl et al., however, do not discuss how to improve the bretylium level in the myocardium of the heart or the therapeutic effects of doing so.

Neubert et al. (in Influence of the Ion-Pair-Formation on the Pharmacokinetic Properties of Drugs (Part 4), *Pharmazie* 43 (1988), H. 12) report a series of experiments to determine the pharmacokinetic parameters of bretylium tosylate administered in combination with hexylsalicylic acid in rabbits by i.v. injection or rectally. No therapeutic or electrophysiologic action is disclosed.

Amlacher et al. (in Influence of Ion-Pair Formation on the Pharmacokinetic Properties of Drugs, *J. Pharm. Pharmacol.* 1991, 43: 794–797) disclose a series of experiments to measure the partition coefficients for the bretylium ion in the presence of salicylic acid using an alkaline (pH=7.2) n-octanol/buffer system. Bretylium absorption in vivo was also measured in rabbits receiving an i.v. injection of bretylium tosylate in Sorensen phosphate buffer (pH=7.2), together with an i.v. injection of hexylsalicylic acid in ethanol/Sorensen phosphate buffer (pH 7.2).

Neubert et al. (in Influence of the Ion-Pair-Formation on the Pharmacokinetic Properties of Drugs (Part 5), *Pharmazie* 44 (1989), H. 9) disclose a series of experiments on the effect of ion-pair formation on the elimination of bretylium and hexylsalicylic acid in rats. In these experiments, the rats received an i.v. injection of bretylium tosylate in Sorensen phosphate buffer (pH=7.2), together with an i.v. injection of hexylsalicylic acid in ethanol/Sorensen phosphate buffer (pH=7.2) and, in some instances, an oral dose of cholestyramine. Neubert et al. concluded that the pharmacokinetic parameters of bretylium were not influenced by hexylsalicylic acid.

Cho (in WO 87/05505) discloses compositions comprising particles consisting essentially of a solid emulsifying agent and a surfactant, a biologically active proteinaceous material bound to the surface of the particles, and a lipid coating surrounding such particles. While Cho is primarily directed to pharmaceutical compositions comprising insulin, he does state generally that other pharmaceutical agents, such as bretylium tosylate, could be employed. Additional ingredients in the composition are described to include, among others, sodium lauryl sulfate (as a surfactant), sodium bicarbonate, and citric acid.

Stanley et al. (in U.S. Pat. Nos. 5,288,497 and 5,288,498) disclose a dissolvable or non-dissolvable drug containing matrix form for administering a drug for absorption through the mucosal tissues of the mouth, pharynx, and esophagus. Stanley et al. identify a large group of active drugs that can be administered buccally in accordance with the invention. These references further disclose a variety of additional ingredients that can be included in the matrix including, among others, sodium lauryl sulfate and sodium dodecyl sulfate (as "permeation enhancers") and buffering systems (to adjust salival pH). Although the Stanley references list bretylium tosylate as one of the drugs that can be administered in this manner, bretylium tosylate is very bitter and too unpalatable for human consumption by this mode of administration.

Finally, Bacaner et al. (in "Synergistic Action of Bretylium With Low Doses Of Propranolol Renders The Canine Heart Virtually Invulnerable To Sustained Ventricular Fibrillation", *Circulation,* Supp. IV, page 111 (1987)) disclose a synergistic enhancement in the onset and magnitude of the antifibrillatory action caused by bretylium tosylate when a small, non-β-blocking dosage of propranolol is added to a bretylium tosylate bolus injected into dogs.

SUMMARY OF THE INVENTION

This invention provides, in part, novel pharmaceutical compositions and kits which may be administered to prevent and/or treat medical conditions related to the cardiovascular system. These compositions and kits have been found to be particularly suitable for oral administration, although they also have been found to be generally useful when administered parenterally.

Briefly, therefore, this invention is directed to pharmaceutical compositions and kits useful for preventing and/or treating a cardiovascular condition. As defined herein, the term "composition" refers to a single compound or a mixture of compounds. A "kit," in contrast, refers collectively to therapeutic ingredients which are in the form of at least two separate, discrete sources that are independently administered (whether jointly or at different times).

Some embodiments of this invention, for example, are directed to a pharmaceutical composition comprising a bretylium cation and a facilitating anion, wherein (a) the facilitating anion is less hydrophilic than a tosylate anion, (b) the pharmaceutical composition is suitable for oral ingestion, (c) the pharmaceutical composition is capable of forming a mixture comprising both the bretylium cation and the facilitating anion within the gastrointestinal tract of a subject upon ingestion by the subject, and (d) the bretylium cation and the facilitating anion together are present in the pharmaceutical composition in a therapeutically effective amount (i.e., the combination of the bretylium cation and the facilitating anion is present in the pharmaceutical composition in a therapeutically effective amount). In one embodiment of this invention, the pharmaceutical composition is identifiable by the following: when the pharmaceutical composition is orally administered to a human, the area under a plot of the bretylium cation concentration in the human's blood versus time over about 30 minutes following the oral administration is greater than the area under a plot of the bretylium cation concentration in the blood versus time over about 30 minutes following an oral administration of bretylium tosylate in an amount which supplies an equivalent amount of the bretylium cation as is supplied by the oral administration of the pharmaceutical composition. In an even more preferred embodiment, the pharmaceutical composition is identifiable by the following: when the pharmaceutical composition is orally administered to a human, the area under a plot of the bretylium cation concentration in the human's myocardium versus time over about 30 minutes following the oral administration is greater than the area under a plot of the bretylium cation concentration in the myocardium versus time over about 30 minutes following an oral administration of bretylium tosylate in an amount which supplies an equivalent amount of the bretylium cation as is supplied by the oral administration of the pharmaceutical composition.

Other embodiments of this invention are directed to a pharmaceutical kit useful for preventing and/or treating a cardiovascular condition comprising a source of a bretylium cation and a source of a facilitating anion, wherein: (a) the facilitating anion is less hydrophilic than a tosylate anion, (b) the source of the bretylium cation and the source of the facilitating anion are both suitable for oral ingestion, (c) the source of the bretylium cation and the source of the facilitating anion are capable of forming a mixture comprising both the bretylium cation and the facilitating anion within the gastrointestinal tract of a subject upon ingestion by the subject of the source of the bretylium cation and the source of the facilitating anion, and (d) the bretylium cation and the facilitating anion are present in the kit in a therapeutically effective amount (i.e., the bretylium cation and the facilitating anion are present in the kit in amounts such that their combination is therapeutically effective after both are administered). In one embodiment of this invention, the kit is identifiable by the following: when the source of the bretylium cation and the source of the facilitating anion are orally administered to a human, the area under a plot of the bretylium cation concentration in the human's blood versus time over about 30 minutes following the oral administration is greater than the area under a plot of the bretylium cation concentration in the blood versus time over about 30 minutes following an oral administration of bretylium tosylate in an amount which supplies an equivalent amount of the bretylium cation as is supplied by the oral administration of the source of the bretylium cation together with the source of the facilitating anion. In an even more preferred embodiment, the kit is identifiable by the following: when the source of the bretylium cation and the source of the facilitating anion are orally administered to a human, the area under a plot of the bretylium cation concentration in the human's myocardium versus time over about 30 minutes following the oral administration is greater than the area under a plot of the bretylium cation concentration in the myocardium versus time over about 30 minutes following an oral administration of bretylium tosylate in an amount which supplies an equivalent amount of the bretylium cation as is supplied by the oral administration of the source of the bretylium cation together with the source of the facilitating anion.

Other embodiments of this invention are directed to a pharmaceutical composition comprising a bretylium cation and a facilitating anion (or a pharmaceutical kit comprising a source of a bretylium cation and a source of a facilitating anion). In one such embodiment, the facilitating anion in this embodiment comprises an anion selected from the group consisting of:

$R^2SO_3^-$, 

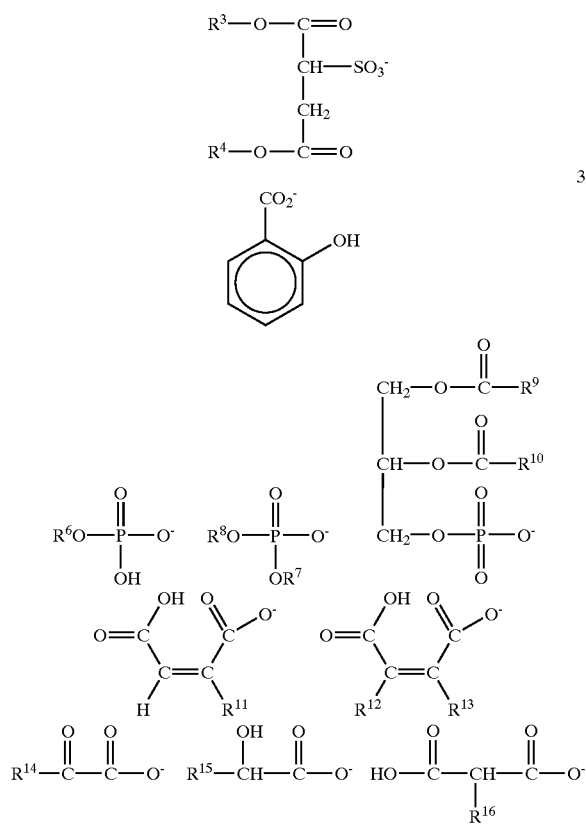

a pseudo-icosahedral carboranes anion ($CB_{11}H_{12}$), and
a substituted pseudo-icosahedral carborane anion.
Here, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, and the substituent(s) of the substituted pseudo-icosahedral carborane anion are independently hydrocarbyl or substituted hydrocarbyl; and the bretylium cation and the facilitating anion together are present in the pharmaceutical composition in a therapeutically effective amount (or, in the case of a kit, the bretylium cation and the facilitating anion are present in the kit in amounts such that their combination is therapeutically effective after both are administered).

In another embodiment directed to a pharmaceutical composition comprising a bretylium cation and a facilitating anion (or a pharmaceutical kit comprising a source of a bretylium cation and a source of a facilitating anion), the facilitating anion has the formula $R^1OSO_3^-$ wherein $R^1$ is hydrocarbyl or substituted hydrocarbyl. The pharmaceutical composition (or kit) also comprises an anti-hypotensive agent and/or a β-receptor blocker. Here, the bretylium cation, the facilitating anion, and the anti-hypotensive agent and/or the β-receptor blocker together are present in the pharmaceutical composition in a therapeutically effective amount (or, in the case of a kit, the bretylium cation, the facilitating anion, and the anti-hypotensive agent and/or the β-receptor blocker are present in the kit in amounts such that their combination is therapeutically effective after they are administered).

In another embodiment directed to a pharmaceutical composition comprising a bretylium cation and a facilitating anion (or a pharmaceutical kit comprising a source of a bretylium cation and a source of a facilitating anion), the facilitating anion has the formula:

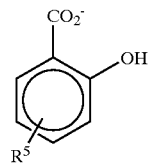

wherein $R^5$ is hydrocarbyl or substituted hydrocarbyl. The pharmaceutical composition (or kit) also comprises a neutralizing agent, an anti-hypotensive agent, and/or a β-receptor blocker. The bretylium cation; the neutralizing agent, the anti-hypotensive agent, and/or the β-receptor blocker; and the facilitating anion together are present in the pharmaceutical composition in a therapeutically effective amount (or, in the case of a kit, the bretylium cation; the neutralizing agent, the anti-hypotensive agent, and/or the β-receptor blocker; and the facilitating anion are present in the kit in amounts such that their combination is therapeutically effective after they are administered).

In another embodiment directed to a pharmaceutical composition comprising a bretylium cation and a facilitating anion (or a pharmaceutical kit comprising a source of a bretylium cation and a source of a facilitating anion), the facilitating anion has the formula:

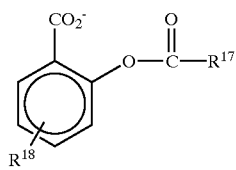

wherein $R^{17}$ is hydrocarbyl or substituted hydrocarbyl; and $R^{18}$ is hydrogen, hydrocarbyl, or substituted hydrocarbyl. Here, the bretylium cation and the facilitating anion together are present in the pharmaceutical composition in a therapeutically effective amount (or, in the case of a kit, the bretylium cation and the facilitating anion are present in the kit in amounts such that their combination is therapeutically effective after both are administered).

Other embodiments of this invention are directed to a pharmaceutical composition comprising a bretylium cation and a β-receptor blocker (or a pharmaceutical kit comprising a source of a bretylium cation and a source of a β-receptor blocker). In these embodiments, the β-receptor blocker preferably is selected from the group consisting of atenolol, esmolol, metoprolol, labetalol, talinolol, timolol, acebutolol, dichloroisoproterenol, pronethalol, sotalol, oxprenolol, alprenolol, practolol, nadolol, pindolol, penbutolol, and carvedilol. Here, the bretylium cation and the β-receptor blocker together are present in the pharmaceutical composition in a therapeutically effective amount (or, in the case of a kit, the bretylium cation and the β-receptor blocker are present in the kit in amounts such that their combination is therapeutically effective after both are administered).

This invention is also directed to safe methods for treating and/or preventing cardiovascular conditions by administering the above-summarized compositions and kits to a subject (particularly mammal subjects) in need thereof.

Other objects and features of this invention will be in part apparent and in part pointed out hereinafter.

BRIEF DESCRIPTION OF THE FIGURES

FIG. 1 is an electrocardiogram of a dog showing the effect on atrial fibrillation that was observed after administering via injection a composition containing roughly: (a) 15 mg of bretylium tosylate per kg of dog, and (b) 6.5 mg of aspirin per kg of dog.

DETAILED DESCRIPTION OF THE PREFERRED EMBODIMENTS

When conventional bretylium-containing drugs (particularly unformulated bretylium tosylate) have been administered orally, the active component of the drugs (i. e., the bretylium cation) has typically exhibited poor and/or unpredictable absorption in the gastrointestinal tract. This, along with the orthostatic hypotension side-effect of these drugs, have made oral self-administration difficult, thereby largely limiting the use of the drugs to parenteral administration in clinical emergencies when other antiarrhythmic agents have failed.

Unlike the conventionally-tried oral formulations of the bretylium cation, the pharmaceutical compositions and kits of the present invention are uniquely adapted for oral administration. In addition, they often tend to exhibit superior activity, time for onset of action, potency, safety, and/or therapeutic effectiveness relative to conventionally used bretylium-containing formulations (particularly the conventionally-tried oral formulations). In many instances, the compositions and kits of this invention are especially advantageous because they may be self-administrated as needed (for example, at a person's residence or place of work to prevent sudden cardiac death, and/or non-fatal myocardial infarction) without the assistance of a health care professional.

In accordance with the present invention, it has been discovered that the amount of the bretylium cation absorbed and/or the rate of absorption of the bretylium cation from the gastrointestinal tract (particularly the intestine) into the blood (i.e., the blood plasma or otherwise) and from the blood into the target cells can generally be improved by administering bretylium tosylate (and/or another pharmaceutically acceptable source of the bretylium cation) to a subject, along with at least one source of lipophilic or weakly hydrophilic anion (i.e., a facilitating anion), and, optionally: (i) one or more neutralizing agents (e.g., sodium bicarbonate or sodium citrate) capable of temporarily increasing the pH of the aqueous contents in the stomach, (ii) one or more anti-hypotensive agents (e.g., protriptyline), (iii) one or more buffering agents (e.g., citric acid), and/or (iv) one or more β-receptor blockers (e.g., propranolol, esmolol, and/or metoprolol). This, in turn, generally provides improved bretylium cation concentrations in the blood (and, particularly, in the myocardium) and consequent improved bretylium cation AUC (area under the curve) values for at least about 30 minutes (more preferably at least about 2 hours, even more preferably at least about 6 hours, still even more preferably at least about 12 hours, and most preferably at least about 24 hours) following oral administration relative to the conventionally-tried oral compositions (particularly unformulated bretylium tosylate), and ultimately provides an improved efficacy of the bretylium cation administered to a subject in need thereof.

The Compositions and Kits of the Present Invention

The compositions and kits of the present invention comprise (a) the bretylium cation, and (b) a facilitating anion and/or a β-receptor blocker. The more preferred compositions and kits also contain one or more neutralizing agents, buffering agents, and/or anti-hypotensive agents. Particularly preferred compositions and kits fall within one of the following categories:

(1) Compositions and kits comprising the bretylium cation, a facilitating anion, and a neutralizing agent. Here, it is especially preferred that the compositions and kits also comprise a buffering agent.

(2) Compositions and kits comprising the bretylium cation, a facilitating anion, and an anti-hypotensive agent.

(3) Compositions and kits comprising the bretylium cation, a facilitating anion, and a β-receptor blocker.

(4) Compositions and kits comprising the bretylium cation, a facilitating anion, an anti-hypotensive agent, and a β-receptor blocker.

(5) Compositions and kits comprising the bretylium cation, a facilitating anion, a neutralizing agent, and an anti-hypotensive agent. Here, it is especially preferred for the compositions and kits to also comprise a buffering agent.

(6) Compositions and kits comprising the bretylium cation, a facilitating anion, a neutralizing agent, and a β-receptor blocker. Here, it is especially preferred for the compositions and kits to also comprise a buffering agent.

(7) Compositions and kits comprising the bretylium cation, a facilitating anion, a neutralizing agent, an anti-hypotensive agent, and a β-receptor blocker. Here, it is especially preferred for the compositions and kits to also comprise a buffering agent.

(8) Compositions and kits comprising the bretylium cation and aspirin (i.e., "acetylsalicylic acid").

(9) Compositions and kits comprising the bretylium cation and at least one β-receptor blocker (particularly atenolol, esmolol, metoprolol, labetalol, talinolol, timolol, acebutolol, dichloroisoproterenol, pronethalol, sotalol, oxprenolol, alprenolol, practolol, nadolol, pindolol, penbutolol, or carvedilol).

A. Source of the Bretylium Cations

The compositions and kits of this invention may contain the bretylium cation in the form of a pharmaceutically acceptable material that either comprises the bretylium cation itself or is capable of forming the bretylium cation after being administered to the intended recipient (and, consequently, when a composition or kit is referred to herein as comprising the bretylium cation, it should be understood that the composition or kit may either comprise the bretylium cation itself or be capable of forming the bretylium cation after being administered to the intended recipient). Thus, for example, when intended for oral administration, the pharmaceutically acceptable material should release the bretylium cation into the aqueous contents of the gastrointestinal tract. Suitable materials include, for example, pharmaceutically acceptable salts of the bretylium cation (e.g., bretylium tosylate, bretylium di(2-ethylhexyl) sulfosuccinate, or bretylium salicylate), and solutions or suspensions comprising the bretylium cation. Pharmaceutical grade bretylium tosylate is commercially available from, for example, Ganes Chemicals, Inc., Carlstadt, N.J. Alternatively, bretylium tosylate may be prepared, for example, by reacting o-bromobenzylethylmethylamine with methyl tosylate, as discussed in U.S. Pat. No. 3,038,004. When the material is a pharmaceutically acceptable salt other than bretylium tosylate, the counterion of the salt preferably has little or no tendency to form a covalent compound with the bretylium cation. Such salts may be prepared, for example, by using a conventional double displacement reaction, wherein a bretylium salt (e.g., bretylium tosylate) is reacted with a suitable acid or alkali metal salt (preferably a sodium salt) of the desired anion. Bretylium-cation-containing materials, which have been approved by the Food and Drug Administration for use in other medicines or foods, are generally most preferred.

B. Source of the Facilitating Anion

The compositions and kits of this invention may contain the facilitating anion in the form of a pharmaceutically acceptable material that either comprises the facilitating anion itself or is capable of forming the facilitating anion after being administered to the intended recipient (and, consequently, when a composition or kit is referred to herein as comprising a facilitating anion, it should be understood that the composition or kit may either comprise the facilitating anion itself or be capable of forming the facilitating anion after being administered to the intended recipient). It is preferred that the facilitating anion have a weak affinity for water, and it is particularly preferred for the facilitating anion to be less hydrophilic than the tosylate anion. Such an anion, when ingested with the bretylium cation, tends to form bretylium-cation/facilitating-anion combinations capable of, for example, crossing the lipid phase boundary of the gastrointestinal tract and entering the recipient's blood, and crossing the lipid barriers of the capillary membranes and myocardial cell membranes of the heart. Preferably, the facilitating anion forms bretylium-cation/facilitating-anion combinations that carry a charge that is neutral or substantially neutral. The facilitating anion also preferably forms such combinations that are more lipophilic (or less hydrophilic) than bretylium tosylate. Facilitating-anion-containing materials, which have been approved by the Food and Drug Administration for use in other medicines or foods, are generally most preferred.

It is particularly preferred for the facilitating anion to have at least one of the following features:

(1) The facilitating anion is the conjugate base of an acid having a $pK_a$ value of less than about 5, more preferably less than about 4, and still more preferably less than about 3. Where a neutralizing agent is not administered, it is preferred for the facilitating anion to be the conjugate base of an acid having a $pK_a$ value of less than about 1, more preferably less than about 0, and still more preferably less than about −1. Although the $pK_a$ values associated with suitable facilitating anions may be less than about −10, most suitable facilitating anions will have a $pK_a$ value of at least about −10.

(2) The facilitating anion has a well-distributed charge to reduce its hydrophilicity. A particularly preferred example of such an anion is the salicylate anion.

(3) The facilitating anion comprises at least one alkyl group that comprises at least 10 carbon atoms. A preferred example of such an anion is the dodecylsulfate anion.

(4) The facilitating anion has an organic/aqueous phase distribution constant ("K") that is greater than the organic/aqueous phase distribution constant associated with the tosylate anion (i.e., greater than about 320). In a particularly preferred embodiment, the facilitating anion has a K value which is greater than about 500, more preferably greater than about 700, still more preferably greater than about 800, and still even more preferably greater than about 1000. Although the K values associated with suitable facilitating anions may be greater than about $10^6$, the most suitable facilitating anions have a K value which is less than about $10^6$. To determine the K value for a particular anion, a small amount of methyltridecylammonium chloride ("$Q^+Cl^-$") and a small amount of the methyltridecylammonium salt of the anion ("$Q^+X^-$") are added to a mixture of water and 1-decanol. The mixture is allowed to separate, and the concentrations of the chloride ion and the anion in each phase are then measured. The K value is calculated using the formula: K=[X⁻, dec.][Cl⁻, aq.]/[X⁻, aq.][Cl⁻, dec.], wherein the quantities in brackets are concentrations. The K value for the salicylate anion, for example, is reported to be greater than 1000. A more extensive discussion of the procedure for determining K values can be found in, for example, C. J. Coetzee and H. Freisee, *Anal. Chem.*, Vol. 41, Page 1128 (1969) (incorporated herein by reference).

Examples of suitable facilitating anions include, but are not limited to, the following:

$R^1OSO_3^-$,
$R^2SO_3^-$,

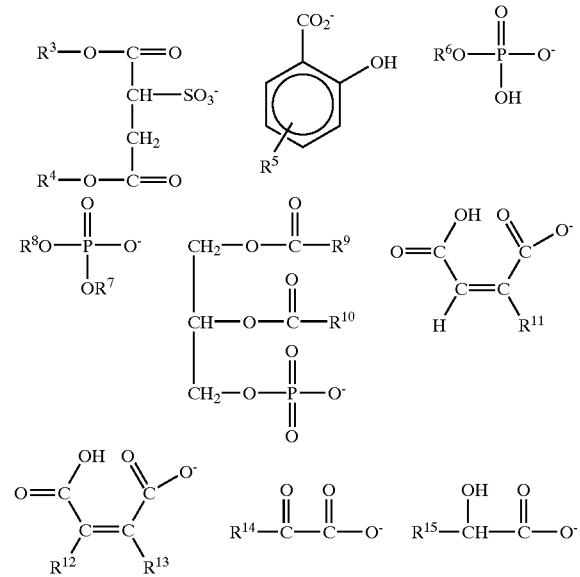

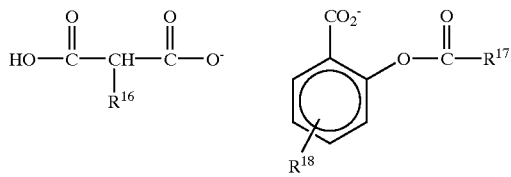

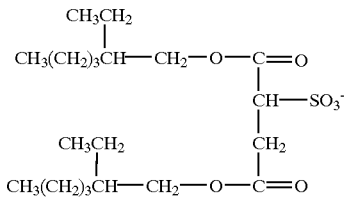
2

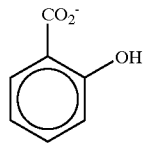
3

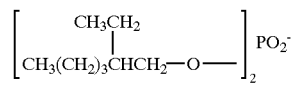
4

$CH_3(CH_2)_{10}CH_2OSO_3^-$
5

$CH_3(CH_2)_{14}CH_2SO_3^-$
6

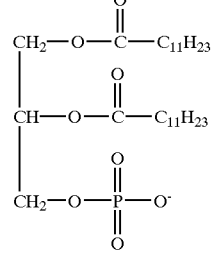
7 a pseudo-icosahedral carboranes anion ($CB_{11}H_{12}^-$), and a substituted pseudo-icosahedral carborane anion.

In the above-formulas, $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and the substituent (or substituents) of the substituted pseudo-icosahedral carborane anion are independently hydrocarbyl or substituted hydrocarbyl; and $R^5$ and $R^{18}$ are independently hydrogen, hydrocarbyl, or substituted hydrocarbyl. In a particularly preferred embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and the substituent (or substituents) of the substituted pseudo-icosahedral carborane anion are independently hydrocarbyl; and $R^{18}$ is hydrogen. In such an embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and the substituent (or substituents) of the substituted pseudo-icosahedral carborane anion are preferably independently selected from the group consisting of alkyl, alkenyl, alkynyl, cycloalkyl, cycloalkenyl, aryl, arylalkyl, arylalkenyl, or arylalkynyl. The preferred aryl is phenyl. The aryl moiety may be unsubstituted or substituted with one or more radicals selected from the group consisting of alkyl, alkenyl, alkynyl, cycloalkyl, and cycloalkenyl.

In a preferred embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and the substituent (or substituents) of the substituted pseudo-icosahedral carborane anion are independently a residue of a fatty acid formed by removing a carboxylic acid group from the fatty acid.

In another preferred embodiment, the facilitating anion comprises an anion selected from the group consisting of ($C_{10}$–$C_{30}$)alkylsulfate anions, ($C_{10}$–$C_{30}$)alkylsulfonate anions, ($C_6$–$C_{12}$)alkylsulfosuccinate anions, salicylate anions, ($C_1$–$C_{30}$)alkylsalicylate anions, ($C_{10}$–$C_{30}$) alkylphosphate anions, di($C_8$–$C_{12}$)alkylphosphate anions, di($C_{10}$–$C_{30}$)alkanoylphosphatidate anions, ($C_8$–$C_{22}$) alkylmaleate anions, di($C_4$–$C_{12}$)alkylmaleate anions, α-keto ($C_9$–$C_{21}$)carboxylate anions, α-hydroxy ($C_9$–$C_{21}$) carboxylate anions, ($C_{12}$–$C_{22}$)alkylmalonate anions, and ($C_1$–$C_{18}$)alkylpseudo-icosahedral carborane anions.

Still more preferably, the facilitating anion comprises an anion selected from the group consisting of ($C_{10}$–$C_{30}$) alkylsulfate anions, ($C_{10}$–$C_{30}$)alkylsulfonate anions, ($C_6$–$C_{12}$)alkylsulfosuccinate anions, salicylate anions, ($C_{10}$–$C_{30}$)alkylphosphate anions, di($C_8$–$C_{12}$)alkylphosphate anions, and di($C_8$–$C_{22}$)alkanoylphosphatidate anions.

Still even more preferred facilitating anions comprise an anion selected from the group consisting of the di(2-ethylhexyl)sulfosuccinate anion 2; the salicylate anion 3; the di(2-ethylhexyl) phosphate anion 4; the lauryl sulfate anion 5; the hexadecylsulfonate anion 6; the dipalmitoyl phosphatidate anion 7; and the acetylsalicylate anion 8:

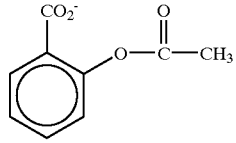
8

In a particularly preferred embodiment, the facilitating anion is the di(2-ethylhexyl)sulfosuccinate anion 2. In another particularly preferred embodiment, the facilitating anion is the salicylate anion 3. In yet another particularly preferred embodiment, the facilitating anion is the lauryl sulfate anion 5. In still a further particularly preferred embodiment, the facilitating anion is the acetylsalicylate anion 8. It has been found in accordance with this invention that these anions (and especially the salicylate anion, the lauryl sulfate anion, and the acetylsalicylate anion), in general, tend to synergistically enhance the therapeutic effects of the bretylium cation by, for example, synergistically increasing the ventricular fibrillation threshold and synergistically prolonging the effective ventricular refractory period.

In one of the most preferred embodiments, the pharmaceutical composition or kit contains aspirin (i.e., the acetylsalicylate anion). One reason for this particular preference stems from the fact that aspirin—in addition to synergistically enhancing the effects of the bretylium cation—reduces or entirely blocks platelet aggregation (a common cause of cardiac complications).

When intended for oral administration, the source of the facilitating anion preferably is a pharmaceutically acceptable material that releases the facilitating anion into the aqueous contents of the gastrointestinal tract. Non-limiting examples suitable facilitating anion sources include the pharmaceutically acceptable salts of the facilitating anion (e.g., the alkali metal salts, particularly the sodium salts, of the facilitating anion), and solutions or suspensions comprising the facilitating anion. When the source is a salt, the counterion paired with the facilitating anion preferably has little or no tendency to form a covalent compound with the facilitating anion. Such salts may be prepared by conventional means from the conjugate acid of the facilitating anion (e.g., reacting an appropriate base with the conjugate acid).

Sodium di(2-ethylhexyl)sulfosuccinate is commercially available from Aldrich Chemical Co., Milwaukee, Wis. Potassium di(2-ethylhexyl)sulfosuccinate can be prepared from the sodium salt by recrystallization from aqueous solution in the presence of an excess of potassium chloride.

Salicylic acid and sodium salicylate are both commercially available from Aldrich Chemical Co. Potassium salicylate can be prepared by treating a hot, concentrated solution of salicylic acid with an equivalent amount of potassium hydroxide, preferably as a concentrated solution, and then cooling to separate potassium salicylate.

Sodium dodecylsulfate is commercially available from Aldrich Chemical Co. Potassium dodecylsulfate can be prepared by recrystallizing the sodium salt in the presence of an excess of potassium chloride.

Di(2-ethylhexyl)phosphoric acid is commercially available from Aldrich Chemical Co. Sodium di(2-ethylhexyl) phosphate can be prepared by treating a toluene solution of the acid with a small excess of sodium hydroxide as an aqueous solution. A 2-phase system results, with the sodium salt in the toluene phase. Separation of the phases followed by distillation of the toluene yields a residue that is sodium di(2-ethylhexyl)phosphate. The potassium salt is obtained analogously, except that a potassium hydroxide solution is used in the place of the sodium hydroxide solution.

1-Hexadecylsulfonic acid sodium salt is commercially available from Aldrich Chemical Co. Potassium 1-hexadecylsulfonate can be obtained from the sodium salt by recrystallization in the presence of a small excess of potassium chloride.

Sodium salts of phosphatidic acids are commercially available from Avanti Polar Lipids, Alabaster, Ala.

It should be recognized that the compositions, kits, and methods of the present invention are not limited to the use of a single type of facilitating anion. If necessary or desirable, 2 or more different types of facilitating anions can be used.

It should also be recognized that the bretylium cation and the facilitating anion can be from the same compound or from different compounds. For example, the source of the bretylium cation and the source of the facilitating anion may be a single compound comprising the bretylium cation and the facilitating anion, such as a pharmaceutically acceptable salt wherein the bretylium cation is paired with the facilitating anion. Such compounds include, for example, bretylium di(2-ethylhexyl)sulfosuccinate, bretylium salicylate, bretylium di(2-ethylhexyl) phosphate, bretylium lauryl sulfate, and bretylium hexadecylsulfonate.

C. β-Receptor Blocker

The compositions and kits of the present invention may contain one or more pharmaceutically acceptable β-receptor blockers (preferably, a β-receptor blocker that does not antagonize the therapeutic effect of the bretylium cation). It has been found in accordance with this invention that a β-receptor blocker often produces a synergistic improvement in the therapeutic effect of the bretylium cation. For example, a β-receptor blocker tends to (1) synergistically increase the rate at which the bretylium cation effects anti-fibrillatory action, and/or (2) synergistically enhance the bretylium cation's anti-fibrillatory action.

Suitable β-receptor blockers generally include, but are not limited to, propranolol (also known as "Inderal"), atenolol, esmolol, metoprolol, labetalol, talinolol, timolol, acebutolol, dichloroisoproterenol, pronethalol, sotalol, oxprenolol, alprenolol, practolol, nadolol, pindolol, penbutolol, and carvedilol. Preferably, the β-receptor blocker is propranolol, atenolol, esmolol, metoprolol, talinolol, timolol, or acebutolol. In one particularly preferred embodiment, the β-receptor blocker comprises propranolol. In another particularly preferred embodiment, the β-receptor blocker comprises esmolol (particularly in instances where the composition is being administered via injection and/or the facilitating anion is lauryl sulfate, sulfosuccinate, or salicylate). In yet a further particularly preferred embodiment, the β-receptor blocker comprises metoprolol.

Propranolol is commercially available from, for example, Wyeth-Ayerst Laboratories, Philadelphia, Pa. Atenolol is commercially available from, for example, Zeneca Pharmaceuticals, Wilmington, Del. Esmolol is commercially available from, for example, Baxter Healthcare Corp., Deerfield, Ill. Metoprolol is commercially available from, for example, Novartis, East Hanover, N.J. Labetalol is commercially available from, for example, Schering-Plough Pharmaceuticals, Madison, N.J. Acebutolol is commercially available from, for example, Wyeth-Ayerst Laboratories. Carvedilol is commercially available from, for example, SmithKline Beecham, Philadelphia, Pa. Sotalol is commercially available from, for example, Berlex Laboratories, Inc., Wayne, N.J. Nadolol is commercially available from, for example, Bristol-Myers Squibb Co., Stamford, Conn.

D. Neutralizing Agent

The compositions and kits of the present invention (particularly those intended to be orally administered) may optionally contain one or more neutralizing agents. The neutralizing agent may be any pharmaceutically acceptable material that increases the pH of the stomach when ingested, and that is chemically compatible with the bretylium cation and the facilitating anion selected. Preferably, the neutralizing agent is physiologically inert other than for pH adjustment purposes, and is not absorbed or only minimally absorbed from the gastrointestinal tract. Examples of particularly preferred neutralizing agents are those selected from the group consisting of pharmaceutically acceptable alkali metal carbonates (e.g., sodium bicarbonate or potassium hydrogen carbonate); alkali metal citrates (e.g., sodium citrate); alkali metal phosphates; alkali metal salts of carboxylic acids (e.g., alkali metal salts of acetic acid, tartaric acid or succinic acid); alkaline earth metal hydroxides (e.g., magnesium hydroxide); and mono-, di-, and polyaminosugars (e.g., meglamine). In one of the more preferred embodiments, the neutralizing agent comprises sodium bicarbonate (for example, commercially available Alka Seltzer), which is non-toxic and has a lower equivalent weight than most other suitable neutralizing agents.

A neutralizing agent permits the use of a broader class of facilitating anions. More specifically, because the preferred facilitating anions are conjugate bases of acids having a $pK_a$ value lower than or equal to the ambient pH of the stomach, temporarily increasing this pH in a subject by ingestion of the neutralizing agent expands the range of suitable facilitating anions. When a neutralizing agent is employed, the facilitating anion selected preferably is the conjugate base of an acid having a $pK_a$ value at least about one unit less than the ambient pH as adjusted by the neutralizing agent, more preferably having a $pK_a$ value at least about 1.5 units less than the ambient pH as adjusted by the neutralizing agent, and still more preferably having a $pK_a$ value at least about 2 units less than the ambient pH as adjusted by the neutralizing agent.

E. Buffering Agent

The composition and kits of the present invention (particularly those intended for oral administration, and even more particularly those containing a neutralizing agent) may optionally contain one or more buffering agents to prevent an excessive increase in the pH of the aqueous contents of the stomach resulting from ingestion of the neutralizing agent. The buffering agent may be any pharmaceutically acceptable buffering agent. Suitable buffering agents include, but are not limited to, pharmaceutically acceptable acids (e.g., citric acid). In a particularly preferred embodiment, the buffering agent is a pharmaceutically acceptable acid having a $pK_a$ value of at least about 1 unit (and more preferably at least about 2 units) greater than the $pk_a$ value of the conjugate acid of the facilitating anion selected. Even more preferably, the buffering agent is an acid having a $pK_a$ value of from about 4.5 to about 5.5.

F. Anti-hypotensive Agent

The compositions and kits of the present invention may optionally contain one or more pharmaceutically-acceptable anti-hypotensive agents, which reduce or eliminate orthostatic hypotension caused by the bretylium cation. The anti-hypotensive agent preferably operates to reduce or eliminate the orthostatic hypotension by blocking the uptake of bretylium cations into the sympathetic nerves. Suitable anti-hypotensive agents include, but are not limited to, the tricyclic anti-depressant compounds selected from the group consisting of protriptyline, mazindol, amitriptyline, nortriptyline, desipramine, with protriptyline being especially preferred. Protriptyline is commercially available from, for example, Sidmak Labs, Inc., East Hanover, N.J.

In a particularly preferred embodiment, the anti-hypotensive agent(s) also enhances the therapeutic effect of the bretylium cation of, for example, raising the electrical ventricular fibrillation threshold (this effect being in addition to the effect of reducing or eliminating orthostatic hypotension caused by the bretylium cation). Anti-hypotensive agents, particularly the tricyclic anti-depressant compounds discussed above, often synergize the therapeutic effect of the bretylium cation, thereby lowering the dose of the bretylium cation needed, for example, to suppress ventricular tachyarrhythmias.

Ephedrine, a synthetic sympathomimetic adrenergic drug, may also be used to reverse orthostatic hypotension.

Form of Pharmaceutical Compositions

The pharmaceutical compositions of the present invention comprise (a) the bretylium cation, and (b) a facilitating anion and/or a β-receptor blocker. They may also comprise one or more non-toxic, pharmaceutically-acceptable carriers, excipients, and/or adjuvants (collectively referred to herein as "carrier materials"). The pharmaceutical compositions of the present invention may be adapted for administration by any suitable route by selection of appropriate carrier materials and a dosage of the bretylium cation effective for the intended treatment.

The techniques used to prepare the pharmaceutical compositions of this invention vary widely, and include the well known techniques of pharmacy for admixing the components of a medicine composition. In general, the compositions are prepared by uniformly and intimately admixing the active compounds (in the form of, for example, powders) with or without a liquid or finely divided solid carrier, or both, and then, if necessary, encapsulating or shaping the product. For example, a tablet may be prepared by compressing or molding a powder or granules of the compound, optionally with one or more accessory ingredients. Compressed tablets may be prepared by compressing, in a suitable machine, the compound in a free-flowing form, such as a powder or granules optionally mixed with a binding agent, lubricant, inert diluent, and/or surface active/dispersing agent(s). Molded tablets can be made by molding, in a suitable machine, the powdered compound moistened with an inert liquid diluent.

In a particularly preferred embodiment, the composition is intended to be administered orally. In this instance, the carrier material(s) may be solid and/or liquid. Preferably, such a composition is formulated as a unit-dose composition, i.e., the pharmaceutical composition contains a desired specific amount of the bretylium cation and the facilitating anion, and is in the form of, for example, a tablet (with or without a coating), a hard or soft capsule, a lozenge, a cachet, a dispensable powder, granules, a suspension, an elixir, a liquid, or any other form reasonably-adapted for oral administration. Liquid dosage forms for oral administration include, for example, pharmaceutically acceptable emulsions, solutions, suspensions, syrups, and elixirs containing inert diluents commonly used in the art, such as water. Such compositions may also comprise, for example, wetting agents; emulsifying and suspending agents; and sweetening, flavoring, and perfuming agents. An excellent source which discusses in detail methods for preparing oral compositions (both solid and liquid) is *Pharmaceutical Dosage Forms: Tablets, Second Edition, Revised and Expanded,* Vol. 1–3 (ed. by Lieberman, H. A., Lachman, L., & Schwartz, J. B., Marcel Dekker, Inc., 270 Madison Ave, New York, N.Y. 1989) and *Pharmaceutical Dosage Forms: Disperse Systems,* Vol. 1–2 (ed. by Lieberman, H. A., Rieger, M. M., & Banker, G. S., Marcel Dekker, Inc., 270 Madison Ave, New York, N.Y. 1989).

The following discussion describes some of the more typical types of carrier materials that may be used in accordance with this invention. It should be recognized, however, that other carrier materials (such as colorants, flavors, sweeteners, and preservatives) are known in the pharmaceutical art, and may be used in the preparation of the pharmaceutical compositions of the present invention.

A. Diluents

The pharmaceutical compositions of the present invention may optionally comprise one or more pharmaceutically-acceptable diluents. Examples of suitable diluents include, either individually or in combination: lactose USP; lactose USP, anhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates, NF (e.g., Emdex); Celutab; dextrose (e.g., Cerelose); inositol; hydrolyzed cereal solids such as the Maltrons and Mor-Rex; amylose; Rexcel; powdered cellulose (e.g., Elcema); calcium carbonate; glycine; bentonite; polyvinylpyrrolidone; and the like.

B. Disintegrants

The pharmaceutical compositions of the present invention may optionally comprise one or more pharmaceutically-acceptable disintegrants, particularly for tablet formulations. Examples of suitable disintegrants include, either individually or in combination: starches; sodium starch glycolate; clays (such as Veegum HV); celluloses and various modifications of celluloses (such as purified cellulose, methylcellulose and sodium carboxymethylcellulose, and carboxymethylcellulose); alginates; pregelatinized corn starches (such as National 1551 and National 1550); Crospovidone, USP NF; gums (such as agar, guar, locust bean, Karaya, pectin, tragacanth); and the like.

C. Binding Agents and Adhesives

The pharmaceutical compositions of the present invention may optionally contain one or more binding agents or adhesives, particularly for tablet formulations. Such a binding agent or adhesive preferably imparts sufficient cohesion to the powders to allow for normal processing, such as sizing, lubrication, compression and packaging, while also allowing the tablet to disintegrate and the composition to dissolve upon ingestion. Examples of suitable binding agents and adhesives include, either individually or in combination: acacia; tragacanth; sucrose; gelatin; glucose; starch; cellulose materials (e.g., methylcellulose and sodium carboxymethylcellulose (e.g., Tylose)); alginic acid and salts of alginic acid; magnesium aluminum silicate; polyethylene glycol; guar gum; polysaccharide acids; bentonites; polyvinylpyrrolidone; polymethacrylates; hydroxypropylmcthylcellulose (HPMC); hydroxypropylcellulose (Klucel); ethylcellulose (Ethocel); pregelatinized starch (e.g., National 1511 and Starch 1500); and the like.

D. Wetting Agents

The pharmaceutical compositions of the present invention may optionally contain one or more pharmaceutically-acceptable wetting agents. Such wetting agents preferably maintain the bretylium cation, and, where desired, other ingredients of the composition in suspension, and improve the relative bioavailability of the pharmaceutical composition. Examples of suitable wetting agents include, either individually or in combination: oleic acid; glyceryl monostearate; sorbitan mono-oleate; sorbitan monolaurate; triethanolamine oleate; polyoxyethylene sorbitan mono-oleate; polyoxyethylene sorbitan monolaurate; sodium oleate; sodium lauryl sulfate; and the like.

E. Lubricants

The pharmaceutical compositions of the present invention may optionally contain one or more pharmaceutically-acceptable lubricants. The lubricant preferably (1) imparts a surface to the composition (e.g., in the form of a tablet or capsule) that allows simple removal of the composition from a mold, and/or (2) increases the ability of the components of the composition to be mixed evenly and readily. Examples of suitable lubricants include, either individually or in combination: glyceryl behapate (Compritol 888); stearates (magnesium, calcium, sodium); stearic acid; hydrogenated vegetable oils (e.g., Sterotex); talc; waxes; Stearowet; boric acid; sodium benzoate and sodium acetate; sodium fumarate; sodium chloride; DL-Leucine; polyethylene glycols (e.g., Carbowax 4000 and Carbowax 6000); sodium oleate; sodium benzoate; sodium acetate; sodium lauryl sulfate; magnesium lauryl sulfate; and the like.

F. Anti-Adherent Agents and Glidants

The pharmaceutical compositions of the present invention optionally may comprise one or more anti-adherent agents and/or glidants. Examples of suitable anti-adherents and glidants include, either individually or in combination: talc; cornstarch, Cab-O-Sil, Syloid, DL-Leucine, sodium lauryl sulfate, metallic stearates, and the like.

G. Enteric Coatings

In a particularly preferred embodiment, the pharmaceutical composition is in an enteric form, i.e., the pharmaceutical composition comprises a coating which is resistant to degradation in the stomach, but will decompose in the intestinal tract. In such an instance, the pharmaceutical composition is typically in the form of a tablet or capsule. Enteric coating materials are well-known in the art. For example:

1. In U.S. Pat. No. 4,849,227, Cho describes enteric coatings containing: hydroxypropyl methylcellulose phthalate, polyethylene glycol-6000, and/or shellac.

2. In U.S. Pat. No. 5,814,336, Kelm et al. describe polymer enteric coatings having a thickness of at least about 250 $\mu$m, and containing a polyanionic polymer that is insoluble in water and aqueous solutions having a pH of less than about 5 to about 6.3. Examples of coating materials that Kelm et al. report to be suitable are cellulose acetate phthalate, cellulose acetate trimelliate, hydroxypropyl methylcellulose phthalate, hydroxypropyl methyl cellulose acetate succinate, polyvinyl acetate phthalate, poly(methacrylic acid, methyl methacrylate) 1:1, poly(methacrylic acid, ethyl acrylate) 1:1, and compatible mixtures thereof.

3. In U.S. Pat. No. 5,914,132, Kelm et al. disclose a multilayered polymer enteric coating to prevent the release of an active ingredient until near the junction between the small intestine and the colon (or while in the colon). This multilayered coating has (1) an outer layer which has a thickness of from about 20 to about 50 $\mu$m, and begins to dissolve at a pH of between about 6.8 and about 7.2; and (2) an inner layer which has a thickness of roughly from about 90 to about 300 $\mu$m, and begins to dissolve at a pH of between about 5 and 6.3. Examples of coating materials that Kelm et al. report to be suitable for the outer coating are poly (methacrylic acid, methyl methacrylate) 1:2, and mixtures of poly(methacrylic acid, methyl methacrylate) 1:1 and poly(methacrylic acid, methyl methacrylate) 1:2 in a ratio of about 1:10 to about 1:2. Examples of coating materials that Kelm et al. report to be suitable for the inner coating are the same as those described as being suitable coatings in U.S. Pat. No. 5,814,336.

4. In U.S. Pat. No. 5,733,575, Mehra et al. describe enteric coatings made of titanized polyvinyl acetate phthalate, polyvinyl acetate phthalate which has been jet milled, hydroxypropyl methylcellulose phthalate, hydroxypropyl methylcellulose acetate succinate, or cellulose acetate phthalate.

See also, e.g., Shaffer et al., U.S. Pat. No. 4,147,768; Maruyama et al., U.S. Pat. No. 5,750,148; Kukubo et al., U.S. Pat. No. 5,776,501; and Gardner et al., U.S. Pat. No. 5,980,951.

H. Injectable Compositions

The compositions of this invention are generally not limited to being used orally. In general, they also may be administered by injection (intravenous, intramuscular, subcutaneous, or jet) if desired. Such injectable compositions may employ, for example, saline, dextrose, or water as a suitable carrier material. The pH of the composition may be adjusted, if necessary, with a suitable acid, base, or buffer. Suitable bulking, dispersing, wetting, or suspending agents (e.g., mannitol and polyethylene glycol (such as PEG 400)), may also be included in the composition. A suitable parenteral composition can also include eplerenone in injection vials. Aqueous solutions can be added to dissolve the composition before injection. The compositions of this invention may also be contained in pre-filled syringes for emergency use.

An excellent source which discusses in detail methods for preparing injectable compositions is *Pharmaceutical Dosage Forms: Parenteral Medications,* Vol. 1–2 (ed. by Avis, K. E., Lachman, L., & Lieberman, H. A., Marcel Dekker, Inc., 270 Madison Ave, New York, N.Y. 1989).

Utility of the Compositions and Kits of the Present Invention

The compositions and kits of the present invention are useful for, but not limited to, treating conditions (i.e., medical disorders or otherwise) which have conventionally been treated by administering the bretylium cation (particularly in the form of bretylium tosylate injectable compositions). In general, the compositions and kits are useful where it is desirable to accomplish one or more of the following:

1. Prevent sudden cardiac death.
2. Prevent and/or treat myocardial infarction.
3. Prevent and/or treat congestive heart failure (particularly by inducing sympathetic blockade), such as by reducing oxidative metalobism in the heart by blocking norepinephrine release.
4. Prevent and/or treat ventricular fibrillation (particularly by raising the ventricular fibrillation threshold).
5. Prevent and/or treat ventricular arrhythmia in general.
6. Prevent and/or treat ventricular tachyeardia.
7. Prevent and/or treat ventricular premature heatbeats.
8. Prevent and/or treat atrioventricular dissociation.
9. Prevent and/or treat multifocal ectopic beats.
10. Prevent and/or treat premature ventricular extrasystoles.
11. Prevent and/or treat bigeminal rhythm.
12. Prevent and/or treat trigeminal rhythm.
13. Prevent and/or treat angina pectoris (most notably by sympathetic blockade).
14. Prevent and/or treat coronary insufficiency (most notably by sympathetic blockade).
15. Prevent and/or treat sympathetically induced pain, such as with causalgia.
16. Restore and/or maintain normal sinus rhythm.
17. Increase the effective ventricular refractory period.
18. Increase the sinus automaticity transiently.
19. Prolong the Purkinje action potential duration.
20. Induce post-ganglionic sympathetic blockade, thereby reducing oxidative metabolism in the heart, reducing the heart rate, and reducing the blood pressure.
21. Block the sympathetic nervous system, typically by blocking the release of norepinephrine at sympathetic nerve endings or ganglia, and/or by blocking β-receptors.
22. Reduce vascular impedance, and, in particular, reduce coronary resistance.
23. Increase the ventricular fibrillation threshold.
24. Prolong the action potential duration of cardiac cells.

The pharmaceutical compositions and kits of the present invention are particularly advantageous because they generally act in 2 separate ways to treat cardiovascular conditions: (1) they have an anti-fibrillatory effect (i.e., it is believed that they directly act on the ionic currents in the myocardial heart cells to prevent and/or treat fibrillation), and (2) they have a sympathetic nervous system blocking effect (i.e., it is believed that they block the release of the nerve transmitter norepinephrine from the sympathetic ganglia and nerve endings, thereby reducing or entirely eliminating the coronary artery constriction, platelet aggregation, and/or oxygen waste normally caused by the release of the nerve transmitter).

It also has been discovered in accordance with this invention that the compositions and kits of this invention (particularly those comprising a source of the salicylate anion, and most preferably those comprising aspirin) may be used to prevent and/or treat atrial arrhythmia, most notably atrial fibrillation (as well as atrial tachycardia). Atrial fibrillation is reported to be probably the most common cardiac arrhythmia. Although it is often not a life-threatening arrhythmia, atrial fibrillation is believed to be associated with strokes caused by blood clots forming in areas of stagnant blood collected in the non-contracting atrium as a result of the atrial fibrillation. Atrial fibrillation also is associated with loss of the atrial-ventricular synchrony, and therefore can result in an irregular heart rate and/or a hemodynamically inefficient cardiac performance. In addition, atrial fibrillation may cause, for example, palpitations of the heart, dyspnea (i.e., difficulty in breathing), fatigue, angina pectoris (i.e., pain in the region of the heart), dizziness, or even loss of consciousness. Thus, the use of the compositions and kits of the present invention to prevent and/or treat atrial arrhythmias can ultimately offer several benefits by reducing or eliminating one or more of these conditions. And, the compositions and kits of the present invention may be used without causing the trauma normally associated with many conventionally used techniques for converting atrial fibrillation to sinus rhythm (most notably, shocking the chest wall or implantation of an atrial defibrillator).

It should be recognized that the compositions and kits of this invention may be used in conjunction with or to completely replace other antiarrhythmic agents, adrenergic neuronal blocking agents (e.g., lidocaine), and/or therapeutic agents useful for the treatment of congestive heart failure (e.g., ACE inhibitors and/or digitalis).

It should further be recognized that these compositions and kits are useful for human treatment, as well as veterinary treatment of companion animals, exotic animals, and farm animals. More preferred recipients include mammals, particularly humans, horses, dogs, and cats.

Dosages

A. The Bretylium Cation

The pharmaceutical compositions and kits of the present invention preferably contain the bretylium cation in an amount sufficient to administer from about 0.1 to about 3000 mg (more preferably from about 20 to about 1600 mg, and still more preferably from about 40 to about 1000 mg) of the bretylium cation. When the source of the bretylium cation is bretylium tosylate, the pharmaceutical composition or kit preferably contains from about 0.2 to about 5000 mg (more preferably from about 40 to about 2500 mg, and still more preferably from about 80 to about 2000 mg) of bretylium tosylate.

A daily dose of the pharmaceutical composition or kit preferably administers an amount of the bretylium cation sufficient to provide from about 0.001 to about 50 mg (more preferably from about 0.6 to about 18 mg, and still more preferably from about 1 to about 18 mg) of the bretylium cation per kg of the recipient's body weight per day. When the source of the bretylium cation is bretylium tosylate, a daily dose of the pharmaceutical composition or kit preferably administers from about 0.002 to about 50 mg (more preferably from about 1 to about 30 mg, and still more preferably from about 2 to about 30 mg) of bretylium tosylate per kg of the recipient's body weight per day.

It should be recognized that the preferred daily dose of the bretylium cation will depend on various factors. One such factor is the specific condition being treated. For example, the preferred daily dose of the bretylium cation for an anti-infarction therapeutic effect is from about 1.0 to about 5.0 mg/kg body weight per day, while the preferred daily dose for an anti-fibrillary therapeutic effect is from about 5.0 to about 30.0 mg/kg body weight per day, and the preferred daily dose for a sympathetic blockade therapeutic effect is from about 1.0 to about 2.0 mg/kg body weight per day. Other factors affecting the preferred daily dose include, for example, the age, weight, and sex of the subject; the severity of the condition; and the route and frequency of administration. In many instances, the preferred daily bretylium cation dosage will be the same as the dosage employed in injectable bretylium tosylate compositions known to those of ordinary skill in the art for obtaining the desired effect.

The daily dose is preferably administered in the form of from 1 to 4 unit doses (e.g., it typically is administered every 6 hours to once per day), more preferably from 2 to 3 unit doses (this preference stems from the fact that the elimination half-life of the bretylium cation is from about 10 to 12 hours). When administered orally, the daily dose may be administered in the form of a unit dose of a composition comprising the bretylium cation or as part of a kit comprising a source of the bretylium cation. Unit dosage forms typically administer, for example, a 10, 20, 25, 37.5, 50, 75, 100, 125, 150, 175, 200, 250, 300, 350, or 400 mg dose of the bretylium cation for an average-size human (average-size being roughly 75 kg). Where the bretylium cation is provided in the form of bretylium tosylate, dosage units are preferably capsules or tablets containing about 120, 240, or 360 mg of bretylium tosylate. The dosage unit form may be selected to accommodate the desired frequency of administration used to achieve the specified daily dosage. It should be recognized that the amount of the unit dosage and the dosage regimen for treating a condition may vary widely and will depend on a variety of factors, including the age, weight, sex, and medical condition of the subject; the severity of the condition; and the route and frequency of administration. For example, subjects with impaired renal function may require a lesser amount of the bretylium cation relative to subjects with normal renal function due to the higher clearance time needed to eliminate the bretylium cation, which is eliminated unchanged in the urine.

In a particularly preferred embodiment, the only one unit dosage of the bretylium cation is administered per day. As has been discovered in accordance with this invention, the benefits of the bretylium cation (e.g., increased ventricular fibrillation threshold) can generally be extended over time so that only 1 dose per day is preferred, particularly where the source of facilitating anion is, for example, a source of the salicylate anion, the lauryl sulfate anion, and/or the di(2-ethylhexyl)sulfosuccinate anion. In one of the most preferred embodiments, the benefits of the bretylium cation are extended by administering the bretylium cation with aspirin (in an especially preferred embodiment, the source of the bretylium cation (e.g., bretylium tosylate) is administered with aspirin alone).

B. The Facilitating Anion

The pharmaceutical compositions and kits of the present invention preferably have a molar ratio of the facilitating anion to the bretylium cation of at least about 0.5, more preferably at least about 0.75, still more preferably from about 0.75 to about 4, and still even more preferably from about 1 to about 2.

C. β-Receptor Blocker

When the composition or kit comprises a β-receptor blocker (e.g., propranolol, atenolol, esmolol, metoprolol, labetalol, talinolol, timolol, carvedilol, or acebutolol), the β-receptor blocker is preferably administered as a subtherapeutic dose relative to conventional β-blocking dosages known to those of ordinary skill in the-art. Such subtherapeutic doses of the β-receptor blocker typically vary with the compound selected. For example, the following dosages are preferred for the following compounds: about 0.05 to about 0.2 mg/kg body weight for propranolol; about 0.25 to about 0.1 mg/kg body weight for atenolol; about 20 to about 300 $\mu$g/kg body weight for esmolol; about 0.035 to about 0.1 mg/kg body weight for metoprolol; about 100 to about 350 mg/dose for labetalal for an average-size human; about 350 to about 500 mg/dose for talinolol for an average-size human; about 300 to about 750 mg/dose for timolol for an average-size human; and about 50 to about 100 mg/dose for acebutolol for an average-size human.

D. Neutralizing Agent

As noted above, the composition or kit preferably comprises a neutralizing agent when the composition or kit is being administered orally. The neutralizing agent preferably is present in an amount sufficient to increase the pH of the aqueous contents of the stomach after ingestion to a value sufficient to prevent the absorption of a significant fraction of the facilitating anion as its conjugate acid into the gastrointestinal mucosa. More preferably, the amount of neutralizing agent is sufficient to temporarily increase the pH of the aqueous contents of the stomach to at least about 2, more preferably at least about 3, and still more preferably at least about 4. In a particularly preferred embodiment, the pH increases to at least about 2 within less than about 1 minute, and remains greater than about 2 for at least about 15 minutes. Although an amount of neutralizing agent sufficient to increase the pH to a value greater than about 7 may be used, the amount preferably does not increase the pH to a value greater than about 7. For most neutralizing agents, an amount of up to about 50 mmole (preferably from about 0.05 to about 50 mmole) is sufficient to achieve the desired pH increase in an average-size human. When sodium bicarbonate is used as the neutralizing agent in an average-size human, for example, it preferably is present in an amount of from about 0.1 to about 4200 mg, more preferably from about 5 to about 4200 mg, still more preferably from about 10 to about 4200 mg, and still even more preferably from about 1000 to about 4200 mg.

It should be recognized that the facilitating anion also may function to increase the pH of the stomach when the facilitating anion is converted into its corresponding conjugate acid. Accordingly, the amount of neutralizing agent required may generally be reduced by increasing the amount of the facilitating anion in the composition. In some embodiments, the preference for a separate neutralizing agent may be entirely eliminated by selection of an appropriate amount of a suitable facilitating anion.

E. Buffering Agents

As noted above, the compositions and kits intended to be administered orally preferably comprise a buffering agent, particularly where a neutralizing agent is also included in the composition or kit. When a buffering agent is used in combination with the neutralizing agent, the molar ratio of buffering agent to neutralizing agent may vary widely. Preferably, the molar ratio is from about 0.5 to about 1.5, and more preferably about 1.

F. Anti-hypotensive Agent

When the composition or kit comprises an anti-hypotensive agent (e.g., a tricyclic anti-depressant compound selected from the group consisting of protriptyline, mazindol, amitriptyline, nortriptyline, and desipramine), the anti-hypotensive agent is preferably administered as a subtherapeutic dose relative to conventional dosages known to those of ordinary skill in the art. Such subtherapeutic doses of the anti-hypotensive agent in general are preferably from about 0.2 to 30 mg/day (in divided doses) for an average-size human. This preferred dosage, however, varies with the anti-hypotensive agent selected. For example, when administered to an average-size human, it is preferred to use from about 2.0 to about 20 mg/dose for protriptyline for an average-size human, from about 0.2 to about 10 mg/dose for mazindol for an average-size human, from about 3.0 to about 30 mg/dose for amitriptyline for an average-size human, from about 2.0 to about 20 mg/dose for nortriptyline for an average-size human, and from about 2.0 to about 20 mg/dose for desipramine for an average-size human.

Methods of Use

As discussed above, the present invention is directed to preventing and treating heart conditions. The method comprises administering (orally or otherwise) a therapeutically-effective amount of one or more of the compositions or kits described above to a subject having or susceptible to such a condition.

Initial treatment of a patient suffering from a medical condition where treatment with the bretylium cation is appropriate can-begin with the dosages discussed above. In many instances, the treatment is continued as necessary over a period of several weeks to several months or years until the condition has been controlled or eliminated. Patients undergoing treatment with the compositions or kits disclosed herein can be routinely monitored by any of the methods well known in the art to determine the effectiveness of therapy. Continuous analysis of such data permits modification of the treatment regimen during therapy so that optimal effective amounts of the compositions and kits of this invention may be administered at any point in time, and so that the duration of treatment can be determined as well. In this way, the treatment regimen and dosing schedule can be rationally modified over the course of therapy so that the lowest amount of the bretylium cation exhibiting satisfactory effectiveness is administered, and so that administration is continued only so long as is necessary to successfully prevent or treat the condition.

A. Order of Administration of the Bretylium Cation, the Facilitating Anion or β-Receptor Blocker, and Other Optional Ingredients of a Kit As noted above, a kit may be used in accordance with this invention, wherein the therapeutic ingredients to be administered are contained in at least two separate, discrete sources. To illustrate, a source of the bretylium cation may be separate and discrete from a source of a facilitating anion and/or a source of a β-receptor blocker. Or, to illustrate further, a source of a bretylium anion may also contain a facilitating anion, while a neutralizing agent is contained in a separate, discrete source. Or to illustrate even further, there may be two separate, discrete sources of ingredients which each contain a bretylium cation and a facilitating anion. Regardless, the use of a kit provides the advantage of being able to administer two or more different ingredients independently of each other. This, in turn, permits, for example, more effective adjustment in the amount of the facilitating anion, β-receptor blocker, neutralizing agent, buffering agent, and/or anti-hypotensive agent administered relative to the amount of the bretylium cation administered.

Typically, when a kit is used, it is preferred that the facilitating anion(s) and/or β-receptor blocker(s) (as well as any neutralizing agent, buffering agent, and/or anti-hypotensive agent) be administered jointly or within about 30 minutes before or after (and more preferably within about 15 minutes before or after) the bretylium cation is administered. An ingredient administered jointly with the bretylium cation may be administered as a component of a bretylium cation source (i.e., where the bretylium cation source is a composition containing the bretylium cation and the additional ingredient). Alternatively, the additional ingredient may be administered as a component of a source separate and distinct from the bretylium cation source (i.e., where the source of the additional ingredient is administered simultaneously with the bretylium cation source). Or, as another alternative, the source containing the additional ingredient may be combined with the bretylium cation source before the administration of the bretylium cation source, and thereby administered as a composition containing the bretylium cation and the additional ingredient.

In a particularly preferred embodiment, a kit is used which contains a source comprising a unit dosage of the bretylium cation and a separate source comprising a unit dosage of a facilitating anion (e.g., a kit containing a tablet comprising aspirin and a tablet comprising bretylium tosylate). The kit may also contain one or more other ingredients (e.g., a neutralizing agent, a buffering agent, a antihypotensive agent, and/or a β-receptor blocker) which may be a component of the source of the bretylium cation, a component of the source of the facilitating anion, and/or a component of a source separate from the sources of the bretylium cation and facilitating anion.

In yet another particularly preferred embodiment, a source containing a unit dosage of a neutralizing agent (and, optionally, a unit dosage of a buffering agent) is initially administered. This is then followed by the administration of a source(s) containing the bretylium cation and a facilitating anion.

In still another particularly preferred embodiment, administration of a source(s) of the bretylium cation and a facilitating anion is followed (preferably immediately) by the administration of a source(s) containing a unit dosage of an anti-hypotensive agent and/or a β-receptor blocker.

B. Injectable Compositions

As noted above, many of the compositions and kits of the present invention may be administered parenterally. In one particularly preferred embodiment of this invention, an injectable composition is used which comprises the bretylium cation and a facilitating anion (e.g., the salicylate anion or the acetylsalicylate anion). Such a composition is particularly useful for the emergency treatment of, for example, ventricular fibrillation or myocardial infarction.

In a particularly preferred embodiment, the injectable composition comprises (1) the bretylium cation, (2) a facilitating anion, and (3) a tricyclic antidepressant to prevent sympathetic blockade and a material decrease in blood pressure. Suitable tricyclic antidepressants are discussed above in detail.

In another particularly preferred embodiment, the injectable composition comprises (1) the bretylium cation, (2) a facilitating anion, and (3) a β-receptor blocker. Here, the facilitating anion is preferably salicylate or acetylsalicylate. In one of the most preferred embodiments, the injectable composition comprises: (1) the bretylium cation (preferably in the form of bretylium tosylate), (2) aspirin, and (3) a β-receptor blocker. In all these embodiments, the more preferred β-receptor blockers are esmolol, metoprolol, and propranolol, with metoprolol and propranolol being the most preferred.

Other Quaternary Ammonium Cations

The pharmaceutical compositions and kits of the present invention also are useful for the oral administration of other nonpeptide cationic therapeutic agents, particularly therapeutic agents comprising quaternary ammonium cations, in accordance with the compositions and kits discussed above. These pharmaceutical compositions and kits can be prepared as set forth in this application by replacing the bretylium cation with a comparable molar fraction of a cation of the desired cationic therapeutic agent, such as the propyromazine.

Hypothesized Mechanisms of Action

In the aqueous contents of the gastrointestinal tract (particularly the stomach and intestine), orally administered bretylium tosylate (or other pharmaceutically acceptable sources of the bretylium cation) is ionized to the bretylium cation and the tosylate anion (or the other anion in the bretylium-cation source). To provide the desired therapeutic effect, however, the bretylium cation must be absorbed from the aqueous contents of the gastrointestinal tract through the lipid phase mucosa of the gastrointestinal tract into the blood, and then transferred from the blood to the target cells (typically (a) the sympathetic ganglia and their postganglionic andrenergic neurons, and (b) cardiac cells). Absorption of the bretylium cation from the gastrointestinal tract into the blood requires that the hydrophilic bretylium cation cross the lipophilic lipid phase boundary of the gastrointestinal tract. It has been discovered that this absorption (or crossing of the lipid phase boundary) can be improved if the bretylium cation is combined with one or more suitable types of anions (i.e., facilitating anions) resulting in a bretylium-cation/facilitating-anion combination that is more lipophilic, or less hydrophilic, than bretylium tosylate.

It is hypothesized that the bretylium cation and the facilitating anion in the gastrointestinal tract can exist in the form of separate ions, ion pairs, micelles, or otherwise. When the bretylium cation enters the lipid phase, however, it does so as bretylium-cation/facilitating-anion combination in the form of ion pairs and/or higher ion aggregates, such as inverse micelles. These bretylium-cation/facilitating-anion combinations possess a neutral or substantially neutral charge. In addition, these bretylium-cation/facilitating-anion combinations are more lipophilic, or less hydrophilic, than bretylium tosylate.

When the bretylium cation and facilitating anion are ingested and ionized in the absence of a neutralizing agent, the HCl present in the stomach converts a portion of the ionized anions to the corresponding conjugate acid of the anions, which is then largely absorbed by the lipid mucosa in the intestine. As these anions are converted to their conjugate acid form and absorbed, additional anions are then converted to their conjugate acid, and, in turn, absorbed in the intestine. If the anions are too readily converted to their conjugate acid form and/or the pH of the gastrointestinal tract is too low, the hydrophilic chloride anions will effectively be the only anions available for combination with the bretylium cation (if tosylate anions are also present, they too will be converted into their conjugate acid, p-toluenesulfonic acid, and, in turn, absorbed in the intestine). Because the bretylium cation cannot be spacially separated from a counterion, and the chloride anions are not readily removed from the aqueous phase, the bretylium cation remains in the aqueous fluid of the stomach and intestine and is ultimately not absorbed. To reduce or eliminate this problem, a neutralizing agent may be administered to increase the pH of the stomach. It is believed that such a pH increase enhances the absorption of the bretylium cation by reducing the removal of the facilitating anion as its conjugate acid such that a larger portion of the facilitating anion remains available to form the bretylium-cation/facilitating-anion combination.

It is further hypothesized that the compositions and kits of this invention not only enhance the absorption of the bretylium cation from the gastrointestinal tract into the blood, but also enhance the permeation of the bretylium cation from the blood through the capillary walls and the target tissue (the target tissue being myocardial cells, and/or sympathetic nerve endings and ganglia). For example, the di(2-ethylhexyl)sulfosuccinate anion 2 promotes the formation of water-in-oil emulsions. Such emulsions generally consist of droplets having an aqueous core surrounded by di(2-ethylhexyl)sulfosuccinate anions 2, with the anionic sulfonate groups directed inwardly toward the core center and the hydrocarbon groups directed outwardly from the core, in contact with the oil or lipid bulk phase. The core typically contains a sufficient number of cations to provide the whole assembly with a neutral charge. Such emulsion droplets generally have a radius ranging from about $10 \times 10^{-8}$ cm to about $30 \times 10^{-8}$ cm. Because the typical cell wall has a hydrophobic core bounded by a film having a thickness of about $30 \times 10^{-8}$ cm, a closed emulsion droplet may not form in such a film since the film is too thin to surround the droplet. It is hypothesized, however, that a short cylinder of di(2-ethylhexyl)sulfosuccinate anions 2 may form instead, with the anionic sulfonate groups directed inwardly toward an aqueous core and their hydrocarbon groups directed outwardly toward the lipid of the cell wall, and with the 2 ends of the cylinder open. One of the open ends is directed outward and the other is directed into the cell. Such a structure would act as a conduit through which the bretylium cation could reach the interior of target cells.

It is additionally hypothesized that these emulsion droplets and/or cylinders also may form in the mucosa of the intestine, with bretylium acting as the neutralizing cation, thereby promoting the absorption of the bretylium cation through the intestinal walls in a similar manner as in the walls of the target cells.

Definitions

The term "hydrocarbyl" refers to a group composed of carbon and hydrogen. This definition includes alkyl, alkenyl, and alkynyl groups which are each straight chain, branched chain, or cyclic hydrocarbons typically having from 1 to about 30 carbons atoms. Also included in this definition are aryl groups composed of carbon and hydrogen. Hydrocarbyl therefore includes, for example, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethyne, propyne, butyne, pentyne, hexyne, phenyl, naphthyl, anthracenyl, benzyl, and isomers thereof.

The term "substituted hydrocarbyl" refers to a hydrocarbyl group in which one or more hydrogen has been substituted with a heteroatom-containing group. Such substituent groups include, for example, halo, oxo, heterocycle, alkoxy, hydroxy, aryloxy, —$NO_2$, amino, alkylamino, or amido. When the substituent group is oxo, the substituted hydrocarbyl can be, for example, an acyl group.

The term "alkyl" refers to linear or branched hydrocarbon groups having from 1 to about 30 carbon atoms. Examples of such groups include methyl, ethyl, n-propyl, isopropyl, n-butyl, isobutyl, sec-butyl, tert-butyl, pentyl, iso-amyl, hexyl, dodecyl, and the like. It should be recognized that such a group may be, for example, a residue of a saturated fatty acid formed by removing the carboxylic acid group from the fatty acid. More preferred alkyl groups are alkyl groups comprising at least 6 carbon atoms.

The term "alkenyl" embraces linear or branched hydrocarbon groups having at least one carbon-carbon double bond, and from 2 to about 30 carbon atoms. Examples of alkenyl groups include ethenyl, allyl, propenyl, butenyl, 4-methylbutenyl, and the like. The term "alkenyl" embraces groups having "cis" and "trans" orientations, or, alternatively, "E" and "Z" orientations. It should be recognized that such a group may be, for example, a residue of an unsaturated fatty acid (having one or more double carbon-carbon bonds) formed by removing the carboxylic acid group from the fatty acid. More preferred alkenyl groups are alkyl groups comprising at least 6 carbon atoms.

The term "alkynyl" refers to linear or branched hydrocarbon groups having at least 1 carbon-carbon triple bond, and from 2 to about 30 carbon atoms. Examples of alkynyl groups include propargyl, 1-propynyl, 2-propynyl, 1-butyne, 2-butynyl, 1-pentynyl, and the like. More preferred alkyl groups are alkynyl groups comprising at least 6 carbon atoms.

The term "cycloalkyl" refers to saturated carbocyclic hydrocarbon groups having 3 to about 30 carbon atoms. Examples of such groups include cyclopropyl, cyclobutyl, cyclopentyl, cyclohexyl, and the like. More preferred cycloalkyl groups are "lower cycloalkyl" groups having from 3 to about 8 carbon atoms.

The term "cycloalkenyl" refers to partially unsaturated carbocyclic hydrocarbon groups having from 3 to about 30 carbon atoms. Examples of such groups include cyclobutenyl, cyclopentenyl, cyclohexenyl, and the like. More preferred cycloalkenyl groups are "lower cycloalkenyl" groups having from 4 to about 8 carbon atoms.

The term "aryl" refers to aromatic groups such as phenyl, naphthyl, tetrahydronaphthyl, indanyl, and biphenyl. The preferred aryl is phenyl. Aryl moieties may also be substituted at a substitutable position with one or more substituents selected independently from alkyl, alkenyl, alkynyl, cycloalkyl, cycloalkenyl, and the like. The term "aryl, alone or in combination" refers to a carbocyclic aromatic system containing 1, 2, or 3 rings, wherein such rings may be attached together in a pendent manner or may be fused.

The term "arylalkyl" refers to aryl-substituted alkyl groups such as benzyl, diphenylmethyl, triphenylmethyl, phenylethyl, and diphenylethyl. The aryl in the aralkyl may be additionally substituted with one or more substituents selected independently from alkyl, alkenyl, alkynyl, cycloalkyl, and cycloalkenyl. The terms "arylalkenyl" and "arylalkynyl" are defined in a comparable manner.

The term "pharmaceutically acceptable" means being compatible with the other components of the composition or kit being administered, and not deleterious to the intended recipient of the composition or kit.

The term "pharmaceutically-acceptable salts" refers to salts such as alkali metal salts, and common salts of free acids or free bases. The nature of the salt is not critical, provided that it is pharmaceutically-acceptable. Suitable pharmaceutically-acceptable salts of the bretylium cation and/or facilitating anion may be prepared from an inorganic acid or an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclyl, carboxylic, and sulfonic classes of organic acids (e.g., formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acid). Suitable pharmaceutically-acceptable salts of these compounds include metallic salts and organic salts. More preferred metallic salts include, but are not limited to, appropriate alkali metal (group IA) salts, alkaline earth metal (group IIA) salts, and other physiologically acceptable metals. Such salts can be made from aluminum, calcium, lithium, magnesium, potassium, and sodium. Preferred organic salts can be made from amines and quaternary ammonium salts, including, in part, trimethylamine, diethylamine, N,N'-dibenzylethylenediamine, chloroprocaine, choline, diethanolamine, ethylenediamine, meglumine (N-methylglucamine), and procaine.

The term "ventricular fibrillation threshold" refers to the lowest current level that, when applied to the heart, causes sustained ventricular fibrillation.

The term "effective ventricular refractory period" refers to the period during which the heart cannot be stimulated to contract by a super threshold electrical stimulus.

The term "rate-corrected $Q$-$T_c$ interval" refers to the interval between the Q wave and the T wave, corrected for heart rate.

The term "prevent" means to at least partially suppress the onset of a condition.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

EXAMPLES

The following examples are simply intended to further illustrate and explain the present invention. This invention, therefore, should not be limited to any of the details in these examples. The symbols and conventions used in these examples are consistent with those used in the contemporary pharmacological literature.

Unless otherwise stated, the pharmaceutical grade bretylium tosylate used in these examples was obtained from Ganes Chemicals, Inc., Carlstadt, N.J. The facilitating anions used in these examples are commercially available or may be prepared as discussed above.

Example 1

A pharmaceutical composition suitable for oral administration is prepared having the following composition:

| INGREDIENT | WEIGHT PERCENT[1] |
| --- | --- |
| bretylium cations | 0.5% to 50% |
| facilitating anions | 0.5% to 50% |
| neutralizing agent | 15% to 99% |

[1]Based on the total weight of the bretylium cations, facilitating anions, and neutralizing agent.

Example 2

A pharmaceutical composition suitable for oral administration is prepared having the following composition:

| INGREDIENT | WEIGHT PERCENT[1] |
|---|---|
| bretylium cations | 1% to 30% |
| facilitating anions | 1.7% to 30% |
| neutralizing agent | 50% to 98% |

[1]Based on the total weight of the bretylium cations, facilitating anions, and neutralizing agent.

Example 3

A pharmaceutical composition suitable for oral administration is prepared having the following composition:

| INGREDIENT | AMOUNT (mg) | WEIGHT FRACTION[1] |
|---|---|---|
| bretylium tosylate | 500 | 0.095 (0.056 for bretylium cation alone) |
| sodium di(2-ethylhexyl) sulfosuccinate | 536 | 0.102 (0.097 for di(2-ethylhexyl) sulfosuccinate anion alone) |
| sodium bicarbonate | 4200 | 0.802 |

[1]Based on the total weight of the composition.

Example 4

A pharmaceutical composition suitable for oral administration is prepared having the following composition:

| INGREDIENT | AMOUNT (mg) | WEIGHT FRACTION[1] |
|---|---|---|
| bretylium tosylate | 1275 | 0.275 (0.161 for bretylium cation alone) |
| sodium di(2-ethylhexyl) sulfosuccinate | 1367 | 0.294 (0.279 for di(2-ethylhexyl) sulfosuccinate anion alone) |
| sodium bicarbonate | 2000 | 0.431 |

[1]Based on the total weight of the composition.

Example 5

A pharmaceutical composition suitable for oral administration is prepared having the following composition:

| INGREDIENT | AMOUNT (mg) | WEIGHT FRACTION[1] |
|---|---|---|
| bretylium tosylate | 1275 | 0.214 (0.126 for bretylium cation alone) |
| sodium salicylate | 485 | 0.081 (0.069 for salicylate anion alone) |
| sodium bicarbonate | 4200 | 0.705 |

[1]Based on the total weight of the composition.

Example 6

A pharmaceutical composition suitable for oral administration is prepared having the following composition:

| INGREDIENT | AMOUNT (mg) | WEIGHT FRACTION[1] |
|---|---|---|
| bretylium di(2-ethylhexyl) sulfosuccinate | 3600 | 0.643 (0.235 for bretylium cation alone) (0.408 for di(2-ethylhexyl) sulfosuccinate anion alone) |
| sodium bicarbonate | 2000 | 0.357 |

[1]Based on the total weight of the composition.

Example 7

A pharmaceutical composition suitable for oral administration is prepared having the following composition:

| INGREDIENT | AMOUNT (mg) | WEIGHT FRACTION[1] |
|---|---|---|
| bretylium di(ethylhexyl) sulfosuccinate | 3600 | 0.545 (0.2 for bretylium cation alone) (0.345 for di(2-ethylhexyl) sulfosuccinate anion alone) |
| sodium bicarbonate | 2000 | 0.303 |
| citric acid | 1000 | 0.152 |

[1]Based on the total weight of the composition.

Example 8

A pharmaceutical composition suitable for oral administration is prepared having the following composition:

| INGREDIENT | AMOUNT (mg) | WEIGHT FRACTION[1] |
|---|---|---|
| bretylium salicylate | 2000 | 0.4 (0.241 for bretylium cation alone) (0.159 for salicylate anion alone) |
| sodium bicarbonate | 2000 | 0.4 |
| citric acid | 1000 | 0.2 |

[1]Based on the total weight of the composition.

Example 9

A pharmaceutical composition suitable for oral administration is prepared having the following composition:

| INGREDIENT | AMOUNT (mg) | WEIGHT FRACTION[1] |
|---|---|---|
| bretylium tosylate | 120 | 0.261 (0.153 for bretylium cation alone) |
| sodium di(2-ethylhexyl)sulfosuccinate | 130 | 0.283 (0.268 for di(2-ethylhexyl)sulfosuccinate anion alone) |
| sodium citrate | 200 | 0.435 |
| protriptyline | 10 | 0.022 |

[1]Based on the total weight of the composition.

Example 10

A pharmaceutical composition is prepared having the following composition:

| INGREDIENT | AMOUNT (mg) | WEIGHT FRACTION[1] |
|---|---|---|
| bretylium tosylate | 12,000 | 0.021 (0.012 for bretylium cation alone) |
| aspirin | 5,000 | 0.009 (0.008 for acetylsalicylate anion alone) |
| sodium citrate | 50,000 | 0.088 |
| water | 500,000 (500 ml) | 0.882 |

[1] Based on the total weight of the composition.

This composition can be placed into a conventional drip bag and administered by continuous infusion over an appropriate period (e.g., 48 hr). Alternatively, the composition can be further divided into suitable unit oral dosage forms (e.g., unit dosage forms containing 120 mg of bretylium tosylate), and orally administered.

Example 11

An oral pharmaceutical composition is prepared having the following composition:

| INGREDIENT | AMOUNT (mg) | WEIGHT FRACTION[1] |
|---|---|---|
| bretylium di(2-ethylhexyl)sulfosuccinate | 500 | 0.926 |
| protriptyline | 40 | 0.074 |
| water | An amount sufficient to provide a total final volume for the solution of 50 ml | |

[1] Based on the total weight of bretylium di(2-ethylhexyl)sulfosuccinate and protriptyline.

Example 12

A pharmaceutical composition suitable for oral administration is prepared having the following composition:

| INGREDIENT | WEIGHT PERCENT[1] |
|---|---|
| bretylium cations | 0.5% to 64% |
| facilitating anions | 0.3% to 63% |
| neutralizing agent | 0.02% to 99% |

[1] Based on the total weight of the bretylium cations, facilitating anions, and neutralizing agent.

Example 13
Determination of Partition Coefficients

Several formulations of the present invention were tested using an n-octanol/aqueous buffer system to measure the partition coefficients for the bretylium cation in the presence of the facilitating anions of those formulations. An acidified aqueous solution of bretylium tosylate was first prepared. Sodium bicarbonate and a salt comprising the facilitating anion to be tested was then added to the aqueous solution. The salt comprising the facilitating anion was added in an amount sufficient to provide a 1:1 molar ratio of the facilitating anion to the bretylium cation. The sodium bicarbonate was provided in an amount sufficient to produce one of 4 preselected pH values. An equal volume of n-octanol was then added to this solution and the solution was shaken. The mixture was centrifuged to separate an octanol layer and an aqueous layer, and the distribution ratio of the bretylium cation between the octanol-rich phase and the aqueous-rich phase (that is, the partition coefficient) was measured. This analytical approach provides a suitable model for evaluating the bioavailability of the bretylium cation in the compositions tested.

A. Preparation of Aqueous Bretylium Tosylate Solution

The aqueous bretylium tosylate solutions used in the procedure were prepared in the following manner. An amount of one of the buffer solutions described below (3.0 ml when the most acidic buffer solution was used, and 4.0 ml when the other 3 buffer solutions were used) was transferred to a beaker or an erlenmeyer flask by pipette. To the buffer solution was added 50 mg of bretylium tosylate per ml of buffer solution and an equimolar amount of the sodium salt of the facilitating anion. For example, where the facilitating anion tested was di(2-ethylhexyl)sulfosuccinate, 54 mg of sodium di(2-ethylhexyl) sulfosuccinate was added per ml of buffer solution. Where the facilitating anion tested was salicylate, 19 mg of sodium salicylate was added per ml of buffer solution. Test solutions comprising other facilitating agents were prepared in a similar manner.

B. Preparation of Sodium Bicarbonate Buffer Solutions

Each of the pharmaceutical compositions was tested using each of the following sodium bicarbonate buffer systems:

The first buffer solution was prepared by dissolving 1.0 g of sodium bicarbonate in 100 ml of 0.95M HCl. A pH meter equipped with a conventional glass electrode and a calomel reference electrode was used to measure the nominal pH of this solution and the other 3 buffer solutions. The nominal pH measured for the first solution was 0.8. Because the glass electrode probably is not able to respond adequately to such an acidic solution, it is likely that the actual pH of this solution was lower, perhaps slightly negative. The nominal pH of this solution, however, was reproducible.

The second buffer solution was prepared by dissolving 7.5 g of sodium bicarbonate in 100 ml of 0.95M HCl. This solution had a reproducible nominal pH of 2.2, slightly higher than the expected pH of about 2.0.

The third buffer solution was prepared by dissolving 8.0 g of sodium bicarbonate in 100 ml of 0.95M HCl. This solution had a nominal pH between about 5.0 and about 6.0. While the pH meter is reliable in this pH range, the pH was somewhat variable because the solution had minimal buffer capacity.

The 4th buffer solution was prepared by dissolving 10.0 g of sodium bicarbonate in 100 ml of 0.95M HCl. This solution had a reproducible nominal pH of 7.7 that likely is close to the actual pH of the solution.

The first buffer solution was intended to model the acidity of the aqueous contents of the human stomach. The other 3 buffer solutions were intended to model the aqueous contents of the stomach after administration of an amount of sodium bicarbonate to reduce the acidity of the stomach.

C. Facilitating Anions Tested

The sodium salts of the following facilitating anions were tested: di(2-ethylhexyl)phosphate, di(2-ethylhexyl) sulfosuccinate, lauryl sulfate, and salicylate. All these salts were commercially available from Aldrich Chemical, Milwaukee, Wis. and/or Ecolab, Inc., St. Paul Minn. Each of the 4 facilitating anions was tested in each of the 4 buffer systems.

D. Preparation and Equilibration of n-Octanol/Buffer Systems

A 1.0 ml aliquot of the formulated aqueous test solution was added to 1.0 ml of n-octanol (Aldrich Chemical Co., HPLC grade, 99% purity), and the mixture was shaken for 30 seconds. The n-octanol and aqueous phases, which are not miscible, were separated by centrifuging at about 3000 rpm for about 10 minutes or until clarification was achieved. The phases were physically separated and the bretylium concentration of each phase was determined as described below. This procedure was followed for each combination of facilitating anion and buffer system. In addition, a corresponding control test was carried out without a facilitating anion in each of the buffer systems.

E. Measurement of Partition Coefficient

The concentration of the bretylium cation in the separated n-octanol and aqueous phases was determined by spectrophotometry using the long wavelength absorption of the bretylium cation at 270 nm. This band is due to the benzene chromophore of the bretylium cation.

To determine the concentration of bretylium in the octanol phase, each n-octanol phase sample obtained as above was diluted with an equal volume of pure n-octanol. The resulting n-octanol solution was then equilibrated with 1.5 times its own volume of 3 M HCl to protonate the acid of any acid weaker than HCl that was present. Because bretylium chloride is very water soluble but only sparingly soluble in n-octanol, it is extracted into the aqueous phase in high yield. The absorbance of the resulting aqueous phase at 270 nm was then determined spectrophotometrically. The protonated former facilitating anion (which otherwise might contribute to the absorbance) was converted to its neutral conjugate acid by the HCl and remained in the n-octanol phase. For example, if the bretylium cation is present as a tosylate in the octanol phase, then acidification largely converts the tosylate anion to toluenesulfonic acid, an acid preferentially soluble in the n-octanol phase. Accordingly, the facilitating anion is not transferred to the aqueous phase with the bretylium chloride and does not contribute to the measured absorbance. The chloride anion is present in the aqueous phase but is free of absorbance in the region of interest.

To determine the concentration of bretylium in the aqueous phase, each aqueous phase sample obtained as above was mixed with twice its own volume of 5M HCl and the resulting aqueous solution was then equilibrated with a volume of n-octanol equal to twice the original aqueous phase sample volume. The HCl protonated the facilitating anion and any other anions of acids weaker than HCl that were present and might contribute to the absorbance if allowed to remain in solution. The unwanted anions were extracted into the n-octanol phase as their conjugate acids. The absorbance of the aqueous phase, after the n-octanol extraction, was determined spectrophotometrically at 270 nm.

Test solutions exhibiting a measured absorbance greater than 1.2 were diluted with water so as to provide an absorbance between 0.040 and 1.2 and then re-measured. This dilution was employed to provide bretylium concentrations within the concentration range in which absorbance could be reliable measured. In such cases, the absorbance of the diluted test solution was then multiplied by a dilution factor to determine the true absorbance of the original test solution. Alternatively, the original separated aqueous solution and the corresponding original separated n-octanol solution were diluted by the same factor so as to cancel out the dilution factor during the calculation of the partition coefficient.

Dilution occurs whenever additional solvent is added to a solution of an analyte, or the analyte is transferred to a new solution of greater volume than its original volume. Such increases in volume may occur for reasons of convenience, or because the parameter to be measured (e.g., absorbance) is above the optimal range of instrumental accuracy. The dilution factor is the final volume divided by the initial volume. If several dilutions have been made the dilution factors are multiplicative. For example, if the original aqueous test sample was 1.0 ml (as in the present case) and the bretylium ion is recovered in 1.5 ml of aqueous acid, the dilution factor is 1.5. If the absorbance of this solution is too high for accurate measurement, and 0.3 ml of this solution is diluted with 5 ml of water, a second dilution has occurred with a dilution factor of 17.7 (that is, 5.3/.3). The overall dilution factor is 26.5 (that is, 17.7×1.5). To determine the absorbance of the original solution, which is proportional to its bretylium concentration, the absorbance of the final solution is multiplied by the overall dilution factor (26.5 in the illustrative example). The proportionality constant that converts absorbance to the molar concentration of the bretylium cation is the molar absorbance.

In the present case, the ratio of the bretylium concentration in the octanol phase to the bretylium concentration in the aqueous phase (i.e., the partition coefficient) is needed. When the 2 overall dilution factors are the same, then the ratio of concentrations is equal to the ratio of observed absorbances. When the 2 overall dilution factors are not the same, then the ratio of observed absorbances times the ratio of dilution factors equals the ratio of concentrations. The analytical scheme described above has the advantage that all absorbances are measured in aqueous solution, so that the molar absorbance is constant.

The partition coefficients calculated from the measured absorbances are set forth in Table 13A below. These test results confirm that the partition coefficient (and, thus, the bioavailability) of orally administered bretylium cations can be increased—in some cases up to nearly 10-fold—by using suitable a facilitating anion and/or a neutralizing agent in combination with the bretylium cation. While increasing the pH of the test solution alone increased partition coefficient values, increasing the pH of the solution in combination with the addition of a suitable facilitating anion resulted in an additional increase in partition coefficient values in all cases. Similarly, use of certain facilitating anions in combination with the bretylium cation without a concurrent increase in the pH of the test solution materially increased partition coefficient values, particularly for the sulfate and sulfosuccinate facilitating anions tested. The phosphate and salicylate facilitating anions tested, however, generally performed better and provided higher partition coefficient values as the pH of the test solution increased.

TABLE 13A

| NOMINAL pH | FACILITATING ANION | PARTITION COEFFICIENT |
|---|---|---|
| 0.8 | None | 0.33 |
| 2.1 | None | 0.48 |
| 5.5 | None | 0.45 |
| 7.7 | None | 0.49 |
| 0.8 | di(2-ethylhexyl)phosphate | 0.35 |
| 2.2 | di(2-ethylhexyl)phosphate | 0.49 |
| 5.5 | di(2-ethylhexyl)phosphate | 0.51 |
| 7.7 | di(2-ethylhexyl)phosphate | 2.33 |
| 0.8 | di(2-ethylhexyl)sulfosuccinate | 2.19 |
| 2.2 | di(2-ethylhexyl)sulfosuccinate | 2.52 |
| 5.5 | di(2-ethylhexyl)sulfosuccinate | 4.16 |
| 7.7 | di(2-ethylhexyl)sulfosuccinate | 3.61 |
| 0.8 | lauryl sulfate | 1.91 |
| 2.2 | lauryl sulfate | 3.54 |
| 5.5 | lauryl sulfate | 3.71 |
| 7.0 | lauryl sulfate | 4.01 |

TABLE 13A-continued

| NOMINAL pH | FACILITATING ANION | PARTITION COEFFICIENT |
|---|---|---|
| 0.8 | salicylate | 0.56 |
| 2.2 | salicylate | 1.31 |
| 5.5 | salicylate | 1.31 |
| 7.0 | salicylate | 1.90 |

F. Control Experiments

Two series of control experiments were conducted to further validate the above procedure. In the first series of experiments, the molar absorbance of bretylium in the absence of a facilitating anion was measured at 2 different initial concentrations. Bretylium tosylate in an amount of 150 mg was added to 3.0 ml of water. This solution was then acidified with HCl, extracted with octanol, and diluted in accordance with the procedure described above. The experiment was repeated using an initial aqueous solution that was 100 times more dilute. The molar absorbance was calculated for each solution by dividing its absorbance after extraction by its initial concentration. The results are reported in Table 13B below.

TABLE 13B

| INITIAL BRETYLIUM TOSYLATE CONCENTRATION (moles/L) | ABSORBANCE[1] | MOLAR ABSORBANCE (L/mole) |
|---|---|---|
| $1.21 \times 10^{-1}$ | 43.0 | 355 |
| $1.21 \times 10^{-3}$ | 0.39 | 326 |

[1]Corrected for dilution

The consistency of the molar absorbance over 2 orders of magnitude of initial concentration shows that the measured absorbance, corrected for dilution, is proportional to the bretylium concentration, as indicated.

In the second series of experiments, the procedure was tested using a solution containing the salicylate facilitating anion, but not the bretylium cation. To the second buffer solution (prepared as described above) was added a sufficient amount of sodium salicylate and tetrabutylammonium bromide to provide a 0.21 M sodium salicylate/0.12 M tetrabutylammonium bromide solution. Tetrabutylammonium bromide was used as a phase transfer agent to mimic the bretylium cation and ensure the transfer of a substantial amount of salicylate anion to the n-octanol phase. The solution was divided into 3 portions of about 0.7 g each, and 1.0 g of n-octanol was added to each of the 3 solutions. The solutions were shaken for about 30 seconds and then centrifuged at about 3000 rpm for about 5 minutes to clarify both phases. About 0.7 g of each n-octanol phase was removed and weighed and an equal weight of 5 M HCl was added to each n-octanol sample. The new 2-phase systems were shaken (about 30 seconds), and separated by centrifugation (3000 rpm for about 5 minutes) to produce clear solutions. The absorbance of these solutions at 270 mn was measured. This procedure was also carried out using the third and 4th buffer solutions (prepared as described above). The results are disclosed in Table 13C below.

TABLE 13C

| ORIGINAL pH | FINAL AQUEOUS ABSORBANCE | FINAL OCTANOL ABSORBANCE |
|---|---|---|
| 2.1 | 0.049 | 1.095 |
| 5.5 | 0.047 | 0.814 |
| 7.7 | 0.056 | 0.828 |

The sodium cation is nearly free of absorbance in the region of interest. Although the salicylate anion and salicylic acid absorb light in the ultraviolet region, they do not exhibit absorption maxima at or near the 270 nm absorption region of the bretylium cation. The results reported in Table 13C indicate that only about 5 to 6% of the salicylate anion/salicylic acid is transferred to the final aqueous HCl solutions. The absorbance at 270 nm resulting from the transferred salicylate anion/salicylic acid is not materially significant when compared to the absorbance measured for the bretylium cation using the procedure discussed above. The combination of minimal absorbance at 270 nm and the extraction of salicylic acid into the octanol phase ensures that salicylate does not materially interfere with the determination of the bretylium concentration in accordance with the procedure described above.

Example 14
Effect of Facilitating Anion Concentration on the Partition Coefficient The procedure of Example 13 was repeated for the di(2-ethylhexyl)sulfosuccinate and salicylate facilitating anions using 2 moles of facilitating anions per mole of bretylium tosylate instead of equimolar amounts as in Example 13. The partition coefficient results obtained are set forth in Table 14A below:

TABLE 14A

| NOMINAL pH | FACILITATING ANION | PARTITION COEFFICIENT |
|---|---|---|
| 0.8 | di(2-ethylhexyl)sulfosuccinate | 3.58 |
| 2.2 | di(2-ethylhexyl)sulfosuccinate | 4.98 |
| 5.6 | di(2-ethylhexyl)sulfosuccinate | 4.94 |
| 7.0 | di(2-ethylhexyl)sulfosuccinate | 5.03 |
| 0.8 | salicylate | 1.06 |
| 2.2 | salicylate | 1.52 |
| 5.5 | salicylate | 1.61 |
| 7.0 | salicylate | 2.36 |

These results indicate that increasing the molar ratio of facilitating anion to bretylium cation can materially increase the value of the partition coefficient.

Example 15
Effect of the Facilitating Anion on Bretylium Efficacy

The increase in efficacy and bioavailability of the bretylium cation afforded by the formulations of the present invention was tested by orally administering formulations containing bretylium cations and di(2-ethylhexylsulfosuccinate) anions to male beagle dogs weighing approximately 10 kg, and subsequently measuring the ventricular fibrillation threshold (VFT), effective ventricular refractory period (EVRP), and rate-corrected Q-$T_c$ interval of the dogs.

A formulation was orally administered to each dog in 3 divided doses in capsule form (i.e., conventional gelatin capsule). Each capsule contained 120 mg of bretylium tosylate; 120 mg of sodium di(2-ethylhexylsulfosuccinate); and 300 mg of sodium bicarbonate. The 3 capsules were administered to each dog over a period of 8 hours to achieve a bretylium tosylate total loading dose of approximately 36 mg per kg of body weight. The second capsule was administered 4 hr after the first capsule, and the third capsule was administered 8 hr after the first capsule.

Ten hours after administration of the first capsule, each dog was anesthetized by injection with 300 mg/kg pentabarbital (animal hospital supply grade). Additional doses of pentabarbital were administered as needed when the dogs started to awaken. The heart of each dog was exposed via an intercoastal approach, and the pericardium was opened. Stimulating bipolar silver-silver-chloride electrodes embedded in epoxy and recording electrodes were sewn to the right ventricular surface of each dog. The femoral artery was canulated to measure blood pressure.

The ventricular fibrillation threshold, effective ventricular refractory period, and rate-corrected $Q$-$T_c$ interval of each dog were measured at various times during the 10-hour interval after administration of the third capsule. Electrical ventricular fibrillation thresholds were determined using a Grass Instruments Company constant current unit to initiate a gated train of 60 Hertz impulses of 2 millisecond duration via the pair of stimulating electrodes sewn into the surface of the right ventricle. The current train began immediately after ventricular activation to cover the vulnerable period during which ventricular fibrillation can be electrically induced. The stimulus strength began at 0.25 mamp, and was increased in 0.25 mamp steps until sustained ventricular fibrillation was induced. The heart was then electrically defibrillated. Subsequently, at least 1 hr was allowed for recovery and drug actions to increase before the ventricular fibrillation threshold was measured again. After each ventricular fibrillation threshold, the effective ventricular refractory period was determined. The rate-corrected $Q$-$T_c$ interval was measured from the electrocardiogram. Effective ventricular refractory period was determined by establishing the earliest time that a stimulus delivered after ventricular activation could elicit another contraction. Rate-corrected $Q$-$T_c$ interval was measured from a high speed electrocardiographic trace.

The ventricular fibrillation threshold, effective ventricular refractory period, and rate-corrected $Q$-$T_c$ interval values measured in the dogs are set forth in Table 15A:

TABLE 15A

| SUBJECT | TIME AFTER LAST DOSE (hr) | VFT (mamp) | EVRP (msec) | RATE-CORRECTED $Q$-$T_c$ INTERVAL (sec) |
|---|---|---|---|---|
| Untreated Dog (Average Value) | N/A | 0.5 | 135 | 270 |
| Dog 1: | 2.75 | >5.0 (5.0 mamp was the maximum available current) | 205 | 408[1] |
|  | 5 | 4.25 | 223 | 388[1] |
|  | 8 | 3.0[1] | 220 | 380[1] |
|  | 10 | 2.45[1] | 224 | 374[1] |
| Dog 2: | 2 | >5.0 | 219 | 400 |
|  | 5 | 4.0[1] | 208 | 388[1] |
|  | 10 | 2.5[1] | 224 | 374[1] |

[1]Easy to defibrillate with one low current shock

These results show an increase in ventricular fibrillation threshold for the dogs, and, therefore, confirm that the formulations of the present invention increase the bioavailability of orally administered bretylium tosylate. In fact, fibrillation of the heart of the dogs could not be induced until about 6 hr after administration of the third loading dose capsule. After about 6 hr, the heart could be fibrillated with a 5.0 mamp current train, but spontaneously defibrillated either once the current train was terminated or after a single low current defibrillation shock was applied. The time interval over which the increase in ventricular fibrillation threshold, effective ventricular refractory period, and rate-corrected $Q$-$T_c$ interval was observed further suggests that a once or twice-a-day dosage of the formulations can suffice after the therapeutic concentration has been taken up by the binding sites in the heart.

Example 16

Effect of Various the Facilitating Anion on Bretylium Efficacy

The increase in efficacy and bioavailability of the bretylium cation afforded by the formulations of the present invention were further tested by orally administering either 1 or 2 doses of various bretylium-tosylate/facilitating-anion combinations (all containing roughly an equimolar amount of bretylium tosylate and the facilitating anion), and then measuring the ventricular fibrillation threshold of the dogs at various times following the oral administration.

Mongrel dogs of either sex and weighing 10 to 40 kg were used. The dogs were anesthetized with isofluorine gas and respired with a Harvard respirator using room air. A catheter electrode was passed under fluoroscopic observation via the jugular vein into the apex of the right ventricle and screwed into place in the myocardium of the right ventricle.

The ventricular fibrillation threshold (VFT) was determined using a Grass Instruments Company constant current unit to initiate a gated train of 60 Hertz impulses of 1 millisecond duration. The current train began immediately after ventricular activation and was sustained long enough to cover the vulnerable period during which ventricular fibrillation can be electrically induced. The stimulus strength began at 5 mamp, and was increased in 3–4 mamp steps until sustained ventricular fibrillation was induced (or until the maximum current of 50 mamp was applied). The effective ventricular refractory period (EVRP) was measured using the method of Example 15.

After the control VFT and EVRP were measured, the compositions were orally administered in capsule form via a stomach tube. Here, the capsule was pushed by a rod into the stomach tube, and then washed into the stomach with 50 ml glucose delivered through the stomach tube. The VFT and EVRP were measured at various times following this administration. In some instances (i.e., Dogs 1, 3, & 4) a second oral dose was also given 12 hours after the first dose.

Table 16A shows the results ("BT" means bretylium tosylate, "NaS" means sodium salicylate, "NaLS" means sodium lauryl sulfate, "VFT" means ventricular fibrillation threshold, and "EVRP" means effective ventricular refractory period). The effects of the bretylium were observed within 10 minutes of oral administration of the compositions. In addition, within 30 minutes of oral administration, the ventricular fibrillation threshold generally increased significantly. And, in many instances, the subject dogs eventually could not be fibrillated at all, even at the maximum current of the generator (VFT values of greater than 50 mamp in Table 16A represent instances where the subject could not be fibrillated at the maximum current (i.e., 50 mamp) of the generator). This effect on the ventricular fibrillation threshold generally continued over the entire 29 hour measuring period, thus suggesting that one dosage per day of these compositions is sufficient.

TABLE 16A

| Subject | VFT Before Drug Dose (mamp) | EVRP Before Drug Dose (msec) | First Drug Dose (per kg dog) | Second Drug Dose (administered at 12 hr after first drug dose) (per kg dog) | VFT After Drug Dose (VFT (mamp); % increase in VFT;time of measurement after first drug dose) | EVRP After Drug Dose (EVRP (msec);time of measurement after first drug dose) |
|---|---|---|---|---|---|---|
| Dog 1 | 27 | 101 | 15 mg BT 10 mg NaLS | 10 mg BT 7 mg NaLS | >50;>85%;24 hr | 195;24 hr |
| Dog 2 | 13 | 150 | 20 mg BT 14 mg NaLS | No Second Dose | 26;100%;1.25 hr | 130;1 hr |
| Dog 3 | 5 | 105 | 15 mg BT 10 mg NaLS | 5 mg BT 10 mg NaLS | 19;280%;2 hr 34;580%;24 & 25 hr 36;620%;25.5 hr 33;560%;26 hr | 125;30 min 134;1.4 hr 138;2 hr 141;3 hr 132;24 hr 130;25 hr 138;25.5 hr 135;26 hr |
| Dog 4 | 19 | 98 | 15 mg BT 10 mg NaLS | 5 mg BT 5 mg NaLS | >50;>163%;2 hr 36;89%;24.5 hr >50;>163%;26 & 27 hr | 104;30 min 110;1 hr 108;1.5 hr 112;2 hr 128;24.5 hr 111;26 hr 112;27 hr |
| Dog 5 | 16 | 96 | 15 mg BT 6 mg NaS | No Second Dose | >50;>213%;2.3 & 24 hr | 107;40 min 101;2.3 hr 118;24 hr |
| Dog 6 | 15 | 100 | 15 mg BT 6 mg NaS | No Second Dose | >50;>233%;30 min & 24 hr | 124;13 min 150;24 hr |
| Dog 7 | 27 | 115 | 15 mg BT 6.5 mg aspirin | No Second Dose | >50;>85%;10 min, 1 hr, 2.5 hr, & 29 hr | 125;10 min 132;1 hr 140;1.5 hr 131;29 hr |
| Dog 8 | 11 | 95 | 15 mg BT 6.5 mg aspirin | No Second Dose | 48;336%;10 min >50;>355%;15 min, 23 hr, & 23.25 hr | 90;3 min 97;5 min 97;10 min 105;15 min 113;23 hr 116;23.25 hr |
| Dog 9 | 11 | 148 | 15 mg BT 6.5 mg aspirin | No Second Dose | 23;109%;15 min 36;228%;30 min 35;218%;1 hr | 150;15 min 138;30 min 140;1 hr |
| Dog 10 | 12 | 145 | 15 mg BT 6.5 mg aspirin | No Second Dose | 49;308%;1 hr >50;>317%;3 & 24 hr | 155;1 hr 155;3 hr 126;24 hr |
| Dog 11 | 11 | 164 | 15 mg BT 6.5 mg aspirin | No Second Dose | 12;9%;22 min >50;>355%;2.25 & 25 hr | 165;22 min 205;2.25 hr 152;25 hr |
| Dog 12 | 25 | 102 | 15 mg BT 6.5 mg aspirin | No Second Dose | >50;>100%;40 min & 24.7 hr | 102;40 min 107;24.7 hr |

Example 17
The Effect of the Compositions of this Invention on Atrial Fibrillation The effect of the compositions of this invention on atrial fibrillation was observed using a mongrel dog weighing approximately 35 kg. Atrial fibrillation was initially induced by a stimulating bipolar electrode catheter (to position this catheter electrode, it was passed into the right atrium via the jugular vein under fluoroscopic observation and then screwed into place in the myocardium of the right atrium). This electrode catheter delivered stimulating shocks consisting of a train of square wave pulses of 1 msec duration at 60 Hz. Atrial fibrillation was induced at a current of 6 mamp.

Defibrillation was first attempted using a single dose of bretylium tosylate (Arnar-Stone, McGaw Park, Ill.) administered intravenously (the dose corresponded to 15 mg of bretylium tosylate per kg of the recipient). No effect on atrial fibrillation was observed.

Subsequently, a composition containing bretylium tosylate and aspirin was administered intravenously. This composition was prepared using a commercially available tablet containing aspirin. The aspirin tablet was dissolved in warm water and filtered through a fine surgical gauze pad (to remove the bulk of the binder in the tablet). The resulting aspirin filtrate was then combined with an approximately equimolar amount of bretylium tosylate dissolved in 5% dextrose in water. Approximately 20 ml of this aqueous solution was injected into the atrially fibrillating dog (this dose corresponded to roughly 15 mg of bretylium tosylate per kg of the recipient and 6.5 mg of aspirin per Kg recipient). FIG. 1 shows the electrocardiogram for the dog following this administration. As can be seen, the atrial fibrillation was eliminated within 50 seconds of the administration. And the fibrillation subsequently could not be re-induced even at the maximum generator current of 50 mamp.

Example 18
Effect of β-Receptor Blocker on Bretylium Efficacy

The increase in efficacy of the bretylium cation afforded by administering the bretylium cation in combination with a β-receptor blocker was tested by administering via injection bretylium tosylate alone, various β-receptor blockers alone, and various combinations of bretylium tosylate and β-receptor blockers to dogs, and then measuring the ventricular fibrillation threshold of the dogs 1–5 hours after drug administration. Table 18A shows the results.

TABLE 18A

| Drug Administered (per kg of recipient dog) | Mean % Increase in VFT |
|---|---|
| 20 mg bretylium tosylate no β-receptor blocker | 100–200% (no standard deviation calculated) |
| 0.075 mg propranolol no bretylium | 110% ± 40% |
| 0.05 mg propranolol 20 mg bretylium tosylate | 320% ± 180% |
| 0.075 mg propranolol 10 mg bretylium tosylate | 540% ± 360% |
| 0.25 mg propranolol 20 mg bretylium tosylate | 310% ± 70% |
| 0.05 mg atenolol no bretylium | 330% ± 210% |
| 0.025 to 0.1 mg atenolol 20 mg bretylium tosylate | 550% ± 430% |
| 0.05 mg metoprolol no bretylium | 96% ± 70% |
| 0.035 mg metoprolol 10 mg bretylium tosylate | 410% ± 180% |
| 0.05 mg metoprolol 10 mg bretylium tosylate | 410% ± 190% |
| 0.035 to 0.1 mg metoprolol 10 mg bretylium tosylate | 370% ± 200% |
| 25 to 300 µg esmolol no bretylium | no significant increase |
| 200 µg esmolol 10 mg bretylium tosylate | 380% ± 150% |
| 25 µg esmolol 10 mg bretylium tosylate | 290% ± 110% |
| 25 µg esmolol 20 mg bretylium tosylate | 350% ± 180% |
| 300 µg esmolol 10 mg bretylium tosylate | 300% ± 190% |

In another experiment, the effect of a β-receptor blocker on the timing and efficacy of the bretylium cation was observed:

Control #1: Administration of Bretylium Tosylate Alone

When bretylium tosylate alone was intravenously administered (using a dose of about 20 mg of bretylium tosylate per kg of canine recipient), a substantial increase in the ventricular fibrillation threshold began at 12–15 minutes after administration. About 3 hours after administration, this increase peaked at roughly 30 to 90 mamp, i.e., about 100 to 200% greater than the ventricular fibrillation threshold where no bretylium was administered at all (i.e., roughly 10 to 30 mamp).

Control #2: Administration of Propranolol Alone

When propranolol alone was intravenously administered (using a dose of 0.05 to 0.5 mg/kg), there was a 110%±40% increase in the ventricular fibrillation threshold.

Administration of Bretylium Tosylate and Propranolol

When a combination of bretylium tosylate and propranolol was intravenously administered (using a dose of 20 mg/kg bretylium tosylate and 0.05 to 0.2 mg/kg propranolol) to 10 dogs, the ventricular fibrillation threshold increased to greater than 100 mamp (the maximum current generator output) within 3 to 10 minutes of the administration, and the hearts of all 10 dogs remained non-fibrillatable for the entire 6 hour study period after the administration.

The above description of the preferred embodiments and the accompanying figure are intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

All patent documents and other literature references cited in this specification are hereby incorporated herein by reference.

We claim:

1. A pharmaceutical combination useful for preventing and/or treating a cardiovascular condition, said pharmaceutical combination comprising:
   a bretylium cation or a source of a bretylium cation,
   a facilitating anion or a source of a facilitating anion, and
   an anti-hypotensive agent and/or a β-receptor blocker or a source of an anti-hypotensive agent and/or a β-receptor blocker, wherein:
   said facilitating anion is less hydrophilic than a tosylate anion; and
   said bretylium cation or said source of a bretylium cation, said facilitating anion or said source of a facilitating anion, and said anti-hypotensive agent and/or said β-receptor blocker or said source of an anti-hypotensive agent and/or a β-receptor blocker together are present in said pharmaceutical combination in a therapeutically effective amount.

2. A pharmaceutical combination as set forth in claim 1 wherein said combination comprises a pharmaceutical composition comprising:
   a bretylium cation,
   a facilitating anion, and
   an anti-hypotensive agent and/or a β-receptor blocker, wherein:
   said facilitating anion is less hydrophilic than a tosylate anion; and
   said bretylium cation, said facilitating anion, and said anti-hypotensive agent and/or said β-receptor blocker together are present in said pharmaceutical composition in a therapeutically effective amount.

3. A pharmaceutical combination as set forth in claim 2, wherein said combination further comprises a neutralizing agent.

4. A pharmaceutical combination as set forth in claim 3, wherein said neutralizing agent comprises sodium bicarbonate.

5. A pharmaceutical combination as set forth in claim 2, wherein said combination further comprises a buffering agent.

6. A pharmaceutical combination as set forth in claim 2, wherein said combination further comprises citric acid.

7. A pharmaceutical combination as set forth in claim 2, wherein said combination comprises an anti-hypotensive agent.

8. A pharmaceutical combination as set forth in claim 7, wherein said anti-hypotensive agent comprises a tricyclic anti-depressant compound.

9. A pharmaceutical combination as set forth in claim 7, wherein said anti-hypotensive agent is selected from the group consisting of protriptyline, amitriptyline, nortriptyline, desipramine and mazindol.

10. A pharmaceutical combination as set forth in claim 2, wherein said combination comprises a β-receptor blocker.

11. A pharmaceutical combination as set forth in claim 10, wherein said β-receptor blocker is selected from the group consisting of propranolol, atenolol, esmolol, metoprolol, labetalol, talinolol, timolol, acebutolol, carvedilol, dichloroisoproterenol, pronethalol, sotalol, oxprenolol, alprenolol, practolol, nadolol, penbutolol, carteolol, and pindolol.

12. A pharmaceutical combination as set forth in claim 2, wherein said facilitating anion has an organic/aqueous phase distribution equilibrium constant of greater than about 320 when introduced into a mixture comprising water, 1-decanol, methyltridecylammonium chloride, and a methyltridecylammonium salt.

13. A pharmaceutical combination as set forth in claim 2, wherein, when the components of said combination are orally administered to a human, the area under a plot of the bretylium cation concentration in said human's myocardium versus time over about 24 hours following said oral administration is greater than the area under a plot of the bretylium cation concentration in the myocardium versus time over about 24 hours following an oral administration of bretylium tosylate in an amount which supplies an equivalent amount of the bretylium cation as is supplied by said oral administration of said pharmaceutical combination.

14. A pharmaceutical combination as set forth in claim 2, wherein said combination comprises at least 2 types of facilitating anions.

15. A pharmaceutical combination as set forth in claim 2, wherein said facilitating anion comprises an anion selected from the group consisting of alkylsulfate, alkylsulfonate, alkylsulfosuccinate, salicylate, alkylsalicylate, alkylphosphate, dialkylphosphate, and dialkanoylphosphatidate.

16. A pharmaceutical combination as set forth in claim 2, wherein said combination comprises a compound which comprises both said bretylium cation and said facilitating anion.

17. A pharmaceutical combination as set forth in claim 2, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

18. A pharmaceutical combination as set forth in claim 2, wherein said combination comprises (a) a compound which comprises said bretylium cation, and (b) another compound which comprises said facilitating anion.

19. A pharmaceutical combination as set forth in claim 2, wherein said combination further comprises at least 3 compounds selected from the group consisting of a neutralizing agent, a buffering agent, an anti-hypotensive agent, and a β-receptor blocker.

20. A pharmaceutical combination as set forth in claim 2, wherein said combination further comprises a neutralizing agent, a buffering agent, an anti-hypotensive agent, and a β-receptor blocker.

21. A pharmaceutical combination as set forth in claim 2, wherein said combination is in a form comprising a tablet or a capsule.

22. A pharmaceutical combination as set forth in claim 2, wherein said combination is in a form comprising a solution or suspension.

23. A pharmaceutical combination as set forth in claim 2, wherein said combination is in a form suitable for administering via injection.

24. A pharmaceutical combination as set forth in claim 23, wherein said combination is suitable for intravenous or intramuscular injection.

25. A pharmaceutical combination as set forth in claim 23 further comprising a buffer.

26. A pharmaceutical combination as set forth in claim 25 further comprising a bulking, dispersing, wetting or suspending agent.

27. A pharmaceutical combination as set forth in claim 23 further comprising eplerenone.

28. A pharmaceutical combination as set forth in claim 2, wherein said combination comprises a pharmaceutical composition comprising:
   0.5% to 60% bretylium cation,
   0.3% to 60% facilitating anion,
   0.0% to 0.5% anti-hypotensive agent,
   0.0% to 1.0% β-receptor blocker, and
   0.02% to 99% neutralizing agent.

29. A pharmaceutical combination as set forth in claim 1, wherein said combination comprises a pharmaceutical kit comprising:
   a source of a bretylium cation,
   a source of a facilitating anion, and
   a source of an anti-hypotensive agent and/or a β-receptor blocker, wherein:
      said facilitating anion is less hydrophilic than a tosylate anion; and
      said source of bretylium cation, said source of facilitating anion, and said source of anti-hypotensive agent and/or β-receptor blocker together are present in said pharmaceutical kit in a therapeutically effective amount.

30. A pharmaceutical combination as set forth in claim 29, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising said anti-hypotensive agent, and/or said β-receptor blocker.

31. A pharmaceutical combination as set forth in claim 29, wherein said combination comprises a pharmaceutical kit comprising at least three separate unit dosages, said unit dosages being (a) a unit dosage comprising said bretylium cation, (b) a unit dosage comprising said facilitating anion, and (c) a unit dosage comprising a neutralizing agent and said anti-hypotensive agent, and/or said β-receptor blocker.

32. A pharmaceutical combination useful for preventing and/or treating a cardiovascular condition, said pharmaceutical combination comprising:
   a bretylium cation or a source of a bretylium cation, and
   a facilitating anion or a source of a facilitating anion, wherein:
      said facilitating anion is less hydrophilic than a tosylate anion;
      said bretylium cation or said source of bretylium cation and said facilitating anion or said source of facilitating anion are, in combination, suitable for oral ingestion;
      said bretylium cation or said source of bretylium cation and said facilitating anion or said source of facilitating anion are capable of forming a mixture comprising both a bretylium cation and a facilitating anion within the gastrointestinal tract of a subject upon ingestion by said subject;
      said bretylium cation or said source of bretylium cation and said facilitating anion or said source of facilitating anion together are present in said pharmaceutical combination in a therapeutically effective amount; and
      when the components of said pharmaceutical combination are orally administered to a human, the area under a plot of the bretylium cation concentration in said human's myocardium versus time over about 30 minutes following said oral administration is greater than the area under a plot of the bretylium cation concentration in the myocardium versus time over about 30 minutes following an oral administration of bretylium tosylate in an amount which supplies an equivalent amount of the bretylium cation as is supplied by said oral administration of the components of said pharmaceutical combination.

33. A pharmaceutical combination as set forth in claim 32 wherein said combination comprises a pharmaceutical composition comprising a bretylium cation and a facilitating anion, wherein:

said facilitating anion is less hydrophilic than a tosylate anion;

said pharmaceutical composition is suitable for oral ingestion;

said pharmaceutical composition is capable of forming a mixture comprising both a bretylium cation and a facilitating anion within the gastrointestinal tract of a subject upon ingestion by said subject;

said bretylium cation and said facilitating anion together are present in said pharmaceutical composition in a therapeutically effective amount; and when said pharmaceutical composition is orally administered to a human, the area under a plot of the bretylium cation concentration in said human's myocardium versus time over about 30 minutes following said oral administration is greater than the area under a plot of the bretylium cation concentration in the myocardium versus time over about 30 minutes following an oral administration of bretylium tosylate in an amount which supplies an equivalent amount of the bretylium cation as is supplied by said oral administration of said pharmaceutical composition.

34. A pharmaceutical combination as set forth in claim 33, wherein said combination further comprises a neutralizing agent.

35. A pharmaceutical combination as set forth in claim 33, wherein said combination further comprises a buffering agent.

36. A pharmaceutical combination as set forth in claim 33, wherein said combination further comprises an anti-hypotensive agent.

37. A pharmaceutical combination as set forth in claim 33, wherein said combination further comprises a β-receptor blocker.

38. A pharmaceutical combination as set forth in claim 33, wherein said combination comprises a compound which comprises both said bretylium cation and said facilitating anion.

39. A pharmaceutical combination as set forth in claim 33, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

40. A pharmaceutical combination as set forth in claim 33, wherein said combination comprises (a) a compound which comprises said bretylium cation, and (b) another compound which comprises said facilitating anion.

41. A pharmaceutical combination as set forth in claim 32 wherein said combination comprises a pharmaceutical kit comprising a source of a bretylium cation and a source of a facilitating anion, wherein:

said facilitating anion is less hydrophilic than a tosylate anion;

said source of said bretylium cation and said source of said facilitating anion are, in combination, suitable for oral ingestion;

said source of said bretylium cation and said source of said facilitating anion are capable of forming a mixture comprising both said bretylium cation and said facilitating anion within the gastrointestinal tract of a subject upon ingestion by said subject;

said source of bretylium cation and said source of facilitating anion together are present in said pharmaceutical kit in a therapeutically effective amount; and when the components contained in said pharmaceutical kit are orally administered to a human, the area under a plot of the bretylium cation concentration in said human's myocardium versus time over about 30 minutes following said oral administration is greater than the area under a plot of the bretylium cation concentration in the myocardium versus time over about 30 minutes following an oral administration of bretylium tosylate in an amount which supplies an equivalent amount of the bretylium cation as is supplied by said oral administration of the components of said pharmaceutical kit.

42. A pharmaceutical combination as set forth in claim 41, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

43. A pharmaceutical combination useful for preventing and/or treating a cardiovascular condition, said pharmaceutical combination comprising:

a bretylium cation or a source of a bretylium cation, and a facilitating anion or a source of a facilitating anion, wherein:

said facilitating anion is less hydrophilic than a tosylate anion;

said bretylium cation or said source of bretylium cation and said facilitating anion or said source of facilitating anion are, in combination, suitable for oral ingestion;

said bretylium cation or said source of bretylium cation and said facilitating anion or said source of facilitating anion are capable of forming a mixture comprising both a bretylium cation and a facilitating anion within the gastrointestinal tract of a subject upon ingestion by said subject;

said bretylium cation or said source of bretylium cation and said facilitating anion or said source of facilitating anion together are present in said pharmaceutical combination in a therapeutically effective amount; and when the components of said pharmaceutical combination are orally administered to a human, the area under a plot of the bretylium cation concentration in said human's blood versus time over about 30 minutes following said oral administration is greater than the area under a plot of the bretylium cation concentration in the blood versus time over about 30 minutes following an oral administration of bretylium tosylate in an amount which supplies an equivalent amount of the bretylium cation as is supplied by said oral administration of the components of said pharmaceutical combination.

44. A pharmaceutical combination as set forth in claim 43 wherein said combination comprises a pharmaceutical composition comprising a bretylium cation and a facilitating anion, wherein:
   said pharmaceutical composition is suitable for oral ingestion;
   said pharmaceutical composition is capable of forming a mixture comprising both said bretylium cation and said facilitating anion within the gastrointestinal tract of a subject upon ingestion by said subject;
   said bretylium cation and said facilitating anion together are present in said pharmaceutical composition in a therapeutically effective amount; and
   when said pharmaceutical composition is orally administered to a human, the area under a plot of the bretylium cation concentration in said human's blood versus time over about 30 minutes following said oral administration is greater than the area under a plot of the bretylium cation concentration in the blood versus time over about 30 minutes following an oral administration of bretylium tosylate in an amount which supplies an equivalent amount of the bretylium cation as is supplied by said oral administration of said pharmaceutical composition.

45. A pharmaceutical combination as set forth in claim 44, wherein said combination further comprises a neutralizing agent.

46. A pharmaceutical combination as set forth in claim 44, wherein said combination further comprises a buffering agent.

47. A pharmaceutical combination as set forth in claim 44, wherein said combination further comprises an anti-hypotensive agent.

48. A pharmaceutical combination as set forth in claim 44, wherein said combination further comprises a β-receptor blocker.

49. A pharmaceutical combination as set forth in claim 44, wherein said combination comprises a compound which comprises both said bretylium cation and said facilitating anion.

50. A pharmaceutical combination as set forth in claim 44, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

51. A pharmaceutical combination as set forth in claim 44, wherein said combination comprises (a) a compound which comprises said bretylium cation, and (b) another compound which comprises said facilitating anion.

52. A pharmaceutical combination as set forth in claim 43 wherein said combination comprises a pharmaceutical kit comprising a source of a bretylium cation and a source of a facilitating anion, wherein:
   said source of bretylium cation and said source of facilitating anion are, in combination, suitable for oral ingestion;
   said source of bretylium cation and said source of facilitating anion are capable of forming a mixture comprising both said bretylium cation and said facilitating anion within the gastrointestinal tract of a subject upon ingestion by said subject;
   said source of bretylium cation and said source of facilitating anion together are present in said pharmaceutical kit in a therapeutically effective amount; and
   when the components contained in said pharmaceutical kit are orally administered to a human, the area under a plot of the bretylium cation concentration in said human's blood versus time over about 30 minutes following said oral administration is greater than the area under a plot of the bretylium cation concentration in the blood versus time over about 30 minutes following an oral administration of bretylium tosylate in an amount which supplies an equivalent amount of the bretylium cation as is supplied by said oral administration of the components contained in said pharmaceutical kit.

53. A pharmaceutical combination as set forth in claim 52, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

54. A pharmaceutical combination useful for preventing and/or treating a cardiovascular condition, said pharmaceutical combination comprising:
   a bretylium cation or a source of a bretylium cation; and
   a facilitating anion or a source of a facilitating anion,
   said facilitating anion being selected from the group consisting of:
   $R^2SO_3^-$,

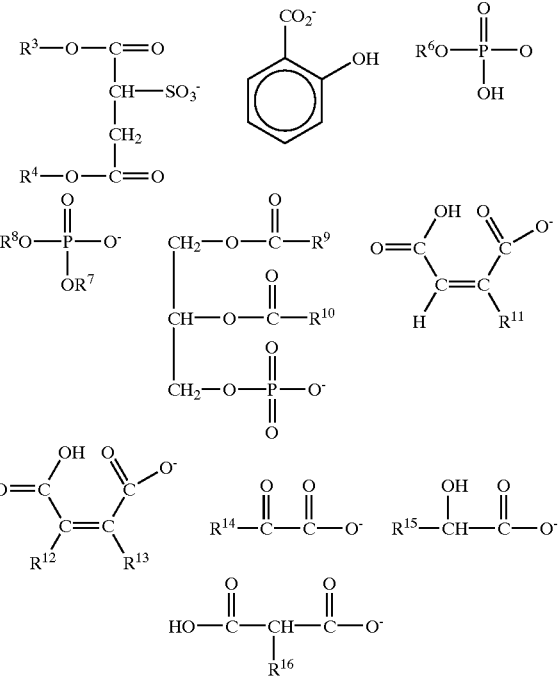

a pseudo-icosahedral carborane anion ($CB_{11}H_{12}^-$), and a substituted pseudo-icosahedral carborane anion, wherein:
   $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, and the substituent(s) of the substituted pseudo-icosahedral carborane anion are independently hydrocarbyl or substituted hydrocarbyl; and
   said bretylium cation or said source of a bretylium cation and said facilitating anion or said source of a facilitating anion together are present in said pharmaceutical combination in a therapeutically effective amount.

55. A pharmaceutical combination as set forth in claim 54 wherein said combination comprises a pharmaceutical composition comprising a bretylium cation and a facilitating anion selected from the group consisting of:

$R^2SO_3^-$,

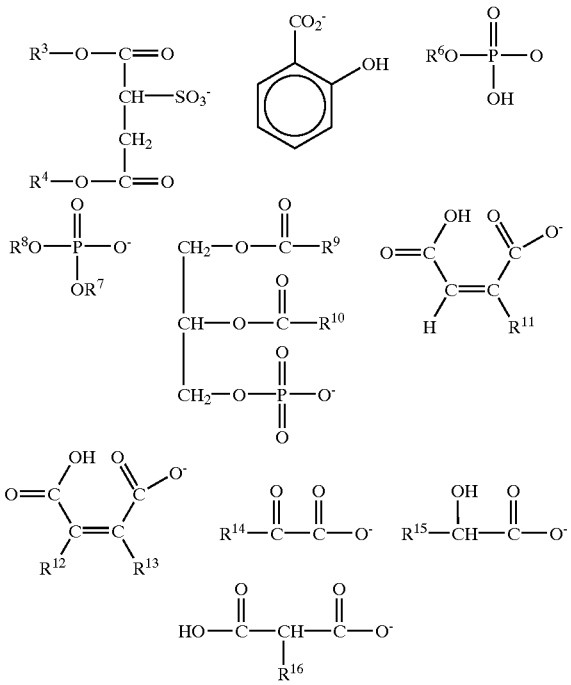

a pseudo-icosahedral carborane anion ($CB_{11}H_{12}^-$), and
a substituted pseudo-icosahedral carborane anion,
wherein:
$R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, and the substituent(s) of the substituted pseudo-icosahedral carborane anion are independently hydrocarbyl or substituted hydrocarbyl; and
said bretylium cation and said facilitating anion together are present in said pharmaceutical composition in a therapeutically effective amount.

56. A pharmaceutical combination as set forth in claim 55, wherein $R^2$, $R^3$, $R^4$, $R^6$, $R^7$, $R^8$, $R^9$, $R^{10}$, $R^{11}R^{12}$, $R^{13}$, $R^{14}$, $R^{15}$, $R^{16}$, and the substituent(s) of the substituted pseudo-icosahedral carborane anion are independently hydrocarbyl.

57. A pharmaceutical combination as set forth in claim 55, wherein said combination further comprises a neutralizing agent.

58. A pharmaceutical combination as set forth in claim 57, wherein said neutralizing agent comprises sodium bicarbonate.

59. A pharmaceutical combination as set forth in claim 55, wherein said combination further comprises a buffering agent.

60. A pharmaceutical combination as set forth in claim 55, wherein said combination further comprises citric acid.

61. A pharmaceutical combination as set forth in claim 55, wherein said combination further comprises an anti-hypotensive agent.

62. A pharmaceutical combination as set forth in claim 61, wherein said anti-hypotensive agent comprises a tricyclic anti-depressant compound.

63. A pharmaceutical combination as set forth in claim 61, wherein said anti-hypotensive agent is selected from the group consisting of protriptyline, amitriptyline, nortriptyline, desipramine, and mazindol.

64. A pharmaceutical combination as set forth in claim 55, wherein said combination further comprises a β-receptor blocker.

65. A pharmaceutical combination as set forth in claim 64, wherein said β-receptor blocker is selected from the group consisting of propranolol, atenolol, esmolol, metoprolol, labetalol, talinolol, timolol, acebutolol, carvedilol, dichloroisoproterenol, pronethalol, sotalol, oxprenolol, alprenolol, practolol, nadolol, penbutolol, carteolol, and pindolol.

66. A pharmaceutical combination as set forth in claim 55, wherein said facilitating anion has an organic/aqueous phase distribution equilibrium constant of greater than about 320 when introduced into a mixture comprising water, 1-decanol, methyltridecylammonium chloride, and a methyltridecylammonium salt.

67. A pharmaceutical combination as set forth in claim 55, wherein, when the components of said combination are orally administered to a human, the area under a plot of the bretylium cation concentration in said human's myocardium versus time over about 24 hours following said oral administration is greater than the area under a plot of the bretylium cation concentration in the myocardium versus time over about 24 hours following an oral administration of bretylium tosylate in an amount which supplies an equivalent amount of the bretylium cation as is supplied by said oral administration of said pharmaceutical combination.

68. A pharmaceutical combination as set forth in claim 55, wherein said combination comprises at least 2 types of facilitating anions.

69. A pharmaceutical combination as set forth in claim 55, wherein said facilitating anion comprises an anion selected from the group consisting of alkylsulfate, alkylsulfonate, alkylsulfosuccinate, salicylate, alkylsalicylate, alkylphosphate, dialkylphosphate, and dialkanoylphosphatidate.

70. A pharmaceutical combination as set forth in claim 55, wherein said combination comprises a compound which comprises both said bretylium cation and said facilitating anion.

71. A pharmaceutical combination as set forth in claim 55, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

72. A pharmaceutical combination as set forth in claim 55, wherein said combination comprises (a) a compound which comprises said bretylium cation, and (b) another compound which comprises said facilitating anion.

73. A pharmaceutical combination as set forth in claim 55, wherein said combination further comprises at least 3 compounds selected from the group consisting of a neutralizing agent, a buffering agent, an anti-hypotensive agent, and a β-receptor blocker.

74. A pharmaceutical combination as set forth in claim 55, wherein said combination further comprises a neutralizing agent, a buffering agents an anti-hypotensive agent, and a β-receptor blocker.

75. A pharmaceutical combination as set forth in claim 55, wherein said combination is in a form comprising a tablet or a capsule.

76. A pharmaceutical combination as set forth in claim 55, wherein said combination is in a form comprising a solution or suspension.

77. A pharmaceutical combination as set forth in claim 55, wherein said combination is in a form suitable for administering via injection.

78. A pharmaceutical combination as set forth in claim 77, wherein said combination is suitable for intravenous or intramuscular injection.

79. A pharmaceutical combination as set forth in claim 77 further comprising a buffer.

80. A pharmaceutical combination as set forth in claim 79 further comprising a bulking, dispersing, wetting or suspending agent.

81. A pharmaceutical combination as set forth in claim 77 further comprising eplerenone.

82. A pharmaceutical combination as set forth in claim 54 wherein said combination comprises a pharmaceutical kit comprising a source of a bretylium cation and a source of a facilitating anion, said facilitating anion being selected from the group consisting of:

$R^2SO_3^-$, 

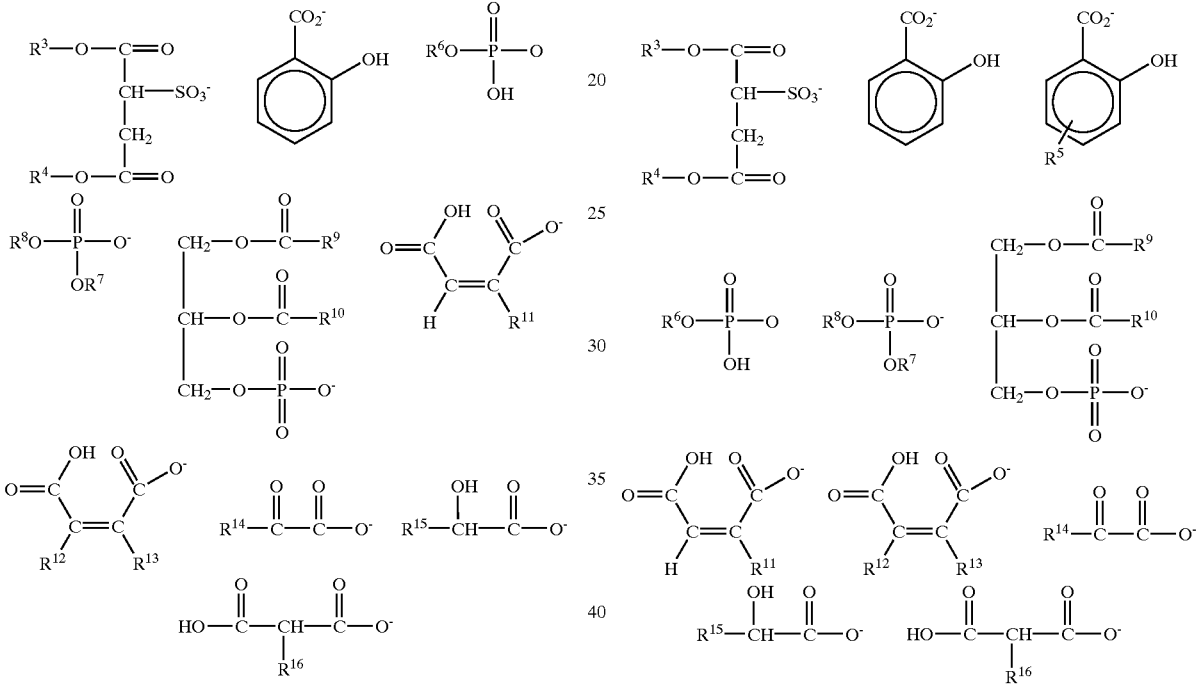

a pseudo-icosahedral carborane anion ($CB_{11}H_{12}^-$), and a substituted pseudo-icosahedral carborane anion,
wherein:
$R^2, R^3, R^4, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and
said source of bretylium cation and said source of facilitating anion are present in said kit in a therapeutically effective amount.

83. A pharmaceutical combination as set forth in claim 82, wherein $R^2, R^3, R^4, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl.

84. A pharmaceutical combination as set forth in claim 82, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

85. A pharmaceutical combination as set forth in claim 82, wherein said combination comprises a pharmaceutical kit comprising at least three separate unit dosages, said unit dosages being (a) a unit dosage comprising said bretylium cation, (b) a unit dosage comprising said facilitating anion, and (c) a unit dosage comprising a neutralizing agent.

86. A pharmaceutical combination useful for preventing and/or treating a cardiovascular condition, said pharmaceutical combination comprising:
a bretylium cation or a source of a bretylium cation; a neutralizing agent, an anti-hypotensive agent, and/or a β-receptor blocker or a source of a neutralizing agent, an anti-hypotensive agent and/or a β-receptor blocker; and
a facilitating anion or a source of a facilitating anion,
said facilitating anion being selected from the group consisting of:
$R^2SO_3^-$, 

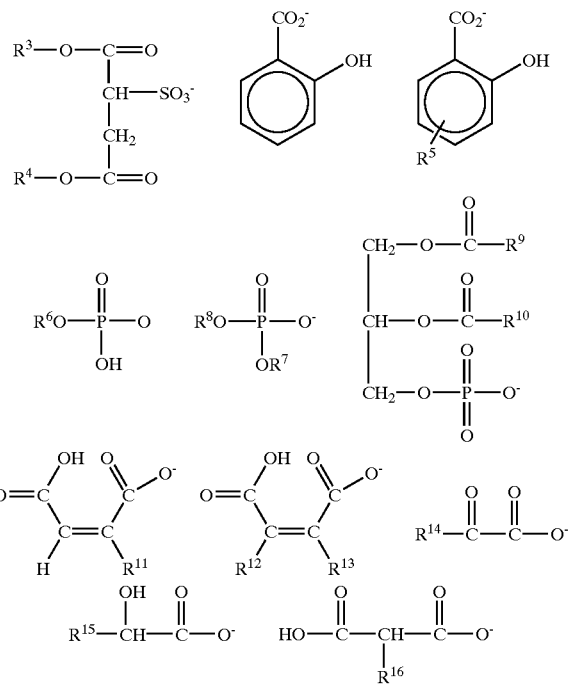

a pseudo-icosahedral carborane anion ($CB_{11}H_{12}^-$), and a substituted pseudo-icosahedral carborane anion,
wherein:
$R^2, R^3, R^4, R^5, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and
said bretylium cation or said source of bretylium cation; said facilitating anion or said source of facilitating anion; and said neutralizing agent, said anti-hypotensive agent, and/or said β-receptor blocker or said source of a neutralizing agent, an anti-hypotensive agent, and/or a β-receptor blocker together are present in said pharmaceutical combination in a therapeutically effective amount.

87. A pharmaceutical combination as set forth in claim 86 wherein said combination comprises a pharmaceutical composition comprising:
a bretylium cation;
a neutralizing agent, an anti-hypotensive agent, and/or a β-receptor blocker; and a facilitating anion selected from the group consisting of:
$R^2SO_3^-$,

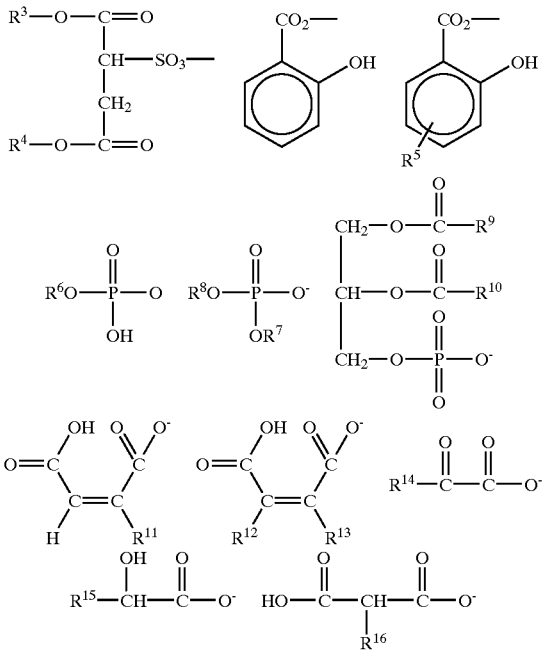

a pseudo-icosahedral carborane anion ($CB_{11}H_{12}^-$), and a substituted pseudo-icosahedral carborane anion,
wherein:
$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and the substituent(s) of the substituted pseudo-icosahedral carborane anion are independently hydrocarbyl or substituted hydrocarbyl; and said bretylium cation; said facilitating anion; and said neutralizing agent, anti-hypotensive agent, and/or β-receptor blocker are present in said pharmaceutical composition in a therapeutically effective amount.

88. A pharmaceutical combination as set forth in claim 87, wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and and the substituent(s) of the substituted pseudo-icosahedral carborane anion are independently hydrocarbyl.

89. A pharmaceutical combination as set forth in claim 87, wherein said combination further comprises a neutralizing agent.

90. A pharmaceutical combination as set forth in claim 87, wherein said combination further comprises a buffering agent.

91. A pharmaceutical combination as set forth in claim 87, wherein said combination further comprises an anti-hypotensive agent.

92. A pharmaceutical combination as set forth in claim 87, wherein said combination further comprises a β-receptor blocker.

93. A pharmaceutical combination as set forth in claim 87, wherein said combination comprises a compound which comprises both said bretylium cation and said facilitating anion.

94. A pharmaceutical combination as set forth in claim 87, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

95. A pharmaceutical combination as set forth in claim 87, wherein said combination comprises (a) a compound which comprises said bretylium cation, and (b) another compound which comprises said facilitating anion.

96. A pharmaceutical combination as set forth in claim 86 wherein said combination comprises a pharmaceutical kit comprising:
a source of a bretylium cation;
a source of a neutralizing agent, an anti-hypotensive agent, and/or a β-receptor blocker; and
a source of a facilitating anion,
said facilitating anion being selected from the group consisting of:
$R^2SO_3^-$,

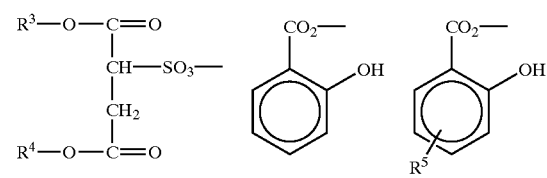

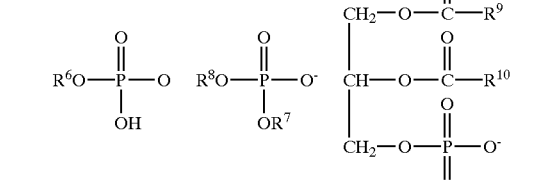

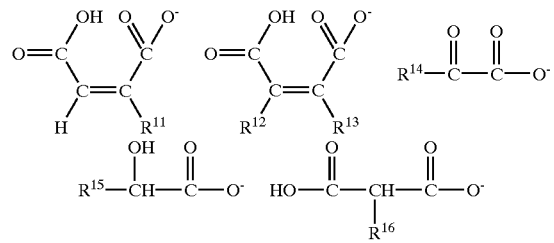

pseudo-icosahedral carborane anion ($CB_{11}H_{12}^-$), and a substituted pseudo-icosahedral carborane anion,
wherein:
$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and the substituent(s) of the substituted pseudo-icosahedral carborane anion are independently hydrocarbyl or substituted hydrocarbyl; and said source of a bretylium cation, said source of a facilitating anion, and said source of a neutralizing agent, anti-hypotensive agent, and/or β-receptor blocker together are present in said kit in a therapeutically effective amount.

97. A pharmaceutical combination as set forth in claim 96, wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and the substituent(s) of the substituted pseudo-icosahedral carborane anion are independently hydrocarbyl.

98. A pharmaceutical combination as set forth in claim 96, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

99. A pharmaceutical combination useful for preventing and/or treating a cardiovascular condition, said pharmaceutical combination comprising:

a bretylium cation or a source of a bretylium cation; and a facilitating anion or a source of a facilitating anion, said facilitating anion being selected from the group consisting of:

$R^2SO_3^-$,

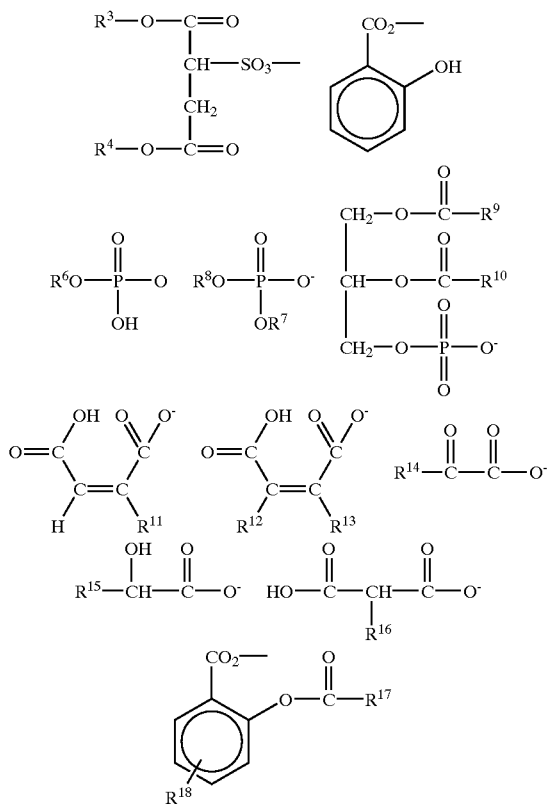

a pseudo-icosahedral carborane anion ($CB_{11}H_{12}^-$), and a substituted pseudo-icosahedral carborane anion, wherein:

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and the substituent(s) of the substituted pseudo-icosahedral carborane anion are independently hydrocarbyl or substituted hydrocarbyl;

$R^{18}$ is hydrogen, hydrocarbyl or substituted hydrocarbyl; and said bretylium cation or said source of a bretylium cation and said facilitating anion or said source of a facilitating anion together are present in said pharmaceutical combination in a therapeutically effective amount.

100. A pharmaceutical combination as set forth in claim 99 wherein said combination comprises a pharmaceutical composition comprising:

a bretylium cation; and a facilitating anion, said facilitating anion being selected from the group consisting of:

$R^2SO_3^-$,

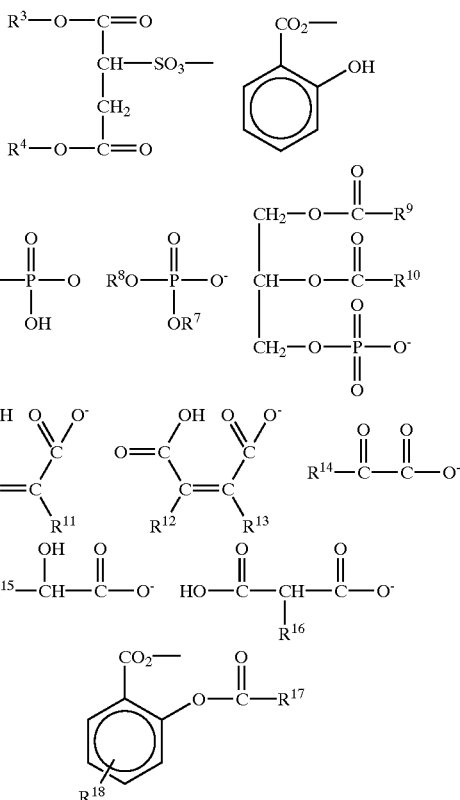

a pseudo-icosahedral carborane anion ($CB_{11}H_{12}^-$), and a substituted pseudo-icosahedral carborane anion, wherein:

$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and the substituent(s) of the substituted pseudo-icosahedral carborane anion are independently hydrocarbyl or substituted hydrocarbyl;

$R^{18}$ is hydrogen, hydrocarbyl or substituted hydrocarbyl; and said bretylium cation and said facilitating anion together are present in said pharmaceutical composition in a therapeutically effective amount.

101. A pharmaceutical combination as set forth in claim 100, wherein $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and the substituent(s) of the substituted pseudo-icosahedral carborane anion are independently hydrocarbyl and $R^{18}$ is hydrogen.

102. A pharmaceutical combination as set forth in claim 100, wherein said combination further comprises a neutralizing agent.

103. A pharmaceutical combination as set forth in claim 100, wherein said combination further comprises a buffering agent.

104. A pharmaceutical combination as set forth in claim 100, wherein said combination further comprises an anti-hypotensive agent.

105. A pharmaceutical combination as set forth in claim 100, wherein said combination further comprises a β-receptor blocker.

106. A pharmaceutical combination as set forth in claim 100, wherein said combination comprises a compound which comprises both said bretylium cation and said facilitating anion.

107. A pharmaceutical combination as set forth in claim 100, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

108. A pharmaceutical combination as set forth in claim 100, wherein said combination comprises (a) a compound which comprises said bretylium cation, and (b) another compound which comprises said facilitating anion.

109. A pharmaceutical combination as set forth in claim 99 wherein said combination comprises a pharmaceutical kit comprising:
  a source of a bretylium cation; and
  a source of a facilitating anion,
  said facilitating anion being selected from the group consisting of:
  $R^2SO_3^-$,

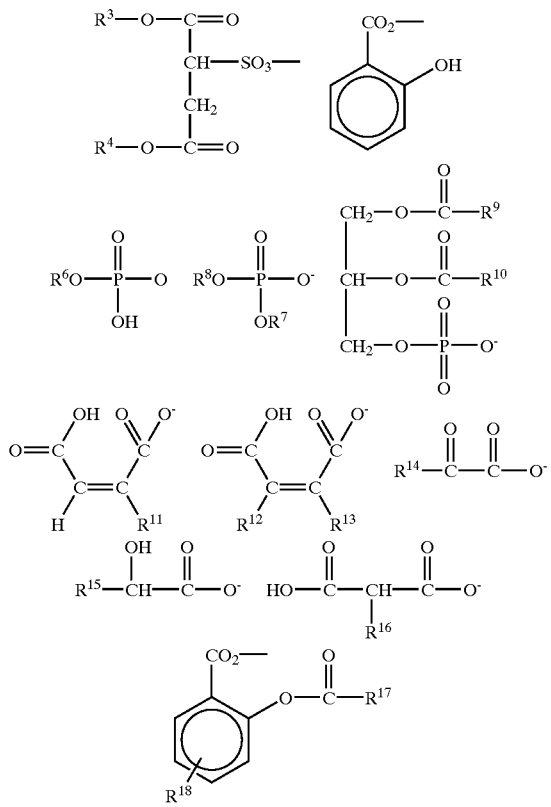

a pseudo-icosahedral carborane anion ($CB_{11}H_{12}^-$), and a substituted pseudo-icosahedral carborane anion, wherein:
  $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and the substituent(s) of the substituted pseudo-icosahedral carborane anion are independently hydrocarbyl or substituted hydrocarbyl;
  $R^{18}$ is hydrogen, hydrocarbyl or substituted hydrocarbyl; and
  said source of bretylium cation and said source of facilitating anion are present in said kit in a therapeutically effective amount.

110. A pharmaceutical combination as set forth in claim 109, wherein $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R_{16}$, $R^{17}$ and the substituent(s) of the substituted pseudo-icosahedral carborane anion are independently hydrocarbyl and $R^{18}$ is hydrogen.

111. A pharmaceutical combination as set forth in claim 109, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

112. A pharmaceutical combination useful for preventing and/or treating a cardiovascular condition, said pharmaceutical combination comprising a bretylium cation or a source of a bretylium cation and an anion or a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:
  said bretylium cation or said source of bretylium cation and said facilitating anion or said source of facilitating anion are, in combination, suitable for oral ingestion;
  said bretylium cation or said source of bretylium cation and said facilitating anion or said source of facilitating anion are capable of forming a mixture comprising both said bretylium cation and said anion within the gastrointestinal tract of a subject upon ingestion by said subject; and
  said bretylium cation or said source of said bretylium cation and said anion or said source of said anion together are present in said pharmaceutical composition in a therapeutically effective amount.

113. A pharmaceutical combination as set forth in claim 112 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:
  said pharmaceutical composition is suitable for oral ingestion;
  said pharmaceutical composition is capable of forming a mixture comprising both said bretylium cation and said anion within the gastrointestinal tract of a subject upon ingestion by said subject; and
  said bretylium cation and said anion together are present in said pharmaceutical composition in a therapeutically effective amount.

114. A pharmaceutical combination as set forth in claim 113, wherein said combination further comprises a neutralizing agent.

115. A pharmaceutical combination as set forth in claim 113, wherein said combination further comprises a buffering agent.

116. A pharmaceutical combination as set forth in claim 113, wherein said combination further comprises an anti-hypotensive agent.

117. A pharmaceutical combination as set forth in claim 113, wherein said combination further comprises a β-receptor blocker.

118. A pharmaceutical combination as set forth in claim 113, wherein said combination comprises a compound which comprises both said bretylium cation and said anion.

119. A pharmaceutical combination as set forth in claim 113, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

120. A pharmaceutical combination as set forth in claim 113, wherein said combination comprises (a) a compound which comprises said bretylium cation, and (b) another compound which comprises said anion.

121. A pharmaceutical combination as set forth in claim 112 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of bretylium cation and said source of said anion are, in combination, suitable for oral ingestion;

said source of said bretylium cation and said source of said anion are capable of forming a mixture comprising both said bretylium cation and said anion within the gastrointestinal tract of a subject upon ingestion by said subject of said source of bretylium cation and said source of said anion; and said source of said bretylium cation and said source of said anion are present in said kit in a therapeutically effective amount.

122. A pharmaceutical combination as set forth in claim 121, wherein said combination comprises a pharmaceutical kit comprising at least 3 separate unit dosages, said unit dosages being (a) a unit dosage comprising said bretylium cation, (b) a unit dosage comprising said anion, and (c) a unit dosage comprising a neutralizing agent, a buffering agent, an anti-hypotensive agent, and/or a β-receptor blocker.

123. A pharmaceutical combination useful for preventing and/or treating a cardiovascular condition, said combination comprising:

a bretylium cation or a source of a bretylium cation;

a neutralizing agent, an anti-hypotensive agent and/or a β-receptor blocker, or a source of a neutralizing agent, an anti-hypotensive agent and/or a β-receptor blocker; and an anion or a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein said bretylium cation or source of bretylium cation, said anion or said source of said anion, and said neutralizing agent, said anti-hypotensive agent, and/or said β-receptor blocker or said source of said neutralizing agent, anti-hypotensive agent and/or said β-receptor blocker together are present in said combination in a therapeutically effective amount.

124. A pharmaceutical combination as set forth in claim 123 wherein said combination comprises a pharmaceutical composition comprising:

a bretylium cation;

a neutralizing agent, an anti-hypotensive agent, and/or a β-receptor blocker; and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein said bretylium cation, said anion, and said neutralizing agent, said anti-hypotensive agent, and/or said β-receptor blocker, together are present in said pharmaceutical composition in a therapeutically effective amount.

125. A pharmaceutical combination as set forth in claim 124, wherein said combination further comprises a buffering agent.

126. A pharmaceutical combination as set forth in claim 124, wherein said combination comprises a compound which comprises both said bretylium cation and said anion.

127. A pharmaceutical combination as set forth in claim 124, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

128. A pharmaceutical combination as set forth in claim 124, wherein said combination comprises (a) a compound which comprises said bretylium cation, and (b) another compound which comprises said anion.

129. A pharmaceutical combination as set forth in claim 124 wherein said combination comprises a pharmaceutical composition suitable for administration via injection; and said bretylium cation and said anion together are present in said pharmaceutical composition in a therapeutically effective amount.

130. A pharmaceutical combination as set forth in claim 123 wherein said combination comprises a pharmaceutical kit comprising:

a source of a bretylium cation;

a source of a neutralizing agent, an anti-hypotensive agent, and/or a β-receptor blocker; and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein said source of bretylium cation, said source of said anion, and said source of said neutralizing agent, said anti-hypotensive agent, and/or said β-receptor blocker, are present in said kit in a therapeutically effective amount.

131. A pharmaceutical combination as set forth in claim 130, wherein said combination comprises a pharmaceutical kit comprising at least 3 separate unit dosages, said unit dosages being (a) a unit dosage comprising said bretylium cation, (b) a unit dosage comprising said anion, and (c) a unit dosage comprising said neutralizing agent, anti-hypotensive agent, and/or β-receptor blocker.

132. A pharmaceutical combination useful for preventing and/or treating a cardiovascular condition, said pharmaceutical combination comprising a bretylium cation or a source of a bretylium cation and acetylsalicylic acid or a source of acetylsalicylic acid.

133. A pharmaceutical combination as set forth in claim 132 wherein said combination comprises a pharmaceutical composition comprising a bretylium cation and acetylsalicylic acid, wherein:

said pharmaceutical composition is suitable for oral ingestion;

said pharmaceutical composition is capable of forming a mixture comprising both said bretylium cation and acetylsalicylic acid or acetylsalicylate ion in the gastrointestinal tract of a subject upon ingestion by said subject; and said bretylium cation and acetylsalicylic acid together are present in said pharmaceutical composition in a therapeutically effective amount.

134. A pharmaceutical combination as set forth in claim 133, wherein said combination further comprises a neutralizing agent.

135. A pharmaceutical combination as set forth in claim 133, wherein said combination further comprises a buffering agent.

136. A pharmaceutical combination as set forth in claim 133, wherein said combination further comprises an anti-hypotensive agent.

137. A pharmaceutical combination as set forth in claim 133, wherein said combination further comprises a β-receptor blocker.

138. A pharmaceutical combination as set forth in claim 133, wherein said combination further comprises a pharmaceutically acceptable adjuvant or excipient.

139. A pharmaceutical combination as set forth in claim 133, wherein said combination contains between about 0.1 and about 100 moles acetylsalicylic acid per mole bretylium ion.

140. A pharmaceutical combination as set forth in claim 132 wherein said combination comprises a pharmaceutical kit comprising a source of a bretylium cation and a source of acetylsalicylic acid, wherein:
    said source of bretylium cation and said source of acetylsalicylic acid are, in combination, suitable for oral ingestion;
    said source of bretylium cation and said source of acetylsalicylic acid are capable of forming a mixture comprising both said bretylium cation and acetylsalicylic acid or acetylsalicylate ion within the gastrointestinal tract of a subject upon ingestion by said subject of said source of bretylium cation and said source of acetylsalicylic acid; and
    said source of said bretylium cation and said source of acetylsalicylic acid are present in said kit in a therapeutically effective amount.

141. A pharmaceutical combination as set forth in claim 140, wherein said combination comprises a pharmaceutical kit comprising at least 3 separate unit dosages, said unit dosages being (a) a unit dosage comprising said bretylium cation, (b) a unit dosage comprising said acetylsalicylic acid, and (c) a unit dosage comprising a neutralizing agent, a buffering agent, an anti-hypotensive agent, and/or a β-receptor blocker.

142. A pharmaceutical combination as set forth in claim 132 wherein said combination comprises a pharmaceutical composition comprising:
    a bretylium cation;
    a neutralizing agent, an anti-hypotensive agent, and/or a β-receptor blocker; and
    acetylsalicylic acid, wherein
    said bretylium cation, said acetylsalicylic acid, and said neutralizing agent, said anti-hypotensive agent, and/or said β-receptor blocker are present in said pharmaceutical composition in a therapeutically effective amount.

143. A pharmaceutical combination as set forth in claim 132 wherein said combination comprises a pharmaceutical kit comprising:
    a source of a bretylium cation;
    a source of acetylsalicylic acid;
    a source of a neutralizing agent, an anti-hypotensive agent, and/or a β-receptor blocker, wherein
    said source of bretylium cation, said source of acetylsalicylic acid, and said source of said neutralizing agent, said anti-hypotensive agent, and/or said β-receptor blocker are present in said kit in a therapeutically effective amount.

144. A pharmaceutical combination as set forth in claim 132, wherein said combination comprises a pharmaceutical composition comprising a bretylium cation and acetylsalicylic acid, wherein:
    said pharmaceutical composition is suitable for administration via injection; and
    said bretylium cation and acetylsalicylic acid together are present in said pharmaceutical composition in a therapeutically effective amount.

145. A pharmaceutical combination as set forth in claim 132, wherein said combination comprises a pharmaceutical composition comprising a bretylium salt and aspirin.

146. A pharmaceutical combination as set forth in claim 145 wherein said pharmaceutical composition comprises a bretylium salt of a hydrophobic anion.

147. A pharmaceutical combination as set forth in claim 146 wherein said bretylium salt is selected from the group consisting of bretylium acetylsalicylate, bretylium salicylate and bretylium laurylsulfate.

148. A pharmaceutical combination as set forth in claim 146, wherein said pharmaceutical composition comprises bretylium tosylate.

149. A pharmaceutical combination as set forth in claim 146, wherein said combination further comprises a pharmaceutically acceptable adjuvant or excipient.

150. A pharmaceutical combination as set forth in claim 146, wherein said combination contains between about 0.1 and about 100 moles aspirin per mole bretylium ion.

151. A pharmaceutical combination as set forth in claim 150, wherein said combination contains between about 0.2 and about 50 moles aspirin per mole bretylium ion.

152. A pharmaceutical combination as set forth in claim 150, wherein said combination contains at least about 0.5 moles aspirin per mole bretylium ion.

153. A pharmaceutical combination useful for preventing and/or treating a cardiovascular condition, said pharmaceutical combination comprising:
    a bretylium cation or a source of a bretylium cation, and
    a facilitating anion or a source of a facilitating anion, wherein:
        said facilitating anion is less hydrophilic than a tosylate anion;
        said bretylium cation or said source of bretylium cation and said facilitating anion or said source of facilitating anion are capable of forming a mixture comprising both a bretylium cation and a facilitating anion within the myocardium of a subject upon administration of said combination to said subject;
        said bretylium cation or said source of bretylium cation and said facilitating anion or said source of facilitating anion together are present in said pharmaceutical combination in a therapeutically effective amount; and
        when the components of said pharmaceutical combination are administered to a human, the area under a plot of the bretylium cation concentration in said human's myocardium versus time over about 30 minutes following said oral administration is greater than the area under a plot of the bretylium cation concentration in the myocardium versus time over about 30 minutes following an administration of bretylium tosylate in an amount which supplies an equivalent amount of the bretylium cation as is supplied by said administration of the components of said pharmaceutical combination.

154. A pharmaceutical combination as set forth in claim 153 wherein said combination comprises a pharmaceutical composition comprising a bretylium cation and a facilitating anion, wherein:
    said facilitating anion is less hydrophilic than a tosylate anion;
    said pharmaceutical composition is capable of forming a mixture comprising both a bretylium cation and a facilitating anion within the myocardium of a subject upon administration of the composition to said subject;
    said bretylium cation and said facilitating anion together are present in said pharmaceutical composition in a therapeutically effective amount; and when said pharmaceutical composition is administered to a human, the area under a plot of the bretylium cation concentration in said human's myocardium versus time over about 30 minutes following said oral administration is greater than the area under a plot of the bretylium cation concentration in the myocardium versus time over about 30 minutes following an administration of bretylium tosylate in an amount which supplies an equivalent amount of the bretylium cation as is supplied by said administration of said pharmaceutical composition.

155. A pharmaceutical combination as set forth in claim 154, wherein said combination further comprises a neutralizing agent.

156. A pharmaceutical combination as set forth in claim 154, wherein said combination further comprises a buffering agent.

157. A pharmaceutical combination as set forth in claim 154, wherein said combination further comprises an anti-hypotensive agent.

158. A pharmaceutical combination as set forth in claim 154, wherein said combination further comprises a β-receptor blocker.

159. A pharmaceutical combination as set forth in claim 154, wherein said combination comprises a compound which comprises both said bretylium cation and said facilitating anion.

160. A pharmaceutical combination as set forth in claim 154, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

161. A pharmaceutical combination as set forth in claim 154, wherein said combination comprises (a) a compound which comprises said bretylium cation, and (b) another compound which comprises said facilitating anion.

162. A pharmaceutical combination as set forth in claim 153 wherein said combination comprises a pharmaceutical kit comprising a source of a bretylium cation and a source of a facilitating anion, wherein:
  said facilitating anion is less hydrophilic than a tosylate anion;
  said source of said bretylium cation and said source of said facilitating anion are capable of forming a mixture comprising both said bretylium cation and said facilitating anion within the myocardium of a subject upon administration of the components of the kit to said subject;
  said source of bretylium cation and said source of facilitating anion together are present in said pharmaceutical kit in a therapeutically effective amount; and
  when the components contained in said pharmaceutical kit are administered to a human, the area under a plot of the bretylium cation concentration in said human's myocardium versus time over about 30 minutes following said oral administration is greater than the area under a plot of the bretylium cation concentration in the myocardium versus time over about 30 minutes following an administration of bretylium tosylate in an amount which supplies an equivalent amount of the bretylium cation as is supplied by said administration of the components of said pharmaceutical kit.

163. A pharmaceutical combination as set forth in claim 162, wherein said combination comprises a pharmaceutical kit comprising at least 3 separate unit dosages, said unit dosages being (a) a unit dosage comprising said bretylium cation, (b) a unit dosage comprising said facilitating anion, and (c) a unit dosage comprising a neutralizing agent, a buffering agent, an anti-hypotensive agent, and/or a β-receptor blocker.

164. A pharmaceutical combination useful for preventing and/or treating a cardiovascular condition, said pharmaceutical combination comprising:
  a bretylium cation or a source of a bretylium cation and an anion or a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:
  said bretylium cation or said source of bretylium cation and said facilitating anion or said source of facilitating anion are capable of forming a mixture comprising both said bretylium cation and said anion within the myocardium of a subject upon administration of said combination to said subject; and
  said bretylium cation or said source of said bretylium cation and said anion or said source of said anion together are present in said pharmaceutical combination in a therapeutically effective amount.

165. A pharmaceutical combination as set forth in claim 164 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:
  said pharmaceutical composition is capable of forming a mixture comprising both said bretylium cation and said anion within the myocardium of a subject upon administration of said composition to said subject; and
  said bretylium cation and said anion together are present in said pharmaceutical composition in a therapeutically effective amount.

166. A pharmaceutical combination as set forth in claim 165, wherein said combination further comprises a neutralizing agent.

167. A pharmaceutical combination as set forth in claim 165, wherein said combination further comprises a buffering agent.

168. A pharmaceutical combination as set forth in claim 165, wherein said combination further comprises an anti-hypotensive agent.

169. A pharmaceutical combination as set forth in claim 165, wherein said combination further comprises a β-receptor blocker.

170. A pharmaceutical combination as set forth in claim 165, wherein said combination comprises a compound which comprises both said bretylium cation and said anion.

171. A pharmaceutical combination as set forth in claim 165, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

172. A pharmaceutical combination as set forth in claim 165, wherein said combination comprises (a) a compound which comprises said bretylium cation, and (b) another compound which comprises said anion.

173. A pharmaceutical combination as set forth in claim 164 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of said bretylium cation and said source of said anion are capable of forming a mixture comprising both said bretylium cation and said anion within the myocardium of a subject upon administration of said source of bretylium cation and said source of said anion to said subject; and said source of said bretylium cation and said source of said anion are present in said kit in a therapeutically effective amount.

174. A pharmaceutical combination as set forth in claim 173, wherein said combination comprises a pharmaceutical kit comprising at least 3 separate unit dosages, said unit dosages being (a) a unit dosage comprising said bretylium cation, (b) a unit dosage comprising said anion, and (c) a unit dosage comprising a neutralizing agent, a buffering agent, an anti-hypotensive agent, and/or a β-receptor blocker.

175. A pharmaceutical combination useful for preventing and/or treating a cardiovascular condition, said pharmaceutical combination comprising a bretylium cation or a source of a bretylium cation and an anion or a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said bretylium cation or said source of bretylium cation and said anion or said source of said anion are capable of forming a mixture comprising both said bretylium cation and said anion within the myocardium of a subject upon parenteral administration of the combination to said subject; and said bretylium cation or said source of said bretylium cation and said anion or said source of said anion together are present in said pharmaceutical combination in a therapeutically effective amount.

176. A pharmaceutical combination as set forth in claim 175 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said pharmaceutical composition is capable of forming a mixture comprising both said bretylium cation and said anion within the myocardium of a subject upon parenteral administration of said composition to said subject; and said bretylium cation and said anion together are present in said pharmaceutical composition in a therapeutically effective amount.

177. A pharmaceutical combination as set forth in claim 176, wherein said combination further comprises a neutralizing agent.

178. A pharmaceutical combination as set forth in claim 176, wherein said combination further comprises a buffering agent.

179. A pharmaceutical combination as set forth in claim 176, wherein said combination further comprises an anti-hypotensive agent.

180. A pharmaceutical combination as set forth in claim 176, wherein said combination further comprises a β-receptor blocker.

181. A pharmaceutical combination as set forth in claim 176, wherein said combination comprises a compound which comprises both said bretylium cation and said anion.

182. A pharmaceutical combination as set forth in claim 176, wherein said combination comprises bretylium di(2-ethylhexyl)sulfosuccinate, bretylium salicylate, bretylium acetylsalicylate, bretylium lauryl sulfate, bretylium di(2-ethylhexyl) phosphate, or bretylium hexadecylsulfonate.

183. A pharmaceutical combination as set forth in claim 176, wherein said combination comprises (a) a compound which comprises said bretylium cation, and (b) another compound which comprises said anion.

184. A pharmaceutical combination as set forth in claim 175 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of said bretylium cation and said source of said anion are capable of forming a mixture comprising both said bretylium cation and said anion within the myocardium of a subject upon parenteral administration of said source of bretylium cation and said source of said anion to said subject; and said source of said bretylium cation and said source of said anion are present in said kit in a therapeutically effective amount.

185. A pharmaceutical combination as set forth in claim 184, wherein said combination comprises a pharmaceutical kit comprising at least 3 separate unit dosages, said unit dosages being (a) a unit dosage comprising said bretylium cation, (b) a unit dosage comprising said anion, and (c) a unit dosage comprising a neutralizing agent, a buffering agent, an anti-hypotensive agent, and/or a β-receptor blocker.

186. A pharmaceutical combination useful for preventing and/or treating a cardiovascular condition, said pharmaceutical combination comprising a bretylium cation or a source of a bretylium cation and at least one β-receptor blocker or a source of a β-receptor blocker, wherein said bretylium cation or said source of bretylium cation and said β-receptor blocker or said source of a β-receptor blocker together are present in said pharmaceutical combination in a therapeutically effective amount.

187. A pharmaceutical combination as set forth in claim 186 wherein said combination comprises a pharmaceutical composition comprising a bretylium cation and at least one β-receptor blocker, wherein said bretylium cation and said β-receptor blocker together are present in said pharmaceutical composition in a therapeutically effective amount.

188. A pharmaceutical combination as set forth in claim 187 wherein said β-receptor blocker is selected from the group consisting of propranolol, atenolol, esmolol, metoprolol, labetalol, talinolol, timolol, acebutolol, dichloroisoproterenol, pronethalol, sotalol, oxprenolol, alprenolol, practolol, nadolol, pindolol, penbutolol, and carvedilol.

189. A pharmaceutical combination as set forth in claim 186 wherein said combination comprises a pharmaceutical kit comprising a source of a bretylium cation and at least one source of a β-receptor blocker, wherein said source of a bretylium cation and said source of a β-receptor blocker are present in said kit in a therapeutically effective amount.

190. A pharmaceutical combination as set forth in claim 189 wherein said β-receptor blocker is selected from the group consisting of propranolol, atenolol, esmolol, metoprolol, labetalol, talinolol, timolol, acebutolol, dichloroisoproterenol, pronethalol, sotalol, oxprenolol, alprenolol, practolol, nadolol, pindolol, penbutolol, and carvedilol.

191. A pharmaceutical composition comprising bretylium acetylsalicylate.

192. A pharmaceutical composition comprising bretylium salicylate.

193. A pharmaceutical composition comprising bretylium laurylsulfate.

194. A pharmaceutical composition comprising a salt of bretylium and a β-receptor blocker.

195. A pharmaceutical composition as set forth in claim 194 comprising a bretylium salt of a hydrophobic anion.

196. A pharmaceutical composition as set forth in claim 195 wherein said bretylium salt is selected from the group consisting of bretylium acetylsalicylate, bretylium salicylate and bretylium laurylsulfate.

197. A pharmaceutical composition as set forth in claim 195 comprising bretylium tosylate.

198. A method for treatment of atrial fibrillation comprising administering an anti-fibrillation pharmaceutical composition to a patient susceptible to atrial fibrillation, said anti-fibrillation composition comprising aspirin and a bretylium ion.

199. A method as set forth in claim 198 wherein said composition is administered in a dosage of at least about 1 mg/kg.

200. A method as set forth in claim 199 wherein said composition is administered in a dosage of at least about 2 mg/kg.

201. A method as set forth in claim 199 wherein said composition is administered in a dosage between about 2 and about 100 mg/kg.

202. A method as set forth in claim 201 wherein said composition is administered in a dosage between about 5 and about 50 mg/kg.

203. A method as set forth in claim 202 wherein said composition is administered in a dosage of from about 10 and about 30 mg/kg.

204. A pharmaceutical composition comprising a nonpeptide quaternary ammonium cation and a facilitating anion, said ammonium cation comprising a therapeutic agent, said cation and said anion together being present in a therapeutic amount, and said facilitating anion being characterized as less hydrophilic than a tosylate anion.

205. A pharmaceutical composition as set forth in claim 204 comprising propyromazine.

206. A pharmaceutical composition as set forth in claim 204 wherein said facilitating anion is selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate.

207. A method for preventing and/or treating a cardiovascular condition comprising administering a pharmaceutical combination comprising a bretylium cation and a facilitating anion to a subject in need thereof, wherein said facilitating anion is less hydrophilic than a tosylate anion.

208. A method for preventing and/or treating a cardiovascular condition comprising administering a pharmaceutical combination of claim 1 to a subject in need thereof.

209. A method as set forth in claim 208 wherein said combination comprises a pharmaceutical composition comprising:
a bretylium cation,
a facilitating anion, and
an anti-hypotensive agent and/or a β-receptor blocker, wherein:
said facilitating anion is less hydrophilic than a tosylate anion; and
said bretylium cation, said facilitating anion, and said anti-hypotensive agent and/or said β-receptor blocker together are present in said pharmaceutical composition in a therapeutically effective amount.

210. A method as set forth in claim 208 wherein said combination comprises a pharmaceutical composition comprising:
0.5% to 60% bretylium cation,
0.3% to 60% facilitating anion,
0.0% to 0.5% anti-hypotensive agent,
0.0% to 1.0% β-receptor blocker, and
0.02% to 99% neutralizing agent.

211. A method as set forth in claim 208 wherein said combination comprises a pharmaceutical kit comprising:
a source of a bretylium cation,
a source of a facilitating anion, and
a source of an anti-hypotensive agent and/or a β-receptor blocker, wherein:
said facilitating anion is less hydrophilic than a tosylate anion; and
said source of bretylium cation, said source of facilitating anion, and said source of anti-hypotensive agent and/or β-receptor blocker together are present in said pharmaceutical kit in a therapeutically effective amount.

212. A method for preventing and/or treating a cardiovascular condition comprising orally administering a pharmaceutical combination of claim 32 to a subject in need thereof.

213. A method as set forth in claim 212 wherein said combination comprises a pharmaceutical composition comprising a bretylium cation and a facilitating anion, wherein:
said facilitating anion is less hydrophilic than a tosylate anion;
said pharmaceutical composition is suitable for oral ingestion;
said pharmaceutical composition is capable of forming a mixture comprising both a bretylium cation and a facilitating anion within the gastrointestinal tract of a subject upon ingestion by said subject;
said bretylium cation and said facilitating anion together are present in said pharmaceutical composition in a therapeutically effective amount; and
when said pharmaceutical composition is orally administered to a human, the area under a plot of the bretylium cation concentration in said human's myocardium versus time over about 30 minutes following said oral administration is greater than the area under a plot of the bretylium cation concentration in the myocardium versus time over about 30 minutes following an oral administration of bretylium tosylate in an amount which supplies an equivalent amount of the bretylium cation as is supplied by said oral administration of said pharmaceutical composition.

214. A method as set forth in claim 212 wherein said combination comprises a pharmaceutical kit comprising a source of a bretylium cation and a source of a facilitating anion, wherein:
said facilitating anion is less hydrophilic than a tosylate anion;
said source of said bretylium cation and said source of said facilitating anion are, in combination, suitable for oral ingestion;
said source of said bretylium cation and said source of said facilitating anion are capable of forming a mixture comprising both said bretylium cation and said facilitating anion within the gastrointestinal tract of a subject upon ingestion by said subject;

said source of bretylium cation and said source of facilitating anion together are present in said pharmaceutical kit in a therapeutically effective amount; and when the components contained in said pharmaceutical kit are orally administered to a human, the area under a plot of the bretylium cation concentration in said human's myocardium versus time over about 30 minutes following said oral administration is greater than the area under a plot of the bretylium cation concentration in the myocardium versus time over about 30 minutes following an oral administration of bretylium tosylate in an amount which supplies an equivalent amount of the bretylium cation as is supplied by said oral administration of the components of said pharmaceutical kit.

215. A method for preventing and/or treating a cardiovascular condition comprising orally administering a pharmaceutical combination of claim 43 to a subject in need thereof.

216. A method as set forth in claim 215 wherein said combination comprises a pharmaceutical composition comprising a bretylium cation and a facilitating anion, wherein:

said pharmaceutical composition is suitable for oral ingestion;

said pharmaceutical composition is capable of forming a mixture comprising both said bretylium cation and said facilitating anion within the gastrointestinal tract of a subject upon ingestion by said subject;

said bretylium cation and said facilitating anion together are present in said pharmaceutical composition in a therapeutically effective amount; and when said pharmaceutical composition is orally administered to a human, the area under a plot of the bretylium cation concentration in said human's blood versus time over about 30 minutes following said oral administration is greater than the area under a plot of the bretylium cation concentration in the blood versus time over about 30 minutes following an oral administration of bretylium tosylate in an amount which supplies an equivalent amount of the bretylium cation as is supplied by said oral administration of said pharmaceutical composition.

217. A method as set forth in claim 215 wherein said combination comprises a pharmaceutical kit comprising a source of a bretylium cation and a source of a facilitating anion, wherein:

said source of bretylium cation and said source of facilitating anion are, in combination, suitable for oral ingestion;

said source of bretylium cation and said source of facilitating anion are capable of forming a mixture comprising both said bretylium cation and said facilitating anion within the gastrointestinal tract of a subject upon ingestion by said subject;

said source of bretylium cation and said source of facilitating anion together are present in said pharmaceutical kit in a therapeutically effective amount; and when the components contained in said pharmaceutical kit are orally administered to a human, the area under a plot of the bretylium cation concentration in said human's blood versus time over about 30 minutes following said oral administration is greater than the area under a plot of the bretylium cation concentration in the blood versus time over about 30 minutes following an oral administration of bretylium tosylate in an amount which supplies an equivalent amount of the bretylium cation as is supplied by said oral administration of the components contained in said pharmaceutical kit.

218. A method for preventing and/or treating a cardiovascular condition comprising administering a pharmaceutical combination of claim 54 to a subject in need thereof.

219. A method as set forth in claim 218 wherein said combination comprises a pharmaceutical composition comprising a bretylium cation and a facilitating anion selected from the group consisting of:

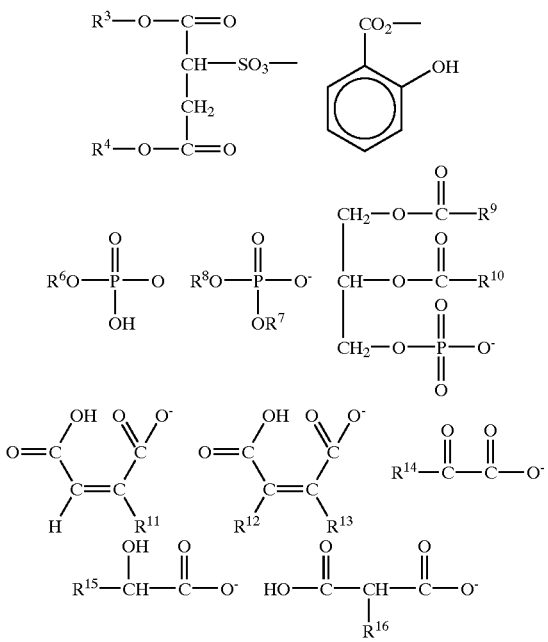

a pseudo-icosahedral carborane anion ($CB_{11}H_{12}^-$), and a substituted pseudo-icosahedral carborane anion, wherein:

$R^2, R^3, R^4, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and said bretylium cation and said facilitating anion together are present in said pharmaceutical composition in a therapeutically effective amount.

220. A method as set forth in claim 218 wherein said combination comprises a pharmaceutical kit comprising a source of a bretylium cation and a source of a facilitating anion, said facilitating anion being selected from the group consisting of:

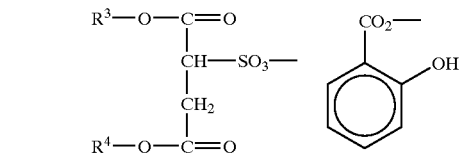

-continued

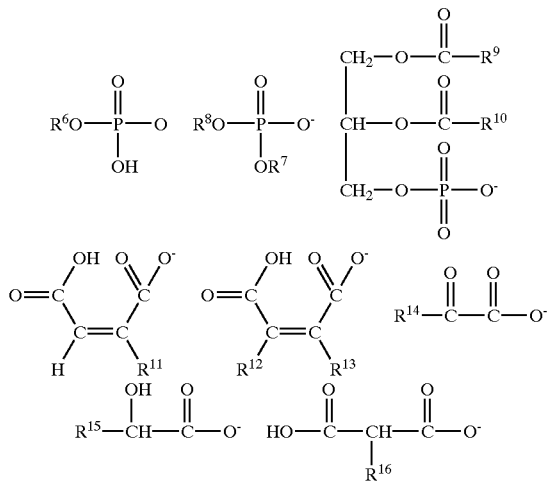

a pseudo-icosahedral carborane anion ($CB_{11}H_{12}^-$), and
a substituted pseudo-icosahedral carborane anion,
wherein:
$R^2, R^3, R^4, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and
said source of bretylium cation and said source of facilitating anion are present in said kit in a therapeutically effective amount.

221. A method for preventing and/or treating a cardiovascular condition comprising administering a pharmaceutical combination of claim 86 to a subject in need thereof.

222. A method as set forth in claim 221 wherein said combination comprises a pharmaceutical composition comprising:
a bretylium cation;
a neutralizing agent, an anti-hypotensive agent, and/or a β-receptor blocker; and
a facilitating anion selected from the group consisting of:
$R^2SO_3^-$,

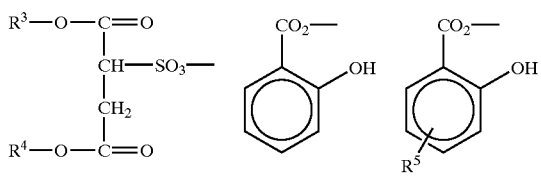

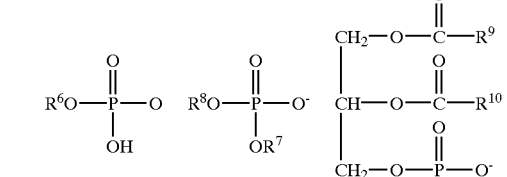

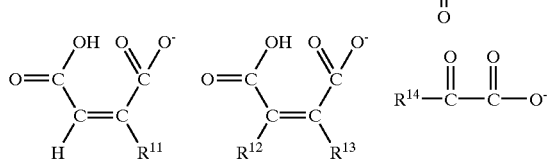

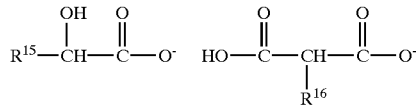

a pseudo-icosahedral carborane anion ($CB_{11}H_{12}^-$), and
a substituted pseudo-icosahedral carborane anion,
wherein:
$R^2, R^3, R^4, R^5, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and
said bretylium cation; said facilitating anion; and said neutralizing agent, anti-hypotensive agent, and/or β-receptor blocker are present in said pharmaceutical composition in a therapeutically effective amount.

223. A method as set forth in claim 221 wherein said combination comprises a pharmaceutical kit comprising:
a source of a bretylium cation;
a source of a neutralizing agent, an anti-hypotensive agent, and/or a β-receptor blocker; and
a source of a facilitating anion,
said facilitating anion being selected from the group consisting of:
$R^2SO_3^-$,

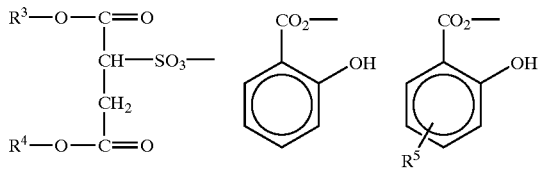

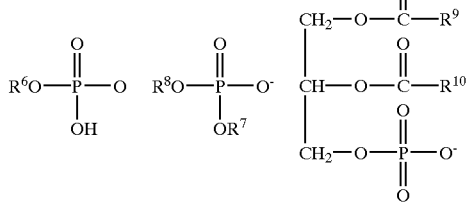

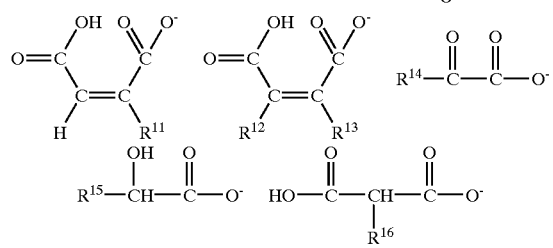

a pseudo-icosahedral carborane anion ($CB_{11}H_{12}^-$), and
a substituted pseudo-icosahedral carborane anion,
wherein:
$R^2, R^3, R^4, R^5, R^6, R^7, R^8, R^9, R^{10}, R^{11}, R^{12}, R^{13}, R^{14}, R^{15}, R^{16}$, and the substituent(s) of the substituted pseudo-icosahedral carborane anion are independently hydrocarbyl or substituted hydrocarbyl; and
said source of a bretylium cation, said source of a facilitating anion, and said source of a neutralizing agent, anti-hypotensive agent, and/or β-receptor blocker together are present in said kit in a therapeutically effective amount.

224. A method for preventing and/or treating a cardiovascular condition comprising administering a pharmaceutical combination of claim 99 to a subject in need thereof.

225. A method as set forth in claim 224 wherein said combination comprises a pharmaceutical composition comprising:
- a bretylium cation; and
- a facilitating anion,
- said facilitating anion being selected from the group consisting of:
  $R^2SO_3^-$,

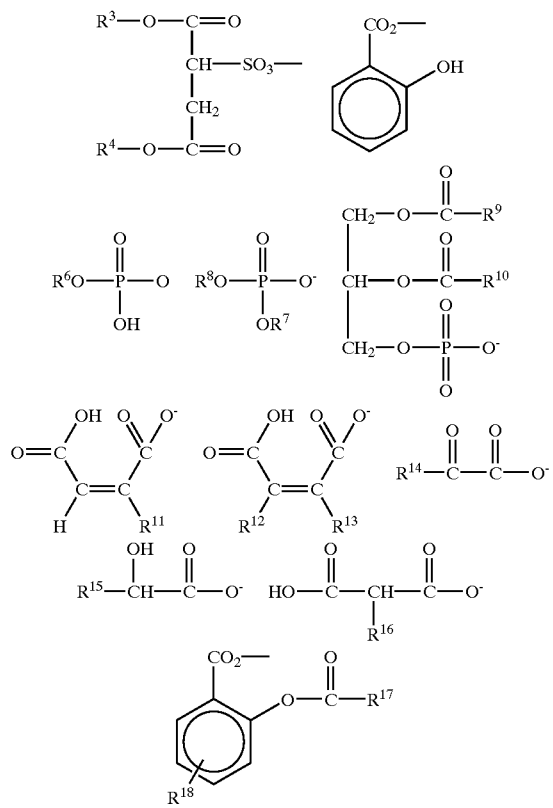

a pseudo-icosahedral carborane anion ($CB_{11}H_{12}^-$), and a substituted pseudo-icosahedral carborane anion, wherein:
$R^2, R^3, R^4, R^5, R^6, R^7, R^8, R^9, R^{10}, R^{11}, R^{12}, R^{13}, R^{14}, R^{15}, R^{16}, R^{17}$ and the substituent(s) of the substituted pseudo-icosahedral carborane anion are independently hydrocarbyl or substituted hydrocarbyl;

$R^{18}$ is hydrogen, hydrocarbyl or substituted hydrocarbyl; and said bretylium cation and said facilitating anion together are present in said pharmaceutical composition in a therapeutically effective amount.

226. A method as set forth in claim 224 wherein said combination comprises a pharmaceutical kit comprising:
- a source of a bretylium cation; and
- a source of a facilitating anion,
- said facilitating anion being selected from the group consisting of:
  $R^2SO_3^-$,

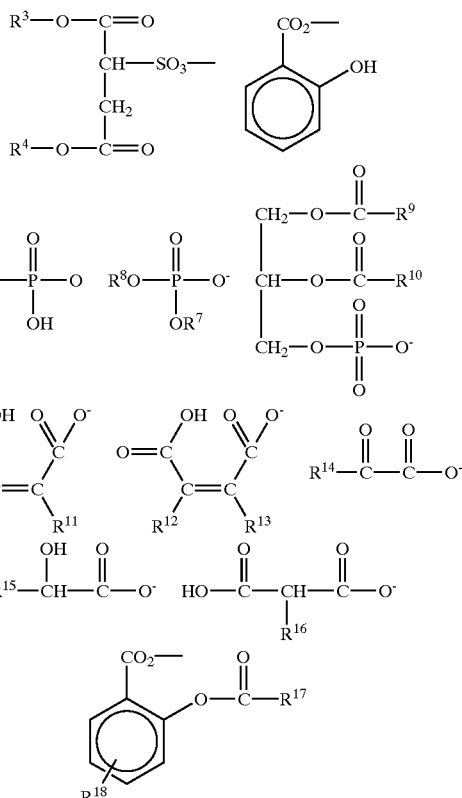

a pseudo-icosahedral carborane anion ($CB_{11}H_{12}^-$), and a substituted pseudo-icosahedral carborane anion, wherein:
$R^2, R^3, R^4, R^5, R^6, R^7, R^8, R^9, R^{10}, R^{11}, R^{12}, R^{13}, R^{14}, R^{15}, R^{16}, R^{17}$ and the substituent(s) of the substituted pseudo-icosahedral carborane anion are independently hydrocarbyl or substituted hydrocarbyl;

$R^{18}$ is hydrogen, hydrocarbyl or substituted hydrocarbyl; and said source of bretylium cation and said source of facilitating anion are present in said kit in a therapeutically effective amount.

227. A method for preventing and/or treating a cardiovascular condition comprising orally administering a pharmaceutical combination of claim 112 to a subject in need thereof.

228. A method as set forth in claim 227 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:
said pharmaceutical composition is suitable for oral ingestion;
said pharmaceutical composition is capable of forming a mixture comprising both said bretylium cation and said anion within the gastrointestinal tract of a subject upon ingestion by said subject; and
said bretylium cation and said anion together are present in said pharmaceutical composition in a therapeutically effective amount.

229. A method as set forth in claim 227 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of bretylium cation and said source of said anion are, in combination, suitable for oral ingestion;

said source of said bretylium cation and said source of said anion are capable of forming a mixture comprising both said bretylium cation and said anion within the gastrointestinal tract of a subject upon ingestion by said subject of said source of bretylium cation and said source of said anion; and said source of said bretylium cation and said source of said anion are present in said kit in a therapeutically effective amount.

230. A method for preventing and/or treating a cardiovascular condition comprising administering a pharmaceutical combination of claim 123 to a subject in need thereof.

231. A method as set forth in claim 230 wherein said pharmaceutical combination comprises a pharmaceutical composition comprising:

a bretylium cation;

a neutralizing agent, an anti-hypotensive agent, and/or a β-receptor blocker; and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein said bretylium cation, said anion, and said neutralizing agent, said anti-hypotensive agent, and/or said β-receptor blocker, together are present in said pharmaceutical composition in a therapeutically effective amount.

232. A method as set forth in claim 230 wherein said pharmaceutical combination comprises a pharmaceutical composition suitable for administration via injection; and said bretylium cation and said anion together are present in said pharmaceutical composition in a therapeutically effective amount.

233. A method as set forth in claim 230 wherein said pharmaceutical combination comprises a pharmaceutical kit comprising:

a source of a bretylium cation;

a source of a neutralizing agent, an anti-hypotensive agent, and/or a β-receptor blocker; and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein said source of bretylium cation, said source of said anion, and said source of said neutralizing agent, said anti-hypotensive agent, and/or said β-receptor blocker, are present in said kit in a therapeutically effective amount.

234. A method for preventing and/or treating a cardiovascular condition comprising administering a pharmaceutical combination of claim 132 to subject in need thereof.

235. A method as set forth in claim 234 wherein said combination comprises a pharmaceutical composition comprising a bretylium cation and acetylsalicylic acid, wherein:

said pharmaceutical composition is suitable for oral ingestion;

said pharmaceutical composition is capable of forming a mixture comprising both said bretylium cation and acetylsalicylic acid or acetylsalicylate ion in the gastrointestinal tract of a subject upon ingestion by said subject; and said bretylium cation and acetylsalicylic acid together are present in said pharmaceutical composition in a therapeutically effective amount.

236. A method as set forth in claim 234 wherein said combination comprises a pharmaceutical kit comprising a source of a bretylium cation and a source of acetylsalicylic acid, wherein:

said source of bretylium cation and said source of acetylsalicylic acid are, in combination, suitable for oral ingestion;

said source of bretylium cation and said source of acetylsalicylic acid are capable of forming a mixture comprising both said bretylium cation and acetylsalicylic acid or acetylsalicylate ion within the gastrointestinal tract of a subject upon ingestion by said subject of said source of bretylium cation and said source of acetylsalicylic acid; and said source of said bretylium cation and said source of acetylsalicylic acid are present in said kit in a therapeutically effective amount.

237. A method as set forth in claim 234 wherein said combination comprises a pharmaceutical composition comprising:

a bretylium cation;

a neutralizing agent, an anti-hypotensive agent, and/or a β-receptor blocker; and acetylsalicylic acid, wherein said bretylium cation, said acetylsalicylic acid, and said neutralizing agent, said anti-hypotensive agent, and/or said β-receptor blocker are present in said pharmaceutical composition in a therapeutically effective amount.

238. A method as set forth in claim 234 wherein said combination comprises a pharmaceutical kit comprising:

a source of a bretylium cation;

a source of acetylsalicylic acid;

a source of a neutralizing agent, an anti-hypotensive agent, and/or a β-receptor blocker, wherein said source of bretylium cation, said source of acetylsalicylic acid, and said source of said neutralizing agent, said anti-hypotensive agent, and/or said β-receptor blocker are present in said kit in a therapeutically effective amount.

239. A method as set forth in claim 234 wherein said combination comprises a pharmaceutical composition comprising a bretylium cation and acetylsalicylic acid, wherein:

said pharmaceutical composition is suitable for administration via injection; and said bretylium cation and acetylsalicylic acid together are present in said pharmaceutical composition in a therapeutically effective amount.

240. A method as set forth in claim 234 wherein said combination comprises a pharmaceutical composition comprising a bretylium salt and aspirin.

241. A method for preventing and/or treating a cardiovascular condition comprising administering a pharmaceutical combination of claim 153 to a subject in need thereof.

242. A method as set forth in claim 241 wherein said combination comprises a pharmaceutical composition comprising a bretylium cation and a facilitating anion, wherein:

said facilitating anion is less hydrophilic than a tosylate anion;

said pharmaceutical composition is capable of forming a mixture comprising both a bretylium cation and a facilitating anion within the myocardium of a subject upon administration of the composition to said subject;

said bretylium cation and said facilitating anion together are present in said pharmaceutical composition in a therapeutically effective amount; and when said pharmaceutical composition is administered to a human, the area under a plot of the bretylium cation concentration in said human's myocardium versus time over about 30 minutes following said oral administration is greater than the area under a plot of the bretylium cation concentration in the myocardium versus time over about 30 minutes following an administration of bretylium tosylate in an amount which supplies an equivalent amount of the bretylium cation as is supplied by said administration of said pharmaceutical composition.

243. A method as set forth in claim 241 wherein said combination comprises a pharmaceutical kit comprising a source of a bretylium cation and a source of a facilitating anion, wherein:

said facilitating anion is less hydrophilic than a tosylate anion;

said source of said bretylium cation and said source of said facilitating anion are capable of forming a mixture comprising both said bretylium cation and said facilitating anion within the myocardium of a subject upon administration of the components of the kit to said subject;

said source of bretylium cation and said source of facilitating anion together are present in said pharmaceutical kit in a therapeutically effective amount; and when the components contained in said pharmaceutical kit are administered to a human, the area under a plot of the bretylium cation concentration in said human's myocardium versus time over about 30 minutes following said oral administration is greater than the area under a plot of the bretylium cation concentration in the myocardium versus time over about 30 minutes following an administration of bretylium tosylate in an amount which supplies an equivalent amount of the bretylium cation as is supplied by said administration of the components of said pharmaceutical kit.

244. A method for preventing and/or treating a cardiovascular condition comprising administering a pharmaceutical combination of claim 164 to a subject in need thereof.

245. A method as set forth in claim 244 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said pharmaceutical composition is capable of forming a mixture comprising both said bretylium cation and said anion within the myocardium of a subject upon administration of said composition to said subject; and said bretylium cation and said anion together are present in said pharmaceutical composition in a therapeutically effective amount.

246. A method as set forth in claim 244 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of said bretylium cation and said source of said anion are capable of forming a mixture comprising both said bretylium cation and said anion within the myocardium of a subject upon administration of said source of bretylium cation and said source of said anion to said subject; and said source of said bretylium cation and said source of said anion are present in said kit in a therapeutically effective amount.

247. A method for preventing and/or treating a cardiovascular condition comprising administering a pharmaceutical combination of claim 175 to a subject in need thereof.

248. A method as set forth in claim 247 wherein said combination comprises a pharmaceutical composition comprising a bretylium cation and an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said pharmaceutical composition is capable of forming a mixture comprising both said bretylium cation and said anion within the myocardium of a subject upon parenteral administration of said composition to said subject; and said bretylium cation and said anion together are present in said pharmaceutical composition in a therapeutically effective amount.

249. A method as set forth in claim 247 wherein said combination comprises a pharmaceutical kit comprising a source of a bretylium cation and a source of an anion selected from the group consisting of salicylate, acetylsalicylate, lauryl sulfate, di(2-ethylhexyl) sulfosuccinate, di(2-ethylhexyl) phosphate, hexadecyl sulfonate and dipalmitoye phosphatidate, wherein:

said source of said bretylium cation and said source of said anion are capable of forming a mixture comprising both said bretylium cation and said anion within the myocardium of a subject upon parenteral administration of said source of bretylium cation and said source of said anion to said subject; and said source of said bretylium cation and said source of said anion are present in said kit in a therapeutically effective amount.

250. A method for preventing and/or treating a cardiovascular condition comprising administering a pharmaceutical combination of claim 186 to a subject in need thereof.

251. A method as set forth in claim 250 wherein said combination comprises a pharmaceutical composition comprising a bretylium cation and at least one β-receptor blocker, wherein said bretylium cation and said β-receptor blocker together are present in said pharmaceutical composition in a therapeutically effective amount.

252. A method as set forth in claim 250 wherein said combination comprises a pharmaceutical kit comprising a source of a bretylium cation and at least one source of a β-receptor blocker, wherein said source of a bretylium cation and said source of a β-receptor blocker are present in said kit in a therapeutically effective amount.

253. A method for preventing and/or treating a cardiovascular condition comprising administering a pharmaceutical composition of claim 191 to a subject in need thereof.

254. A method for preventing and/or treating a cardiovascular condition comprising administering a pharmaceutical composition of claim 192 to a subject in need thereof.

255. A method for preventing and/or treating a cardiovascular condition comprising administering a pharmaceutical composition of claim 193 to a subject in need thereof.

256. A method for preventing and/or treating a cardiovascular condition comprising administering a pharmaceutical composition of claim 194 to a subject in need thereof.

257. A method for preventing and/or treating a cardiovascular condition comprising administering a pharmaceutical composition of claim 198 to a subject in need thereof.

258. A pharmaceutical composition comprising a salt of bretylium and an anti-hypotensive agent, wherein said bretylium salt is selected from the group consisting of bretylium di(2-ethylhexyl)sulfosuccinate, bretylium salicylate, bretylium acetylsalicylate, bretylium lauryl sulfate, bretylium di(2-ethylhexyl)phosphate and bretylium hexadecylsulfonate.

259. A pharmaceutical composition as set forth in claim 258 wherein said anti-hypotensive agent comprises a tricyclic anti-depressant compound.

260. A pharmaceutical composition as set forth in claim 258, wherein said anti-hypotensive agent is selected from the group consisting of protriptyline, amitriptyline, nortriptyline, desipramine, and mazindol.

261. A method for preventing and/or treating a cardiovascular condition comprising administering a pharmaceutical composition of claim 258 to a subject in need thereof.

* * * * *